US012575849B2

(12) United States Patent
Messerly et al.

(10) Patent No.: US 12,575,849 B2
(45) Date of Patent: Mar. 17, 2026

(54) ULTRASONIC SURGICAL INSTRUMENTS HAVING OFFSET BLADES

(71) Applicant: Cilag GmbH International, Zug (CH)

(72) Inventors: Jeffrey D. Messerly, Cincinnati, OH (US); Cory G. Kimball, Hamilton, OH (US); William E. Clem, Bozeman, MT (US); Gregory W. Johnson, Minneapolis, MN (US); Frederick L. Estera, Cincinnati, OH (US); William B. Weisenburgh, II, Maineville, OH (US); Foster B. Stulen, Johns Island, SC (US)

(73) Assignee: Cilag GmbH International, Zug (CH)

( * ) Notice: Subject to any disclaimer, the term of this patent is extended or adjusted under 35 U.S.C. 154(b) by 419 days.

(21) Appl. No.: 16/952,769

(22) Filed: Nov. 19, 2020

(65) Prior Publication Data

US 2021/0128191 A1    May 6, 2021

Related U.S. Application Data

(62) Division of application No. 15/211,402, filed on Jul. 15, 2016, now Pat. No. 10,842,522.

(51) Int. Cl.
*A61B 17/32* (2006.01)
*A61B 17/00* (2006.01)
(Continued)

(52) U.S. Cl.
CPC .............. *A61B 17/320092* (2013.01); *A61B 17/320068* (2013.01); *A61N 7/00* (2013.01);
(Continued)

(58) Field of Classification Search
CPC .............. A61N 7/00; A61B 17/320092; A61B 17/320068; A61B 17/320072;
(Continued)

(56) References Cited

U.S. PATENT DOCUMENTS

| 969,528 A | 9/1910 | Disbrow |
| 1,570,025 A | 1/1926 | Young |
| (Continued) | | |

FOREIGN PATENT DOCUMENTS

| CA | 837241 A | 3/1970 |
| CA | 2535467 A1 | 4/1993 |
| (Continued) | | |

OTHER PUBLICATIONS

Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
(Continued)

*Primary Examiner* — Melanie R Tyson
*Assistant Examiner* — Mikail A Mannan
(74) *Attorney, Agent, or Firm* — Vorys, Sater, Seymour and Pease LLP

(57) ABSTRACT

Ultrasonic surgical instruments having angularly and/or linearly off-set blades are described. The angularly and/or linearly off-set blades may facilitate increased surgical site access, visibility, and manipulability.

9 Claims, 44 Drawing Sheets

(51) Int. Cl.
*A61B 18/00* (2006.01)
*A61N 7/00* (2006.01)

(52) U.S. Cl.
CPC ............... *A61B 2017/00738* (2013.01); *A61B 2017/320072* (2013.01); *A61B 2017/320074* (2017.08); *A61B 2017/320088* (2013.01); *A61B 2017/320094* (2017.08); *A61B 2017/320095* (2017.08); *A61B 2018/00589* (2013.01)

(58) Field of Classification Search
CPC ....... A61B 2017/320074; A61B 2017/320094; A61B 2017/00438; A61B 2017/00738; A61B 2017/320088; A61B 2017/320072; A61B 2018/00589
See application file for complete search history.

(56) References Cited

U.S. PATENT DOCUMENTS

| | | | |
|---|---|---|---|
| 1,813,902 | A | 7/1931 | Bovie |
| 2,188,497 | A | 1/1940 | Calva |
| 2,366,274 | A | 1/1945 | Luth et al. |
| 2,425,245 | A | 8/1947 | Johnson |
| 2,442,966 | A | 6/1948 | Wallace |
| 2,458,152 | A | 1/1949 | Eakins |
| 2,510,693 | A | 6/1950 | Green |
| 2,597,564 | A | 5/1952 | Bugg |
| 2,704,333 | A | 3/1955 | Calosi et al. |
| 2,736,960 | A | 3/1956 | Armstrong |
| 2,743,726 | A | 5/1956 | Grieshaber |
| 2,748,967 | A | 6/1956 | Roach |
| 2,845,072 | A | 7/1958 | Shafer |
| 2,849,788 | A | 9/1958 | Creek |
| 2,867,039 | A | 1/1959 | Zach |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,033,407 | A | 5/1962 | Alfons |
| 3,053,124 | A | 9/1962 | Balamuth et al. |
| 3,082,805 | A | 3/1963 | Royce |
| 3,166,971 | A | 1/1965 | Stoecker |
| 3,322,403 | A | 5/1967 | Murphy |
| 3,432,691 | A | 3/1969 | Shoh |
| 3,433,226 | A | 3/1969 | Boyd |
| 3,489,930 | A | 1/1970 | Shoh |
| 3,503,396 | A | 3/1970 | Pierie et al. |
| 3,503,397 | A | 3/1970 | Fogarty et al. |
| 3,503,398 | A | 3/1970 | Fogarty et al. |
| 3,513,848 | A | 5/1970 | Winston et al. |
| 3,514,856 | A | 6/1970 | Camp et al. |
| 3,525,912 | A | 8/1970 | Wallin |
| 3,526,219 | A | 9/1970 | Balamuth |
| 3,554,198 | A | 1/1971 | Tatoian et al. |
| 3,580,841 | A | 5/1971 | Cadotte et al. |
| 3,606,682 | A | 9/1971 | Camp et al. |
| 3,614,484 | A | 10/1971 | Shoh |
| 3,616,375 | A | 10/1971 | Inoue |
| 3,629,726 | A | 12/1971 | Popescu |
| 3,636,943 | A | 1/1972 | Balamuth |
| 3,668,486 | A | 6/1972 | Silver |
| 3,702,948 | A | 11/1972 | Balamuth |
| 3,703,651 | A | 11/1972 | Blowers |
| 3,776,238 | A | 12/1973 | Peyman et al. |
| 3,777,760 | A | 12/1973 | Essner |
| 3,792,701 | A | 2/1974 | Kloz et al. |
| 3,805,787 | A | 4/1974 | Banko |
| 3,809,977 | A | 5/1974 | Balamuth et al. |
| 3,830,098 | A | 8/1974 | Antonevich |
| 3,832,776 | A | 9/1974 | Sawyer |
| 3,854,737 | A | 12/1974 | Gilliam, Sr. |
| 3,862,630 | A | 1/1975 | Balamuth |
| 3,875,945 | A | 4/1975 | Friedman |
| 3,885,438 | A | 5/1975 | Harris, Sr. et al. |
| 3,900,823 | A | 8/1975 | Sokal et al. |
| 3,918,442 | A | 11/1975 | Nikolaev et al. |
| 3,924,335 | A | 12/1975 | Balamuth et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 3,989,952 | A | 11/1976 | Hohmann |
| 4,005,714 | A | 2/1977 | Hiltebrandt |
| 4,012,647 | A | 3/1977 | Balamuth et al. |
| 4,034,762 | A | 7/1977 | Cosens et al. |
| 4,057,660 | A | 11/1977 | Yoshida et al. |
| 4,058,126 | A | 11/1977 | Leveen |
| 4,074,719 | A | 2/1978 | Semm |
| 4,085,893 | A | 4/1978 | Durley, III |
| 4,156,187 | A | 5/1979 | Murry et al. |
| 4,167,944 | A | 9/1979 | Banko |
| 4,169,984 | A | 10/1979 | Parisi |
| 4,173,725 | A | 11/1979 | Asai et al. |
| 4,188,927 | A | 2/1980 | Harris |
| 4,193,009 | A | 3/1980 | Durley, III |
| 4,200,106 | A | 4/1980 | Douvas et al. |
| 4,203,430 | A | 5/1980 | Takahashi |
| 4,203,444 | A | 5/1980 | Bonnell et al. |
| 4,220,154 | A | 9/1980 | Semm |
| 4,237,441 | A | 12/1980 | van Konynenburg et al. |
| 4,281,785 | A | 8/1981 | Brooks |
| 4,300,083 | A | 11/1981 | Heiges |
| 4,302,728 | A | 11/1981 | Nakamura |
| 4,304,987 | A | 12/1981 | van Konynenburg |
| 4,306,570 | A | 12/1981 | Matthews |
| 4,314,559 | A | 2/1982 | Allen |
| 4,352,459 | A | 10/1982 | Berger et al. |
| 4,445,063 | A | 4/1984 | Smith |
| 4,452,473 | A | 6/1984 | Ruschke |
| 4,463,759 | A | 8/1984 | Garito et al. |
| 4,491,132 | A | 1/1985 | Aikins |
| 4,492,231 | A | 1/1985 | Auth |
| 4,494,759 | A | 1/1985 | Kieffer |
| 4,504,264 | A | 3/1985 | Kelman |
| 4,512,344 | A | 4/1985 | Barber |
| 4,526,571 | A | 7/1985 | Wuchinich |
| 4,535,773 | A | 8/1985 | Yoon |
| 4,541,638 | A | 9/1985 | Ogawa et al. |
| 4,545,374 | A | 10/1985 | Jacobson |
| 4,545,926 | A | 10/1985 | Fouts, Jr. et al. |
| 4,550,870 | A | 11/1985 | Krumme et al. |
| 4,553,544 | A | 11/1985 | Nomoto et al. |
| 4,562,838 | A | 1/1986 | Walker |
| 4,574,615 | A | 3/1986 | Bower et al. |
| 4,582,236 | A | 4/1986 | Hirose |
| 4,617,927 | A | 10/1986 | Manes |
| 4,633,119 | A | 12/1986 | Thompson |
| 4,633,874 | A | 1/1987 | Chow et al. |
| 4,634,420 | A | 1/1987 | Spinosa et al. |
| 4,640,279 | A | 2/1987 | Beard |
| 4,641,053 | A | 2/1987 | Takeda |
| 4,646,738 | A | 3/1987 | Trott |
| 4,646,756 | A | 3/1987 | Watmough et al. |
| 4,649,919 | A | 3/1987 | Thimsen et al. |
| 4,662,068 | A | 5/1987 | Polonsky |
| 4,663,677 | A | 5/1987 | Griffith et al. |
| 4,674,502 | A | 6/1987 | Imonti |
| 4,696,667 | A | 9/1987 | Masch |
| 4,708,127 | A | 11/1987 | Abdelghani |
| 4,712,722 | A | 12/1987 | Hood et al. |
| 4,735,603 | A | 4/1988 | Goodson et al. |
| 4,750,488 | A | 6/1988 | Wuchinich et al. |
| 4,761,871 | A | 8/1988 | O'Connor et al. |
| 4,783,997 | A | 11/1988 | Lynnworth |
| 4,808,154 | A | 2/1989 | Freeman |
| 4,819,635 | A | 4/1989 | Shapiro |
| 4,821,719 | A | 4/1989 | Fogarty |
| 4,827,911 | A | 5/1989 | Broadwin et al. |
| 4,830,462 | A | 5/1989 | Karny et al. |
| 4,832,683 | A | 5/1989 | Idemoto et al. |
| 4,836,186 | A | 6/1989 | Scholz |
| 4,838,853 | A | 6/1989 | Parisi |
| 4,844,064 | A | 7/1989 | Thimsen et al. |

(56)                 References Cited

U.S. PATENT DOCUMENTS

| | | | |
|---|---|---|---|
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,861,332 A | 8/1989 | Parisi |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,978,067 A | 12/1990 | Berger et al. |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,047,043 A | 9/1991 | Kubota et al. |
| 5,057,119 A | 10/1991 | Clark et al. |
| 5,058,570 A | 10/1991 | Idemoto et al. |
| 5,059,210 A | 10/1991 | Clark et al. |
| 5,061,269 A | 10/1991 | Muller |
| 5,084,052 A | 1/1992 | Jacobs |
| 5,088,687 A | 2/1992 | Stender |
| 5,096,532 A | 3/1992 | Neuwirth et al. |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,613 A | 10/1992 | Sawyer |
| 5,156,633 A | 10/1992 | Smith |
| 5,159,226 A | 10/1992 | Montgomery |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,209,776 A | 5/1993 | Bass et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,385 A | 9/1993 | Strukel |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,289,436 A | 2/1994 | Terhune |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| 5,306,280 A | 4/1994 | Bregen et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,327 A | 5/1994 | Bales et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,323,055 A | 6/1994 | Yamazaki |
| 5,324,297 A | 6/1994 | Hood et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,338,292 A | 8/1994 | Clement et al. |
| 5,339,723 A | 8/1994 | Huitema |
| 5,342,292 A | 8/1994 | Nita et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,354,265 A | 10/1994 | Mackool |
| 5,356,064 A | 10/1994 | Green et al. |
| 5,357,164 A | 10/1994 | Imabayashi et al. |
| 5,357,423 A | 10/1994 | Weaver et al. |
| 5,358,506 A | 10/1994 | Green et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,372,585 A | 12/1994 | Tiefenbrun et al. |
| 5,374,813 A | 12/1994 | Shipp |
| D354,564 S | 1/1995 | Medema |

(56)                References Cited

U.S. PATENT DOCUMENTS

| | | | |
|---|---|---|---|
| 5,381,067 A | 1/1995 | Greenstein et al. |
| 5,383,874 A | 1/1995 | Jackson et al. |
| 5,383,883 A | 1/1995 | Wilk et al. |
| 5,387,207 A | 2/1995 | Dyer et al. |
| 5,387,215 A | 2/1995 | Fisher |
| 5,389,098 A | 2/1995 | Tsuruta et al. |
| 5,391,144 A | 2/1995 | Sakurai et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,397,293 A | 3/1995 | Alliger et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| 5,409,453 A | 4/1995 | Lundquist et al. |
| D358,887 S | 5/1995 | Feinberg |
| 5,411,481 A | 5/1995 | Allen et al. |
| 5,413,107 A | 5/1995 | Oakley et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,496,411 A | 3/1996 | Candy |
| 5,499,992 A | 3/1996 | Meade et al. |
| 5,500,216 A | 3/1996 | Julian et al. |
| 5,501,654 A | 3/1996 | Failla et al. |
| 5,503,616 A | 4/1996 | Jones |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,273 A | 6/1996 | Manna et al. |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,575,799 A | 11/1996 | Bolanos et al. |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,578 A | 5/1997 | Tihon |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,643,301 A | 7/1997 | Mollenauer |
| 5,647,851 A | 7/1997 | Pokras |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,725,536 A | 3/1998 | Oberlin et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,735,875 A | 4/1998 | Bonutti et al. |
| 5,741,226 A | 4/1998 | Strukel et al. |
| 5,743,906 A | 4/1998 | Parins et al. |
| 5,752,973 A | 5/1998 | Kieturakis |

(56) References Cited

U.S. PATENT DOCUMENTS

| | | | |
|---|---|---|---|
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,537 A | 8/1998 | Oberlin et al. |
| 5,797,941 A | 8/1998 | Schulze et al. |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,310 A | 9/1998 | Hood |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,810,869 A | 9/1998 | Kaplan et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,820,009 A | 10/1998 | Melling et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,290 A | 12/1998 | Winston |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,363 A | 3/1999 | Urich |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,893,880 A | 4/1999 | Egan et al. |
| 5,895,412 A | 4/1999 | Tucker |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,910,150 A | 6/1999 | Saadat |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,941,887 A | 8/1999 | Steen et al. |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,001,120 A | 12/1999 | Levin |
| 6,003,517 A | 12/1999 | Sheffield et al. |
| 6,004,335 A | 12/1999 | Vaitekunas et al. |
| 6,007,552 A | 12/1999 | Fogarty et al. |
| 6,010,054 A | 1/2000 | Johnson et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,053,906 A | 4/2000 | Honda et al. |
| 6,056,735 A | 5/2000 | Okada et al. |
| 6,063,050 A | 5/2000 | Manna et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,544 A | 7/2000 | Hibner et al. |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |

(56)                    References Cited

U.S. PATENT DOCUMENTS

| | | | |
|---|---|---|---|
| 6,147,560 | A | 11/2000 | Erhage et al. |
| 6,152,902 | A | 11/2000 | Christian et al. |
| 6,152,923 | A | 11/2000 | Ryan |
| 6,154,198 | A | 11/2000 | Rosenberg |
| 6,156,029 | A | 12/2000 | Mueller |
| 6,159,160 | A | 12/2000 | Hsei et al. |
| 6,159,175 | A | 12/2000 | Strukel et al. |
| 6,162,194 | A | 12/2000 | Shipp |
| 6,162,208 | A | 12/2000 | Hipps |
| 6,165,150 | A | 12/2000 | Banko |
| 6,165,186 | A | 12/2000 | Fogarty et al. |
| 6,165,191 | A | 12/2000 | Shibata et al. |
| 6,174,309 | B1 | 1/2001 | Wrublewski et al. |
| 6,174,310 | B1 | 1/2001 | Kirwan, Jr. |
| 6,176,857 | B1 | 1/2001 | Ashley |
| 6,179,853 | B1 | 1/2001 | Sachse et al. |
| 6,183,426 | B1 | 2/2001 | Akisada et al. |
| 6,187,003 | B1 | 2/2001 | Buysse et al. |
| 6,190,386 | B1 | 2/2001 | Rydell |
| 6,193,709 | B1 | 2/2001 | Miyawaki et al. |
| 6,204,592 | B1 | 3/2001 | Hur |
| 6,205,855 | B1 | 3/2001 | Pfeiffer |
| 6,206,844 | B1 | 3/2001 | Reichel et al. |
| 6,206,876 | B1 | 3/2001 | Levine et al. |
| 6,206,877 | B1 | 3/2001 | Kese et al. |
| 6,210,337 | B1 | 4/2001 | Dunham et al. |
| 6,210,402 | B1 | 4/2001 | Olsen et al. |
| 6,210,403 | B1 | 4/2001 | Klicek |
| 6,214,023 | B1 | 4/2001 | Whipple et al. |
| 6,217,591 | B1 | 4/2001 | Egan et al. |
| 6,228,080 | B1 | 5/2001 | Gines |
| 6,228,104 | B1 | 5/2001 | Fogarty et al. |
| 6,231,565 | B1 | 5/2001 | Tovey et al. |
| 6,233,476 | B1 | 5/2001 | Strommer et al. |
| 6,238,366 | B1 | 5/2001 | Savage et al. |
| 6,241,724 | B1 | 6/2001 | Fleischman et al. |
| 6,245,065 | B1 | 6/2001 | Panescu et al. |
| 6,251,110 | B1 | 6/2001 | Wampler |
| 6,252,110 | B1 | 6/2001 | Uemura et al. |
| D444,365 | S | 7/2001 | Bass et al. |
| D445,092 | S | 7/2001 | Lee |
| D445,764 | S | 7/2001 | Lee |
| 6,254,623 | B1 | 7/2001 | Haibel, Jr. et al. |
| 6,257,241 | B1 | 7/2001 | Wampler |
| 6,258,034 | B1 | 7/2001 | Hanafy |
| 6,259,230 | B1 | 7/2001 | Chou |
| 6,267,761 | B1 | 7/2001 | Ryan |
| 6,270,471 | B1 | 8/2001 | Hechel et al. |
| 6,270,831 | B2 | 8/2001 | Kumar et al. |
| 6,273,852 | B1 | 8/2001 | Lehe et al. |
| 6,273,902 | B1 | 8/2001 | Fogarty et al. |
| 6,274,963 | B1 | 8/2001 | Estabrook et al. |
| 6,277,115 | B1 | 8/2001 | Saadat |
| 6,277,117 | B1 | 8/2001 | Tetzlaff et al. |
| 6,278,218 | B1 | 8/2001 | Madan et al. |
| 6,280,407 | B1 | 8/2001 | Manna et al. |
| 6,283,981 | B1 | 9/2001 | Beaupre |
| 6,287,344 | B1 | 9/2001 | Wampler et al. |
| 6,290,575 | B1 | 9/2001 | Shipp |
| 6,292,700 | B1 | 9/2001 | Morrison et al. |
| 6,293,954 | B1 | 9/2001 | Fogarty et al. |
| 6,299,591 | B1 | 10/2001 | Banko |
| 6,299,621 | B1 | 10/2001 | Fogarty et al. |
| 6,306,131 | B1 | 10/2001 | Hareyama et al. |
| 6,306,157 | B1 | 10/2001 | Shchervinsky |
| 6,309,400 | B2 | 10/2001 | Beaupre |
| 6,311,783 | B1 | 11/2001 | Harpell |
| 6,312,434 | B1 | 11/2001 | Sutrina et al. |
| 6,312,445 | B1 | 11/2001 | Fogarty et al. |
| 6,319,221 | B1 | 11/2001 | Savage et al. |
| 6,325,795 | B1 | 12/2001 | Lindemann et al. |
| 6,325,799 | B1 | 12/2001 | Goble |
| 6,325,811 | B1 | 12/2001 | Messerly |
| 6,328,751 | B1 | 12/2001 | Beaupre |
| 6,332,891 | B1 | 12/2001 | Himes |
| 6,333,488 | B1 | 12/2001 | Lawrence et al. |
| 6,338,657 | B1 | 1/2002 | Harper et al. |
| 6,340,352 | B1 | 1/2002 | Okada et al. |
| 6,340,878 | B1 | 1/2002 | Oglesbee |
| 6,350,269 | B1 | 2/2002 | Shipp et al. |
| 6,352,532 | B1 | 3/2002 | Kramer et al. |
| 6,358,264 | B2 | 3/2002 | Banko |
| 6,364,888 | B1 | 4/2002 | Niemeyer et al. |
| 6,379,320 | B1 | 4/2002 | Lafon et al. |
| D457,958 | S | 5/2002 | Dycus et al. |
| 6,383,194 | B1 | 5/2002 | Pothula |
| 6,384,690 | B1 | 5/2002 | Wilhelmsson et al. |
| 6,387,094 | B1 | 5/2002 | Eitenmuller |
| 6,387,109 | B1 | 5/2002 | Davison et al. |
| 6,387,112 | B1 | 5/2002 | Fogarty et al. |
| 6,388,657 | B1 | 5/2002 | Natoli |
| 6,391,026 | B1 | 5/2002 | Hung et al. |
| 6,391,042 | B1 | 5/2002 | Cimino |
| 6,398,779 | B1 | 6/2002 | Buysse et al. |
| 6,402,743 | B1 | 6/2002 | Orszulak et al. |
| 6,402,748 | B1 | 6/2002 | Schoenman et al. |
| 6,405,733 | B1 | 6/2002 | Fogarty et al. |
| 6,409,722 | B1 | 6/2002 | Hoey et al. |
| 6,409,743 | B1 | 6/2002 | Fenton, Jr. |
| H2037 | H | 7/2002 | Yates et al. |
| 6,416,469 | B1 | 7/2002 | Phung et al. |
| 6,416,486 | B1 | 7/2002 | Wampler |
| 6,416,525 | B1 | 7/2002 | Shibata |
| 6,419,675 | B1 | 7/2002 | Gallo, Sr. |
| 6,423,073 | B2 | 7/2002 | Bowman |
| 6,423,082 | B1 | 7/2002 | Houser et al. |
| 6,425,906 | B1 | 7/2002 | Young et al. |
| 6,425,907 | B1 | 7/2002 | Shibata et al. |
| 6,428,538 | B1 | 8/2002 | Blewett et al. |
| 6,428,539 | B1 | 8/2002 | Baxter et al. |
| 6,430,446 | B1 | 8/2002 | Knowlton |
| 6,432,118 | B1 | 8/2002 | Messerly |
| 6,436,114 | B1 | 8/2002 | Novak et al. |
| 6,436,115 | B1 | 8/2002 | Beaupre |
| 6,440,062 | B1 | 8/2002 | Ouchi |
| 6,443,968 | B1 | 9/2002 | Holthaus et al. |
| 6,443,969 | B1 | 9/2002 | Novak et al. |
| 6,449,006 | B1 | 9/2002 | Shipp |
| 6,454,781 | B1 | 9/2002 | Witt et al. |
| 6,454,782 | B1 | 9/2002 | Schwemberger |
| 6,458,128 | B1 | 10/2002 | Schulze |
| 6,458,130 | B1 | 10/2002 | Frazier et al. |
| 6,458,142 | B1 | 10/2002 | Faller et al. |
| 6,461,363 | B1 | 10/2002 | Gadberry et al. |
| 6,464,689 | B1 | 10/2002 | Qin et al. |
| 6,464,702 | B2 | 10/2002 | Schulze et al. |
| 6,468,286 | B2 | 10/2002 | Mastri et al. |
| 6,475,211 | B2 | 11/2002 | Chess et al. |
| 6,475,215 | B1 | 11/2002 | Tanrisever |
| 6,480,796 | B2 | 11/2002 | Wiener |
| 6,485,490 | B2 | 11/2002 | Wampler et al. |
| 6,491,690 | B1 | 12/2002 | Goble et al. |
| 6,491,701 | B2 | 12/2002 | Tierney et al. |
| 6,491,708 | B2 | 12/2002 | Madan et al. |
| 6,497,715 | B2 | 12/2002 | Satou |
| 6,498,421 | B1 | 12/2002 | Oh et al. |
| 6,500,112 | B1 | 12/2002 | Khouri |
| 6,500,176 | B1 | 12/2002 | Truckai et al. |
| 6,500,188 | B2 | 12/2002 | Harper et al. |
| 6,500,312 | B2 | 12/2002 | Wedekamp |
| 6,503,248 | B1 | 1/2003 | Levine |
| 6,506,208 | B2 | 1/2003 | Hunt et al. |
| 6,511,478 | B1 | 1/2003 | Burnside et al. |
| 6,511,480 | B1 | 1/2003 | Tetzlaff et al. |
| 6,511,493 | B1 | 1/2003 | Moutafis et al. |
| 6,514,252 | B2 | 2/2003 | Nezhat et al. |
| 6,514,267 | B2 | 2/2003 | Jewett |
| 6,517,565 | B1 | 2/2003 | Whitman et al. |
| 6,524,251 | B2 | 2/2003 | Rabiner et al. |
| 6,524,316 | B1 | 2/2003 | Nicholson et al. |
| 6,526,976 | B1 | 3/2003 | Baran |
| 6,527,736 | B1 | 3/2003 | Attinger et al. |
| 6,531,846 | B1 | 3/2003 | Smith |
| 6,533,784 | B2 | 3/2003 | Truckai et al. |

(56)                References Cited

U.S. PATENT DOCUMENTS

| 6,537,272 | B2 | 3/2003 | Christopherson et al. |
| 6,537,291 | B2 | 3/2003 | Friedman et al. |
| 6,543,452 | B1 | 4/2003 | Lavigne |
| 6,543,456 | B1 | 4/2003 | Freeman |
| 6,544,260 | B1 | 4/2003 | Markel et al. |
| 6,551,309 | B1 | 4/2003 | LePivert |
| 6,554,829 | B2 | 4/2003 | Schulze et al. |
| 6,558,376 | B2 | 5/2003 | Bishop |
| 6,561,983 | B2 | 5/2003 | Cronin et al. |
| 6,562,035 | B1 | 5/2003 | Levin |
| 6,562,037 | B2 | 5/2003 | Paton et al. |
| 6,562,059 | B2 | 5/2003 | Edwards et al. |
| 6,565,558 | B1 | 5/2003 | Lindenmeier et al. |
| 6,569,109 | B2 | 5/2003 | Sakurai et al. |
| 6,569,178 | B1 | 5/2003 | Miyawaki et al. |
| 6,572,563 | B2 | 6/2003 | Ouchi |
| 6,572,632 | B2 | 6/2003 | Zisterer et al. |
| 6,572,639 | B1 | 6/2003 | Ingle et al. |
| 6,575,929 | B2 | 6/2003 | Sussman et al. |
| 6,575,969 | B1 | 6/2003 | Rittman, III et al. |
| 6,582,427 | B1 | 6/2003 | Goble et al. |
| 6,582,451 | B1 | 6/2003 | Marucci et al. |
| 6,584,360 | B2 | 6/2003 | Francischelli et al. |
| D477,408 | S | 7/2003 | Bromley |
| 6,585,735 | B1 | 7/2003 | Frazier et al. |
| 6,588,277 | B2 | 7/2003 | Giordano et al. |
| 6,589,200 | B1 | 7/2003 | Schwemberger et al. |
| 6,589,239 | B2 | 7/2003 | Khandkar et al. |
| 6,599,288 | B2 | 7/2003 | Maguire et al. |
| 6,602,229 | B2 | 8/2003 | Coss |
| 6,602,252 | B2 | 8/2003 | Mollenauer |
| 6,607,540 | B1 | 8/2003 | Shipp |
| 6,610,059 | B1 | 8/2003 | West, Jr. |
| 6,610,060 | B2 | 8/2003 | Mulier et al. |
| 6,616,450 | B2 | 9/2003 | Mossle et al. |
| 6,619,529 | B2 | 9/2003 | Green et al. |
| 6,620,161 | B2 | 9/2003 | Schulze et al. |
| 6,622,731 | B2 | 9/2003 | Daniel et al. |
| 6,623,444 | B2 | 9/2003 | Babaev |
| 6,623,482 | B2 | 9/2003 | Pendekanti et al. |
| 6,623,500 | B1 | 9/2003 | Cook et al. |
| 6,623,501 | B2 | 9/2003 | Heller et al. |
| 6,626,848 | B2 | 9/2003 | Neuenfeldt |
| 6,626,926 | B2 | 9/2003 | Friedman et al. |
| 6,629,974 | B2 | 10/2003 | Penny et al. |
| 6,633,234 | B2 | 10/2003 | Wiener et al. |
| 6,635,057 | B2 | 10/2003 | Harano et al. |
| 6,644,532 | B2 | 11/2003 | Green et al. |
| 6,648,839 | B2 | 11/2003 | Manna et al. |
| 6,648,883 | B2 | 11/2003 | Francischelli et al. |
| 6,651,669 | B1 | 11/2003 | Burnside |
| 6,652,513 | B2 | 11/2003 | Panescu et al. |
| 6,652,539 | B2 | 11/2003 | Shipp et al. |
| 6,652,545 | B2 | 11/2003 | Shipp et al. |
| 6,656,124 | B2 | 12/2003 | Flesch et al. |
| 6,656,132 | B1 | 12/2003 | Ouchi |
| 6,656,177 | B2 | 12/2003 | Truckai et al. |
| 6,656,198 | B2 | 12/2003 | Tsonton et al. |
| 6,660,017 | B2 | 12/2003 | Beaupre |
| 6,662,127 | B2 | 12/2003 | Wiener et al. |
| 6,663,941 | B2 | 12/2003 | Brown et al. |
| 6,666,860 | B1 | 12/2003 | Takahashi |
| 6,666,875 | B1 | 12/2003 | Sakurai et al. |
| 6,669,690 | B1 | 12/2003 | Okada et al. |
| 6,669,696 | B2 | 12/2003 | Bacher et al. |
| 6,669,710 | B2 | 12/2003 | Moutafis et al. |
| 6,673,248 | B2 | 1/2004 | Chowdhury |
| 6,676,660 | B2 | 1/2004 | Wampler et al. |
| 6,678,621 | B2 | 1/2004 | Wiener et al. |
| 6,679,875 | B2 | 1/2004 | Honda et al. |
| 6,679,882 | B1 | 1/2004 | Kornerup |
| 6,679,899 | B2 | 1/2004 | Wiener et al. |
| 6,682,501 | B1 | 1/2004 | Nelson et al. |
| 6,682,544 | B2 | 1/2004 | Mastri et al. |
| 6,685,701 | B2 | 2/2004 | Orszulak et al. |
| 6,685,703 | B2 | 2/2004 | Pearson et al. |
| 6,689,086 | B1 | 2/2004 | Nita et al. |
| 6,689,145 | B2 | 2/2004 | Lee et al. |
| 6,689,146 | B1 | 2/2004 | Himes |
| 6,690,960 | B2 | 2/2004 | Chen et al. |
| 6,692,514 | B2 | 2/2004 | Fogarty et al. |
| 6,695,782 | B2 | 2/2004 | Ranucci et al. |
| 6,695,840 | B2 | 2/2004 | Schulze |
| 6,699,214 | B2 | 3/2004 | Gellman |
| 6,702,761 | B1 | 3/2004 | Damadian et al. |
| 6,702,821 | B2 | 3/2004 | Bonutti |
| 6,712,805 | B2 | 3/2004 | Weimann |
| 6,716,215 | B1 | 4/2004 | David et al. |
| 6,719,692 | B2 | 4/2004 | Kleffner et al. |
| 6,719,765 | B2 | 4/2004 | Bonutti |
| 6,719,766 | B1 | 4/2004 | Buelna et al. |
| 6,719,776 | B2 | 4/2004 | Baxter et al. |
| 6,722,552 | B2 | 4/2004 | Fenton, Jr. |
| 6,723,091 | B2 | 4/2004 | Goble et al. |
| D490,059 | S | 5/2004 | Conway et al. |
| 6,731,047 | B2 | 5/2004 | Kauf et al. |
| 6,733,498 | B2 | 5/2004 | Paton et al. |
| 6,733,506 | B1 | 5/2004 | McDevitt et al. |
| 6,736,813 | B2 | 5/2004 | Yamauchi et al. |
| 6,739,872 | B1 | 5/2004 | Turri |
| 6,740,079 | B1 | 5/2004 | Eggers et al. |
| D491,666 | S | 6/2004 | Kimmell et al. |
| 6,743,245 | B2 | 6/2004 | Lobdell |
| 6,746,284 | B1 | 6/2004 | Spink, Jr. |
| 6,746,443 | B1 | 6/2004 | Morley et al. |
| 6,752,154 | B2 | 6/2004 | Fogarty et al. |
| 6,752,815 | B2 | 6/2004 | Beaupre |
| 6,755,825 | B2 | 6/2004 | Shoenman et al. |
| 6,761,698 | B2 | 7/2004 | Shibata et al. |
| 6,762,535 | B2 | 7/2004 | Take et al. |
| 6,766,202 | B2 | 7/2004 | Underwood et al. |
| 6,770,072 | B1 | 8/2004 | Truckai et al. |
| 6,773,409 | B2 | 8/2004 | Truckai et al. |
| 6,773,434 | B2 | 8/2004 | Ciarrocca |
| 6,773,435 | B2 | 8/2004 | Schulze et al. |
| 6,773,443 | B2 | 8/2004 | Truwit et al. |
| 6,773,444 | B2 | 8/2004 | Messerly |
| 6,775,575 | B2 | 8/2004 | Bommannan et al. |
| 6,778,023 | B2 | 8/2004 | Christensen |
| 6,783,524 | B2 | 8/2004 | Anderson et al. |
| 6,786,382 | B1 | 9/2004 | Hoffman |
| 6,786,383 | B2 | 9/2004 | Stegelmann |
| 6,789,939 | B2 | 9/2004 | Schrodinger et al. |
| 6,790,173 | B2 | 9/2004 | Saadat et al. |
| 6,790,216 | B1 | 9/2004 | Ishikawa |
| 6,794,027 | B1 | 9/2004 | Araki et al. |
| 6,796,981 | B2 | 9/2004 | Wham et al. |
| D496,997 | S | 10/2004 | Dycus et al. |
| 6,800,085 | B2 | 10/2004 | Selmon et al. |
| 6,802,843 | B2 | 10/2004 | Truckai et al. |
| 6,808,525 | B2 | 10/2004 | Latterell et al. |
| 6,809,508 | B2 | 10/2004 | Donofrio |
| 6,810,281 | B2 | 10/2004 | Brock et al. |
| 6,811,842 | B1 | 11/2004 | Ehrnsperger et al. |
| 6,814,731 | B2 | 11/2004 | Swanson |
| 6,821,273 | B2 | 11/2004 | Mollenauer |
| 6,827,712 | B2 | 12/2004 | Tovey et al. |
| 6,828,712 | B2 | 12/2004 | Battaglin et al. |
| 6,832,988 | B2 | 12/2004 | Sproul |
| 6,835,082 | B2 | 12/2004 | Gonnering |
| 6,835,199 | B2 | 12/2004 | McGuckin, Jr. et al. |
| 6,840,938 | B1 | 1/2005 | Morley et al. |
| 6,849,073 | B2 | 2/2005 | Hoey et al. |
| 6,860,878 | B2 | 3/2005 | Brock |
| 6,860,880 | B2 | 3/2005 | Treat et al. |
| 6,863,676 | B2 | 3/2005 | Lee et al. |
| 6,869,439 | B2 | 3/2005 | White et al. |
| 6,875,220 | B2 | 4/2005 | Du et al. |
| 6,877,647 | B2 | 4/2005 | Green et al. |
| 6,882,439 | B2 | 4/2005 | Ishijima |
| 6,887,209 | B2 | 5/2005 | Kadziauskas et al. |
| 6,887,221 | B1 | 5/2005 | Baillargeon et al. |
| 6,887,252 | B1 | 5/2005 | Okada et al. |
| 6,893,435 | B2 | 5/2005 | Goble |

(56)        References Cited

U.S. PATENT DOCUMENTS

| | | | |
|---|---|---|---|
| 6,899,685 | B2 | 5/2005 | Kermode et al. |
| 6,905,497 | B2 | 6/2005 | Truckai et al. |
| 6,908,463 | B2 | 6/2005 | Treat et al. |
| 6,908,466 | B1 | 6/2005 | Bonutti et al. |
| 6,908,472 | B2 | 6/2005 | Wiener et al. |
| 6,913,579 | B2 | 7/2005 | Truckai et al. |
| 6,915,623 | B2 | 7/2005 | Dey et al. |
| 6,923,804 | B2 | 8/2005 | Eggers et al. |
| 6,926,712 | B2 | 8/2005 | Phan |
| 6,926,716 | B2 | 8/2005 | Baker et al. |
| 6,926,717 | B1 | 8/2005 | Garito et al. |
| 6,929,602 | B2 | 8/2005 | Hirakui et al. |
| 6,929,622 | B2 | 8/2005 | Chian |
| 6,929,632 | B2 | 8/2005 | Nita et al. |
| 6,929,644 | B2 | 8/2005 | Truckai et al. |
| 6,932,876 | B1 | 8/2005 | Statnikov |
| 6,933,656 | B2 | 8/2005 | Matsushita et al. |
| D509,589 | S | 9/2005 | Wells |
| 6,942,660 | B2 | 9/2005 | Pantera et al. |
| 6,942,676 | B2 | 9/2005 | Buelna |
| 6,942,677 | B2 | 9/2005 | Nita et al. |
| 6,945,981 | B2 | 9/2005 | Donofrio et al. |
| 6,946,779 | B2 | 9/2005 | Birgel |
| 6,948,503 | B2 | 9/2005 | Refior et al. |
| 6,953,461 | B2 | 10/2005 | McClurken et al. |
| 6,958,070 | B2 | 10/2005 | Witt et al. |
| D511,145 | S | 11/2005 | Donofrio et al. |
| 6,974,450 | B2 | 12/2005 | Weber et al. |
| 6,976,844 | B2 | 12/2005 | Hickok et al. |
| 6,976,969 | B2 | 12/2005 | Messerly |
| 6,977,495 | B2 | 12/2005 | Donofrio |
| 6,979,332 | B2 | 12/2005 | Adams |
| 6,981,628 | B2 | 1/2006 | Wales |
| 6,984,220 | B2 | 1/2006 | Wuchinich |
| 6,988,295 | B2 | 1/2006 | Tillim |
| 6,989,017 | B2 | 1/2006 | Howell et al. |
| 6,994,708 | B2 | 2/2006 | Manzo |
| 6,994,709 | B2 | 2/2006 | Iida |
| 7,000,818 | B2 | 2/2006 | Shelton, IV et al. |
| 7,001,335 | B2 | 2/2006 | Adachi et al. |
| 7,001,382 | B2 | 2/2006 | Gallo, Sr. |
| 7,002,283 | B2 | 2/2006 | Li et al. |
| 7,004,951 | B2 | 2/2006 | Gibbens, III |
| 7,011,657 | B2 | 3/2006 | Truckai et al. |
| 7,014,638 | B2 | 3/2006 | Michelson |
| 7,018,354 | B2 | 3/2006 | Tazi |
| 7,018,389 | B2 | 3/2006 | Camerlengo |
| 7,033,357 | B2 | 4/2006 | Baxter et al. |
| 7,037,306 | B2 | 5/2006 | Podany et al. |
| 7,041,083 | B2 | 5/2006 | Chu et al. |
| 7,041,088 | B2 | 5/2006 | Nawrocki et al. |
| 7,041,102 | B2 | 5/2006 | Truckai et al. |
| 7,044,949 | B2 | 5/2006 | Orszulak et al. |
| 7,052,494 | B2 | 5/2006 | Goble et al. |
| 7,052,496 | B2 | 5/2006 | Yamauchi |
| 7,055,731 | B2 | 6/2006 | Shelton, IV et al. |
| 7,062,314 | B2 | 6/2006 | Zhu et al. |
| 7,063,699 | B2 | 6/2006 | Hess et al. |
| 7,066,893 | B2 | 6/2006 | Hibner et al. |
| 7,066,895 | B2 | 6/2006 | Podany |
| 7,066,936 | B2 | 6/2006 | Ryan |
| 7,070,597 | B2 | 7/2006 | Truckai et al. |
| 7,074,218 | B2 | 7/2006 | Washington et al. |
| 7,074,219 | B2 | 7/2006 | Levine et al. |
| 7,077,036 | B1 | 7/2006 | Adams |
| 7,077,039 | B2 | 7/2006 | Gass et al. |
| 7,077,845 | B2 | 7/2006 | Hacker et al. |
| 7,077,853 | B2 | 7/2006 | Kramer et al. |
| 7,083,075 | B2 | 8/2006 | Swayze et al. |
| 7,083,618 | B2 | 8/2006 | Couture et al. |
| 7,083,619 | B2 | 8/2006 | Truckai et al. |
| 7,087,054 | B2 | 8/2006 | Truckai et al. |
| 7,090,672 | B2 | 8/2006 | Underwood et al. |
| 7,094,235 | B2 | 8/2006 | Francischelli |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,101,378 | B2 | 9/2006 | Salameh et al. |
| 7,104,834 | B2 | 9/2006 | Robinson et al. |
| 7,108,695 | B2 | 9/2006 | Witt et al. |
| 7,111,769 | B2 | 9/2006 | Wales et al. |
| 7,112,201 | B2 | 9/2006 | Truckai et al. |
| D531,311 | S | 10/2006 | Guerra et al. |
| 7,117,034 | B2 | 10/2006 | Kronberg |
| 7,118,564 | B2 | 10/2006 | Ritchie et al. |
| 7,118,570 | B2 | 10/2006 | Tetzlaff et al. |
| 7,119,516 | B2 | 10/2006 | Denning |
| 7,124,932 | B2 | 10/2006 | Isaacson et al. |
| 7,125,409 | B2 | 10/2006 | Truckai et al. |
| 7,128,720 | B2 | 10/2006 | Podany |
| 7,131,860 | B2 | 11/2006 | Sartor et al. |
| 7,131,970 | B2 | 11/2006 | Moses et al. |
| 7,131,983 | B2 | 11/2006 | Murakami |
| 7,135,018 | B2 | 11/2006 | Ryan et al. |
| 7,135,029 | B2 | 11/2006 | Makin et al. |
| 7,135,030 | B2 | 11/2006 | Schwemberger et al. |
| 7,137,963 | B2 | 11/2006 | Nita et al. |
| 7,137,980 | B2 | 11/2006 | Buysse et al. |
| 7,143,925 | B2 | 12/2006 | Shelton, IV et al. |
| 7,144,403 | B2 | 12/2006 | Booth |
| 7,147,138 | B2 | 12/2006 | Shelton, IV |
| 7,153,315 | B2 | 12/2006 | Miller |
| D536,093 | S | 1/2007 | Nakajima et al. |
| 7,156,189 | B1 | 1/2007 | Bar-Cohen et al. |
| 7,156,201 | B2 | 1/2007 | Peshkovskiy et al. |
| 7,156,846 | B2 | 1/2007 | Dycus et al. |
| 7,156,853 | B2 | 1/2007 | Muratsu |
| 7,157,058 | B2 | 1/2007 | Marhasin et al. |
| 7,159,750 | B2 | 1/2007 | Racenet et al. |
| 7,160,259 | B2 | 1/2007 | Tardy et al. |
| 7,160,296 | B2 | 1/2007 | Pearson et al. |
| 7,160,298 | B2 | 1/2007 | Lawes et al. |
| 7,160,299 | B2 | 1/2007 | Baily |
| 7,163,548 | B2 | 1/2007 | Stulen et al. |
| 7,169,144 | B2 | 1/2007 | Hoey et al. |
| 7,169,146 | B2 | 1/2007 | Truckai et al. |
| 7,169,156 | B2 | 1/2007 | Hart |
| 7,179,254 | B2 | 2/2007 | Pendekanti et al. |
| 7,179,271 | B2 | 2/2007 | Friedman et al. |
| 7,182,762 | B2 | 2/2007 | Bortkiewicz |
| 7,186,253 | B2 | 3/2007 | Truckai et al. |
| 7,189,233 | B2 | 3/2007 | Truckai et al. |
| 7,195,631 | B2 | 3/2007 | Dumbauld |
| D541,418 | S | 4/2007 | Schechter et al. |
| 7,198,635 | B2 | 4/2007 | Danek et al. |
| 7,204,820 | B2 | 4/2007 | Akahoshi |
| 7,207,471 | B2 | 4/2007 | Heinrich et al. |
| 7,207,997 | B2 | 4/2007 | Shipp et al. |
| 7,208,005 | B2 | 4/2007 | Frecker et al. |
| 7,210,881 | B2 | 5/2007 | Greenberg |
| 7,211,079 | B2 | 5/2007 | Treat |
| 7,217,128 | B2 | 5/2007 | Atkin et al. |
| 7,217,269 | B2 | 5/2007 | El-Galley et al. |
| 7,220,951 | B2 | 5/2007 | Truckai et al. |
| 7,223,229 | B2 | 5/2007 | Inman et al. |
| 7,225,964 | B2 | 6/2007 | Mastri et al. |
| 7,226,448 | B2 | 6/2007 | Bertolero et al. |
| 7,229,455 | B2 | 6/2007 | Sakurai et al. |
| 7,232,440 | B2 | 6/2007 | Dumbauld et al. |
| 7,235,071 | B2 | 6/2007 | Gonnering |
| 7,235,073 | B2 | 6/2007 | Levine et al. |
| 7,241,294 | B2 | 7/2007 | Reschke |
| 7,244,262 | B2 | 7/2007 | Wiener et al. |
| 7,251,531 | B2 | 7/2007 | Mosher et al. |
| 7,252,667 | B2 | 8/2007 | Moses et al. |
| 7,258,688 | B1 | 8/2007 | Shah et al. |
| 7,264,618 | B2 | 9/2007 | Murakami et al. |
| 7,267,677 | B2 | 9/2007 | Johnson et al. |
| 7,267,685 | B2 | 9/2007 | Butaric et al. |
| 7,269,873 | B2 | 9/2007 | Brewer et al. |
| 7,273,483 | B2 | 9/2007 | Wiener et al. |
| D552,241 | S | 10/2007 | Bromley et al. |
| 7,282,048 | B2 | 10/2007 | Goble et al. |
| 7,282,836 | B2 | 10/2007 | Kwon et al. |

(56)                  References Cited

U.S. PATENT DOCUMENTS

| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,338,463 B2 | 3/2008 | Vigil |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,533,830 B1 | 5/2009 | Rose |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,563,269 B2 | 7/2009 | Hashiguchi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,166 B2 | 8/2009 | Ethridge et al. |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,627,936 B2 | 12/2009 | Bromfield |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,763 B2 | 3/2010 | Vaezy et al. |

(56)                 References Cited

U.S. PATENT DOCUMENTS

| | | | |
|---|---|---|---|
| 7,686,770 | B2 | 3/2010 | Cohen |
| 7,686,826 | B2 | 3/2010 | Lee et al. |
| 7,688,028 | B2 | 3/2010 | Phillips et al. |
| 7,691,095 | B2 | 4/2010 | Bednarek et al. |
| 7,691,098 | B2 | 4/2010 | Wallace et al. |
| 7,696,670 | B2 | 4/2010 | Sakamoto |
| 7,699,846 | B2 | 4/2010 | Ryan |
| 7,703,459 | B2 | 4/2010 | Saadat et al. |
| 7,703,653 | B2 | 4/2010 | Shah et al. |
| 7,708,735 | B2 | 5/2010 | Chapman et al. |
| 7,708,751 | B2 | 5/2010 | Hughes et al. |
| 7,708,758 | B2 | 5/2010 | Lee et al. |
| 7,713,202 | B2 | 5/2010 | Boukhny et al. |
| 7,713,267 | B2 | 5/2010 | Pozzato |
| 7,714,481 | B2 | 5/2010 | Sakai |
| 7,717,312 | B2 | 5/2010 | Beetel |
| 7,717,914 | B2 | 5/2010 | Kimura |
| 7,717,915 | B2 | 5/2010 | Miyazawa |
| 7,721,935 | B2 | 5/2010 | Racenet et al. |
| 7,722,527 | B2 | 5/2010 | Bouchier et al. |
| 7,722,607 | B2 | 5/2010 | Dumbauld et al. |
| D618,797 | S | 6/2010 | Price et al. |
| 7,726,537 | B2 | 6/2010 | Olson et al. |
| 7,727,177 | B2 | 6/2010 | Bayat |
| 7,734,476 | B2 | 6/2010 | Wildman et al. |
| 7,738,969 | B2 | 6/2010 | Bleich |
| 7,740,594 | B2 | 6/2010 | Hibner |
| 7,749,240 | B2 | 7/2010 | Takahashi et al. |
| 7,749,273 | B2 | 7/2010 | Cauthen, III et al. |
| 7,751,115 | B2 | 7/2010 | Song |
| 7,753,904 | B2 | 7/2010 | Shelton, IV et al. |
| 7,753,908 | B2 | 7/2010 | Swanson |
| 7,762,445 | B2 | 7/2010 | Heinrich et al. |
| 7,762,979 | B2 | 7/2010 | Wuchinich |
| D621,503 | S | 8/2010 | Otten et al. |
| 7,766,210 | B2 | 8/2010 | Shelton, IV et al. |
| 7,766,693 | B2 | 8/2010 | Sartor et al. |
| 7,766,910 | B2 | 8/2010 | Hixson et al. |
| 7,770,774 | B2 | 8/2010 | Mastri et al. |
| 7,770,775 | B2 | 8/2010 | Shelton, IV et al. |
| 7,771,425 | B2 | 8/2010 | Dycus et al. |
| 7,771,444 | B2 | 8/2010 | Patel et al. |
| 7,775,972 | B2 | 8/2010 | Brock et al. |
| 7,776,036 | B2 | 8/2010 | Schechter et al. |
| 7,776,037 | B2 | 8/2010 | Odom |
| 7,778,733 | B2 | 8/2010 | Nowlin et al. |
| 7,780,054 | B2 | 8/2010 | Wales |
| 7,780,593 | B2 | 8/2010 | Ueno et al. |
| 7,780,651 | B2 | 8/2010 | Madhani et al. |
| 7,780,659 | B2 | 8/2010 | Okada et al. |
| 7,780,663 | B2 | 8/2010 | Yates et al. |
| 7,784,662 | B2 | 8/2010 | Wales et al. |
| 7,784,663 | B2 | 8/2010 | Shelton, IV |
| 7,785,324 | B2 | 8/2010 | Eberl |
| 7,789,883 | B2 | 9/2010 | Takashino et al. |
| 7,793,814 | B2 | 9/2010 | Racenet et al. |
| 7,796,969 | B2 | 9/2010 | Kelly et al. |
| 7,798,386 | B2 | 9/2010 | Schall et al. |
| 7,799,020 | B2 | 9/2010 | Shores et al. |
| 7,799,045 | B2 | 9/2010 | Masuda |
| 7,803,152 | B2 | 9/2010 | Honda et al. |
| 7,803,156 | B2 | 9/2010 | Eder et al. |
| 7,803,168 | B2 | 9/2010 | Gifford et al. |
| 7,806,891 | B2 | 10/2010 | Nowlin et al. |
| 7,810,693 | B2 | 10/2010 | Broehl et al. |
| 7,811,283 | B2 | 10/2010 | Moses et al. |
| 7,815,641 | B2 | 10/2010 | Dodde et al. |
| 7,815,658 | B2 | 10/2010 | Murakami |
| 7,819,298 | B2 | 10/2010 | Hall et al. |
| 7,819,299 | B2 | 10/2010 | Shelton, IV et al. |
| 7,819,819 | B2 | 10/2010 | Quick et al. |
| 7,819,872 | B2 | 10/2010 | Johnson et al. |
| 7,821,143 | B2 | 10/2010 | Wiener |
| D627,066 | S | 11/2010 | Romero |
| 7,824,401 | B2 | 11/2010 | Manzo et al. |
| 7,828,808 | B2 | 11/2010 | Hinman et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,834,484 | B2 | 11/2010 | Sartor |
| 7,834,521 | B2 | 11/2010 | Habu et al. |
| 7,837,699 | B2 | 11/2010 | Yamada et al. |
| 7,845,537 | B2 | 12/2010 | Shelton, IV et al. |
| 7,846,155 | B2 | 12/2010 | Houser et al. |
| 7,846,159 | B2 | 12/2010 | Morrison et al. |
| 7,846,160 | B2 | 12/2010 | Payne et al. |
| 7,846,161 | B2 | 12/2010 | Dumbauld et al. |
| 7,854,735 | B2 | 12/2010 | Houser et al. |
| D631,155 | S | 1/2011 | Peine et al. |
| 7,861,906 | B2 | 1/2011 | Doll et al. |
| 7,862,560 | B2 | 1/2011 | Marion |
| 7,867,228 | B2 | 1/2011 | Nobis et al. |
| 7,871,392 | B2 | 1/2011 | Sartor |
| 7,871,423 | B2 | 1/2011 | Livneh |
| 7,876,030 | B2 | 1/2011 | Taki et al. |
| D631,965 | S | 2/2011 | Price et al. |
| 7,878,991 | B2 | 2/2011 | Babaev |
| 7,879,033 | B2 | 2/2011 | Sartor et al. |
| 7,879,035 | B2 | 2/2011 | Garrison et al. |
| 7,879,070 | B2 | 2/2011 | Ortiz et al. |
| 7,883,465 | B2 | 2/2011 | Donofrio et al. |
| 7,883,475 | B2 | 2/2011 | Dupont et al. |
| 7,892,606 | B2 | 2/2011 | Thies et al. |
| 7,896,875 | B2 | 3/2011 | Heim et al. |
| 7,897,792 | B2 | 3/2011 | Iikura et al. |
| 7,901,400 | B2 | 3/2011 | Wham et al. |
| 7,901,423 | B2 | 3/2011 | Stulen et al. |
| 7,905,881 | B2 | 3/2011 | Masuda et al. |
| 7,909,220 | B2 | 3/2011 | Viola |
| 7,909,824 | B2 | 3/2011 | Masuda et al. |
| 7,918,848 | B2 | 4/2011 | Lau et al. |
| 7,919,184 | B2 | 4/2011 | Mohapatra et al. |
| 7,922,061 | B2 | 4/2011 | Shelton, IV et al. |
| 7,922,651 | B2 | 4/2011 | Yamada et al. |
| 7,922,716 | B2 | 4/2011 | Malecki et al. |
| 7,931,611 | B2 | 4/2011 | Novak et al. |
| 7,931,649 | B2 | 4/2011 | Couture et al. |
| D637,288 | S | 5/2011 | Houghton |
| D638,540 | S | 5/2011 | Ijiri et al. |
| 7,935,114 | B2 | 5/2011 | Takashino et al. |
| 7,936,203 | B2 | 5/2011 | Zimlich |
| 7,951,095 | B2 | 5/2011 | Makin et al. |
| 7,951,165 | B2 | 5/2011 | Golden et al. |
| 7,955,331 | B2 | 6/2011 | Truckai et al. |
| 7,959,050 | B2 | 6/2011 | Smith et al. |
| 7,959,626 | B2 | 6/2011 | Hong et al. |
| 7,963,963 | B2 | 6/2011 | Francischelli et al. |
| 7,967,602 | B2 | 6/2011 | Lindquist |
| 7,972,329 | B2 | 7/2011 | Refior et al. |
| 7,976,544 | B2 | 7/2011 | McClurken et al. |
| 7,980,443 | B2 | 7/2011 | Scheib et al. |
| 7,981,050 | B2 | 7/2011 | Ritchart et al. |
| 7,981,113 | B2 | 7/2011 | Truckai et al. |
| 7,997,278 | B2 | 8/2011 | Utley et al. |
| 7,998,157 | B2 | 8/2011 | Culp et al. |
| 8,002,732 | B2 | 8/2011 | Visconti |
| 8,006,358 | B2 | 8/2011 | Cooke et al. |
| 8,016,843 | B2 | 9/2011 | Escaf |
| 8,020,743 | B2 | 9/2011 | Shelton, IV |
| 8,025,630 | B2 | 9/2011 | Murakami et al. |
| 8,028,885 | B2 | 10/2011 | Smith et al. |
| 8,033,173 | B2 | 10/2011 | Ehlert et al. |
| 8,038,693 | B2 | 10/2011 | Allen |
| 8,048,011 | B2 | 11/2011 | Okabe |
| 8,048,070 | B2 | 11/2011 | O'Brien et al. |
| 8,052,672 | B2 | 11/2011 | Laufer et al. |
| 8,056,720 | B2 | 11/2011 | Hawkes |
| 8,057,467 | B2 | 11/2011 | Faller et al. |
| 8,057,468 | B2 | 11/2011 | Konesky |
| 8,057,498 | B2 | 11/2011 | Robertson |
| 8,058,771 | B2 | 11/2011 | Giordano et al. |
| 8,061,014 | B2 | 11/2011 | Smith et al. |
| 8,066,167 | B2 | 11/2011 | Measamer et al. |
| 8,070,036 | B1 | 12/2011 | Knodel |

(56) References Cited

U.S. PATENT DOCUMENTS

| | | | |
|---|---|---|---|
| 8,070,711 B2 | 12/2011 | Bassinger et al. | |
| 8,070,762 B2 | 12/2011 | Escudero et al. | |
| 8,075,555 B2 | 12/2011 | Truckai et al. | |
| 8,075,558 B2 | 12/2011 | Truckai et al. | |
| 8,089,197 B2 | 1/2012 | Rinner et al. | |
| 8,092,475 B2 | 1/2012 | Cotter et al. | |
| 8,097,012 B2 | 1/2012 | Kagarise | |
| 8,100,894 B2 | 1/2012 | Mucko et al. | |
| 8,105,230 B2 | 1/2012 | Honda et al. | |
| 8,105,323 B2 | 1/2012 | Buysse et al. | |
| 8,105,324 B2 | 1/2012 | Palanker et al. | |
| 8,114,104 B2 | 2/2012 | Young et al. | |
| 8,128,624 B2 | 3/2012 | Couture et al. | |
| 8,133,218 B2 | 3/2012 | Daw et al. | |
| 8,136,712 B2 | 3/2012 | Zingman | |
| 8,137,263 B2 | 3/2012 | Marescaux et al. | |
| 8,141,762 B2 | 3/2012 | Bedi et al. | |
| 8,142,421 B2 | 3/2012 | Cooper et al. | |
| 8,142,461 B2 | 3/2012 | Houser et al. | |
| 8,147,488 B2 | 4/2012 | Masuda | |
| 8,147,508 B2 | 4/2012 | Madan et al. | |
| 8,152,801 B2 | 4/2012 | Goldberg et al. | |
| 8,152,825 B2 | 4/2012 | Madan et al. | |
| 8,157,145 B2 | 4/2012 | Shelton, IV et al. | |
| 8,161,977 B2 | 4/2012 | Shelton, IV et al. | |
| 8,162,966 B2 | 4/2012 | Connor et al. | |
| 8,172,846 B2 | 5/2012 | Brunnett et al. | |
| 8,172,870 B2 | 5/2012 | Shipp | |
| 8,177,800 B2 | 5/2012 | Spitz et al. | |
| 8,182,501 B2 | 5/2012 | Houser et al. | |
| 8,182,502 B2 | 5/2012 | Stulen et al. | |
| 8,186,560 B2 | 5/2012 | Hess et al. | |
| 8,186,877 B2 | 5/2012 | Klimovitch et al. | |
| 8,187,267 B2 | 5/2012 | Pappone et al. | |
| D661,801 S | 6/2012 | Price et al. | |
| D661,802 S | 6/2012 | Price et al. | |
| D661,803 S | 6/2012 | Price et al. | |
| D661,804 S | 6/2012 | Price et al. | |
| 8,197,472 B2 | 6/2012 | Lau et al. | |
| 8,197,479 B2 | 6/2012 | Olson et al. | |
| 8,197,502 B2 | 6/2012 | Smith et al. | |
| 8,207,651 B2 | 6/2012 | Gilbert | |
| 8,210,411 B2 | 7/2012 | Yates et al. | |
| 8,221,306 B2 | 7/2012 | Okada et al. | |
| 8,221,415 B2 | 7/2012 | Francischelli | |
| 8,226,665 B2 | 7/2012 | Cohen | |
| 8,226,675 B2 | 7/2012 | Houser et al. | |
| 8,231,607 B2 | 7/2012 | Takuma | |
| 8,235,917 B2 | 8/2012 | Joseph et al. | |
| 8,236,018 B2 | 8/2012 | Yoshimine et al. | |
| 8,236,019 B2 | 8/2012 | Houser | |
| 8,236,020 B2 | 8/2012 | Smith et al. | |
| 8,241,235 B2 | 8/2012 | Kahler et al. | |
| 8,241,271 B2 | 8/2012 | Millman et al. | |
| 8,241,282 B2 | 8/2012 | Unger et al. | |
| 8,241,283 B2 | 8/2012 | Guerra et al. | |
| 8,241,284 B2 | 8/2012 | Dycus et al. | |
| 8,241,312 B2 | 8/2012 | Messerly | |
| 8,246,575 B2 | 8/2012 | Viola | |
| 8,246,615 B2 | 8/2012 | Behnke | |
| 8,246,618 B2 | 8/2012 | Bucciaglia et al. | |
| 8,246,642 B2 | 8/2012 | Houser et al. | |
| 8,251,994 B2 | 8/2012 | McKenna et al. | |
| 8,252,012 B2 | 8/2012 | Stulen | |
| 8,253,303 B2 | 8/2012 | Giordano et al. | |
| 8,257,377 B2 | 9/2012 | Wiener et al. | |
| 8,257,387 B2 | 9/2012 | Cunningham | |
| 8,262,563 B2 | 9/2012 | Bakos et al. | |
| 8,267,300 B2 | 9/2012 | Boudreaux | |
| 8,273,087 B2 | 9/2012 | Kimura et al. | |
| D669,992 S | 10/2012 | Schafer et al. | |
| D669,993 S | 10/2012 | Merchant et al. | |
| 8,277,446 B2 | 10/2012 | Heard | |
| 8,277,447 B2 | 10/2012 | Garrison et al. | |
| 8,277,471 B2 | 10/2012 | Wiener et al. | |
| 8,282,581 B2 | 10/2012 | Zhao et al. | |
| 8,282,669 B2 | 10/2012 | Gerber et al. | |
| 8,286,846 B2 | 10/2012 | Smith et al. | |
| 8,287,485 B2 | 10/2012 | Kimura et al. | |
| 8,287,528 B2 | 10/2012 | Wham et al. | |
| 8,287,532 B2 | 10/2012 | Carroll et al. | |
| 8,292,886 B2 | 10/2012 | Kerr et al. | |
| 8,292,888 B2 | 10/2012 | Whitman | |
| 8,298,223 B2 | 10/2012 | Wham et al. | |
| 8,298,225 B2 | 10/2012 | Gilbert | |
| 8,298,232 B2 | 10/2012 | Unger | |
| 8,298,233 B2 | 10/2012 | Mueller | |
| 8,303,576 B2 | 11/2012 | Brock | |
| 8,303,580 B2 | 11/2012 | Wham et al. | |
| 8,303,583 B2 | 11/2012 | Hosier et al. | |
| 8,303,613 B2 | 11/2012 | Crandall et al. | |
| 8,306,629 B2 | 11/2012 | Mioduski et al. | |
| 8,308,040 B2 | 11/2012 | Huang et al. | |
| 8,319,400 B2 | 11/2012 | Houser et al. | |
| 8,323,302 B2 | 12/2012 | Robertson et al. | |
| 8,323,310 B2 | 12/2012 | Kingsley | |
| 8,328,061 B2 | 12/2012 | Kasvikis | |
| 8,328,761 B2 | 12/2012 | Widenhouse et al. | |
| 8,328,802 B2 | 12/2012 | Deville et al. | |
| 8,328,833 B2 | 12/2012 | Cuny | |
| 8,328,834 B2 | 12/2012 | Isaacs et al. | |
| 8,333,778 B2 | 12/2012 | Smith et al. | |
| 8,333,779 B2 | 12/2012 | Smith et al. | |
| 8,334,468 B2 | 12/2012 | Palmer et al. | |
| 8,334,635 B2 | 12/2012 | Voegele et al. | |
| 8,337,407 B2 | 12/2012 | Quistgaard et al. | |
| 8,338,726 B2 | 12/2012 | Palmer et al. | |
| 8,343,146 B2 | 1/2013 | Godara et al. | |
| 8,344,596 B2 | 1/2013 | Nield et al. | |
| 8,348,880 B2 | 1/2013 | Messerly et al. | |
| 8,348,967 B2 | 1/2013 | Stulen | |
| 8,353,297 B2 | 1/2013 | Dacquay et al. | |
| 8,353,847 B2 | 1/2013 | Kuhns et al. | |
| 8,357,103 B2 | 1/2013 | Mark et al. | |
| 8,357,158 B2 | 1/2013 | McKenna et al. | |
| 8,366,727 B2 | 2/2013 | Witt et al. | |
| 8,372,064 B2 | 2/2013 | Douglass et al. | |
| 8,372,099 B2 | 2/2013 | Deville et al. | |
| 8,372,101 B2 | 2/2013 | Smith et al. | |
| 8,372,102 B2 | 2/2013 | Stulen et al. | |
| 8,374,670 B2 | 2/2013 | Selkee | |
| 8,377,044 B2 | 2/2013 | Coe et al. | |
| 8,377,059 B2 | 2/2013 | Deville et al. | |
| 8,377,085 B2 | 2/2013 | Smith et al. | |
| 8,382,748 B2 | 2/2013 | Geisel | |
| 8,382,775 B1 | 2/2013 | Bender et al. | |
| 8,382,782 B2 | 2/2013 | Robertson et al. | |
| 8,382,792 B2 | 2/2013 | Chojin | |
| 8,388,646 B2 | 3/2013 | Chojin | |
| 8,388,647 B2 | 3/2013 | Nau, Jr. et al. | |
| 8,394,096 B2 | 3/2013 | Moses et al. | |
| 8,394,115 B2 | 3/2013 | Houser et al. | |
| 8,397,971 B2 | 3/2013 | Yates et al. | |
| 8,403,926 B2 | 3/2013 | Nobis et al. | |
| 8,403,945 B2 | 3/2013 | Whitfield et al. | |
| 8,403,948 B2 | 3/2013 | Deville et al. | |
| 8,403,949 B2 | 3/2013 | Palmer et al. | |
| 8,403,950 B2 | 3/2013 | Palmer et al. | |
| 8,409,234 B2 | 4/2013 | Stahler et al. | |
| 8,414,577 B2 | 4/2013 | Boudreaux et al. | |
| 8,418,073 B2 | 4/2013 | Mohr et al. | |
| 8,418,349 B2 | 4/2013 | Smith et al. | |
| 8,419,757 B2 | 4/2013 | Smith et al. | |
| 8,419,758 B2 | 4/2013 | Smith et al. | |
| 8,419,759 B2 | 4/2013 | Dietz | |
| 8,423,182 B2 | 4/2013 | Robinson et al. | |
| 8,425,161 B2 | 4/2013 | Nagaya et al. | |
| 8,425,410 B2 | 4/2013 | Murray et al. | |
| 8,425,545 B2 | 4/2013 | Smith et al. | |
| 8,430,811 B2 | 4/2013 | Hess et al. | |
| 8,430,876 B2 | 4/2013 | Kappus et al. | |
| 8,430,897 B2 | 4/2013 | Novak et al. | |
| 8,430,898 B2 | 4/2013 | Wiener et al. | |
| 8,435,257 B2 | 5/2013 | Smith et al. | |

(56) References Cited

U.S. PATENT DOCUMENTS

| | | | |
|---|---|---|---|
| 8,435,258 | B2 | 5/2013 | Young et al. |
| 8,439,912 | B2 | 5/2013 | Cunningham et al. |
| 8,439,939 | B2 | 5/2013 | Deville et al. |
| 8,444,637 | B2 | 5/2013 | Podmore et al. |
| 8,444,662 | B2 | 5/2013 | Palmer et al. |
| 8,444,663 | B2 | 5/2013 | Houser et al. |
| 8,444,664 | B2 | 5/2013 | Balanev et al. |
| 8,453,906 | B2 | 6/2013 | Huang et al. |
| 8,454,599 | B2 | 6/2013 | Inagaki et al. |
| 8,454,639 | B2 | 6/2013 | Du et al. |
| 8,460,288 | B2 | 6/2013 | Tamai et al. |
| 8,460,292 | B2 | 6/2013 | Truckai et al. |
| 8,460,326 | B2 | 6/2013 | Houser et al. |
| 8,461,744 | B2 | 6/2013 | Wiener et al. |
| 8,469,981 | B2 | 6/2013 | Robertson et al. |
| 8,479,969 | B2 | 7/2013 | Shelton, IV |
| 8,480,703 | B2 | 7/2013 | Nicholas et al. |
| 8,484,833 | B2 | 7/2013 | Cunningham et al. |
| 8,485,413 | B2 | 7/2013 | Scheib et al. |
| 8,485,970 | B2 | 7/2013 | Widenhouse et al. |
| 8,486,057 | B2 | 7/2013 | Behnke, II |
| 8,486,096 | B2 | 7/2013 | Robertson et al. |
| 8,491,578 | B2 | 7/2013 | Manwaring et al. |
| 8,491,625 | B2 | 7/2013 | Horner |
| 8,496,682 | B2 | 7/2013 | Guerra et al. |
| D687,549 | S | 8/2013 | Johnson et al. |
| 8,506,555 | B2 | 8/2013 | Ruiz Morales |
| 8,509,318 | B2 | 8/2013 | Tailliet |
| 8,512,336 | B2 | 8/2013 | Couture |
| 8,512,359 | B2 | 8/2013 | Whitman et al. |
| 8,512,364 | B2 | 8/2013 | Kowalski et al. |
| 8,512,365 | B2 | 8/2013 | Wiener et al. |
| 8,518,067 | B2 | 8/2013 | Masuda et al. |
| 8,523,889 | B2 | 9/2013 | Stulen et al. |
| 8,528,563 | B2 | 9/2013 | Gruber |
| 8,529,437 | B2 | 9/2013 | Taylor et al. |
| 8,529,565 | B2 | 9/2013 | Masuda et al. |
| 8,531,064 | B2 | 9/2013 | Robertson et al. |
| 8,535,311 | B2 | 9/2013 | Schall |
| 8,535,340 | B2 | 9/2013 | Allen |
| 8,535,341 | B2 | 9/2013 | Allen |
| 8,540,128 | B2 | 9/2013 | Shelton, IV et al. |
| 8,546,996 | B2 | 10/2013 | Messerly et al. |
| 8,546,999 | B2 | 10/2013 | Houser et al. |
| 8,551,077 | B2 | 10/2013 | Main et al. |
| 8,551,086 | B2 | 10/2013 | Kimura et al. |
| 8,562,592 | B2 | 10/2013 | Conlon et al. |
| 8,562,598 | B2 | 10/2013 | Falkenstein et al. |
| 8,562,604 | B2 | 10/2013 | Nishimura |
| 8,568,390 | B2 | 10/2013 | Mueller |
| 8,568,400 | B2 | 10/2013 | Gilbert |
| 8,568,412 | B2 | 10/2013 | Brandt et al. |
| 8,569,997 | B2 | 10/2013 | Lee |
| 8,573,461 | B2 | 11/2013 | Shelton, IV et al. |
| 8,573,465 | B2 | 11/2013 | Shelton, IV |
| 8,574,231 | B2 | 11/2013 | Boudreaux et al. |
| 8,574,253 | B2 | 11/2013 | Gruber et al. |
| 8,579,176 | B2 | 11/2013 | Smith et al. |
| 8,579,897 | B2 | 11/2013 | Vakharia et al. |
| 8,579,928 | B2 | 11/2013 | Robertson et al. |
| 8,579,937 | B2 | 11/2013 | Gresham |
| 8,591,459 | B2 | 11/2013 | Clymer et al. |
| 8,591,506 | B2 | 11/2013 | Wham et al. |
| 8,591,536 | B2 | 11/2013 | Robertson |
| D695,407 | S | 12/2013 | Price et al. |
| D696,631 | S | 12/2013 | Price et al. |
| 8,597,193 | B2 | 12/2013 | Grunwald et al. |
| 8,602,031 | B2 | 12/2013 | Reis et al. |
| 8,602,288 | B2 | 12/2013 | Shelton, IV et al. |
| 8,608,745 | B2 | 12/2013 | Guzman et al. |
| 8,610,334 | B2 | 12/2013 | Bromfield |
| 8,613,383 | B2 | 12/2013 | Beckman et al. |
| 8,616,431 | B2 | 12/2013 | Timm et al. |
| 8,622,274 | B2 | 1/2014 | Yates et al. |
| 8,623,011 | B2 | 1/2014 | Spivey |
| 8,623,016 | B2 | 1/2014 | Fischer |
| 8,623,027 | B2 | 1/2014 | Price et al. |
| 8,623,044 | B2 | 1/2014 | Timm et al. |
| 8,628,529 | B2 | 1/2014 | Aldridge et al. |
| 8,628,534 | B2 | 1/2014 | Jones et al. |
| 8,632,461 | B2 | 1/2014 | Glossop |
| 8,636,736 | B2 | 1/2014 | Yates et al. |
| 8,638,428 | B2 | 1/2014 | Brown |
| 8,640,788 | B2 | 2/2014 | Dachs, II et al. |
| 8,641,663 | B2 | 2/2014 | Kirschenman et al. |
| 8,647,350 | B2 | 2/2014 | Mohan et al. |
| 8,650,728 | B2 | 2/2014 | Wan et al. |
| 8,651,230 | B2 | 2/2014 | Peshkovsky et al. |
| 8,652,120 | B2 | 2/2014 | Giordano et al. |
| 8,652,132 | B2 | 2/2014 | Tsuchiya et al. |
| 8,652,155 | B2 | 2/2014 | Houser et al. |
| 8,659,208 | B1 | 2/2014 | Rose et al. |
| 8,663,220 | B2 | 3/2014 | Wiener et al. |
| 8,663,222 | B2 | 3/2014 | Anderson et al. |
| 8,663,262 | B2 | 3/2014 | Smith et al. |
| 8,668,691 | B2 | 3/2014 | Heard |
| 8,668,710 | B2 | 3/2014 | Slipszenko et al. |
| 8,684,253 | B2 | 4/2014 | Giordano et al. |
| 8,685,016 | B2 | 4/2014 | Wham et al. |
| 8,685,020 | B2 | 4/2014 | Weizman et al. |
| 8,690,582 | B2 | 4/2014 | Rohrbach et al. |
| 8,691,268 | B2 | 4/2014 | Weimann |
| 8,695,866 | B2 | 4/2014 | Leimbach et al. |
| 8,696,366 | B2 | 4/2014 | Chen et al. |
| 8,696,665 | B2 | 4/2014 | Hunt et al. |
| 8,702,609 | B2 | 4/2014 | Hadjicostis |
| 8,702,704 | B2 | 4/2014 | Shelton, IV et al. |
| 8,704,425 | B2 | 4/2014 | Giordano et al. |
| 8,708,213 | B2 | 4/2014 | Shelton, IV et al. |
| 8,709,031 | B2 | 4/2014 | Stulen |
| 8,709,035 | B2 | 4/2014 | Johnson et al. |
| 8,715,270 | B2 | 5/2014 | Weitzner et al. |
| 8,715,277 | B2 | 5/2014 | Weizman |
| 8,715,306 | B2 | 5/2014 | Faller et al. |
| 8,721,640 | B2 | 5/2014 | Taylor et al. |
| 8,721,657 | B2 | 5/2014 | Kondoh et al. |
| 8,734,443 | B2 | 5/2014 | Hixson et al. |
| 8,734,476 | B2 | 5/2014 | Rhee et al. |
| 8,747,238 | B2 | 6/2014 | Shelton, IV et al. |
| 8,747,351 | B2 | 6/2014 | Schultz |
| 8,747,404 | B2 | 6/2014 | Boudreaux et al. |
| 8,749,116 | B2 | 6/2014 | Messerly et al. |
| 8,752,264 | B2 | 6/2014 | Ackley et al. |
| 8,752,749 | B2 | 6/2014 | Moore et al. |
| 8,753,338 | B2 | 6/2014 | Widenhouse et al. |
| 8,754,570 | B2 | 6/2014 | Voegele et al. |
| 8,758,342 | B2 | 6/2014 | Bales et al. |
| 8,758,352 | B2 | 6/2014 | Cooper et al. |
| 8,764,735 | B2 | 7/2014 | Coe et al. |
| 8,764,747 | B2 | 7/2014 | Cummings et al. |
| 8,767,970 | B2 | 7/2014 | Eppolito |
| 8,770,459 | B2 | 7/2014 | Racenet et al. |
| 8,771,269 | B2 | 7/2014 | Sherman et al. |
| 8,771,270 | B2 | 7/2014 | Burbank |
| 8,773,001 | B2 | 7/2014 | Wiener et al. |
| 8,777,944 | B2 | 7/2014 | Frankhouser et al. |
| 8,779,648 | B2 | 7/2014 | Giordano et al. |
| 8,783,541 | B2 | 7/2014 | Shelton, IV et al. |
| 8,784,415 | B2 | 7/2014 | Malackowski et al. |
| 8,784,418 | B2 | 7/2014 | Romero |
| 8,790,342 | B2 | 7/2014 | Stulen et al. |
| 8,795,276 | B2 | 8/2014 | Dietz et al. |
| 8,795,327 | B2 | 8/2014 | Dietz et al. |
| 8,800,838 | B2 | 8/2014 | Shelton, IV |
| 8,801,710 | B2 | 8/2014 | Ullrich et al. |
| 8,801,752 | B2 | 8/2014 | Fortier et al. |
| 8,808,319 | B2 | 8/2014 | Houser et al. |
| 8,814,856 | B2 | 8/2014 | Elmouelhi et al. |
| 8,814,870 | B2 | 8/2014 | Paraschiv et al. |
| 8,820,605 | B2 | 9/2014 | Shelton, IV |
| 8,821,388 | B2 | 9/2014 | Naito et al. |
| 8,827,992 | B2 | 9/2014 | Koss et al. |
| 8,827,995 | B2 | 9/2014 | Schaller et al. |
| 8,834,466 | B2 | 9/2014 | Cummings et al. |

(56) References Cited

U.S. PATENT DOCUMENTS

| | | | |
|---|---|---|---|
| 8,834,518 | B2 | 9/2014 | Faller et al. |
| 8,844,789 | B2 | 9/2014 | Shelton, IV et al. |
| 8,845,537 | B2 | 9/2014 | Tanaka et al. |
| 8,845,630 | B2 | 9/2014 | Mehta et al. |
| 8,848,808 | B2 | 9/2014 | Dress |
| 8,851,354 | B2 | 10/2014 | Swensgard et al. |
| 8,852,184 | B2 | 10/2014 | Kucklick |
| 8,858,547 | B2 | 10/2014 | Brogna |
| 8,862,955 | B2 | 10/2014 | Cesari |
| 8,864,709 | B2 | 10/2014 | Akagane et al. |
| 8,864,749 | B2 | 10/2014 | Okada |
| 8,864,757 | B2 | 10/2014 | Klimovitch et al. |
| 8,864,761 | B2 | 10/2014 | Johnson et al. |
| 8,870,865 | B2 | 10/2014 | Frankhouser et al. |
| 8,870,867 | B2 | 10/2014 | Walberg et al. |
| 8,882,766 | B2 | 11/2014 | Couture et al. |
| 8,882,791 | B2 | 11/2014 | Stulen |
| 8,882,792 | B2 | 11/2014 | Dietz et al. |
| 8,888,776 | B2 | 11/2014 | Dietz et al. |
| 8,888,783 | B2 | 11/2014 | Young |
| 8,888,809 | B2 | 11/2014 | Davison et al. |
| 8,899,462 | B2 | 12/2014 | Kostrzewski et al. |
| 8,900,259 | B2 | 12/2014 | Houser et al. |
| 8,906,016 | B2 | 12/2014 | Boudreaux et al. |
| 8,906,017 | B2 | 12/2014 | Rioux et al. |
| 8,911,438 | B2 | 12/2014 | Swoyer et al. |
| 8,911,460 | B2 | 12/2014 | Neurohr et al. |
| 8,920,412 | B2 | 12/2014 | Fritz et al. |
| 8,920,414 | B2 | 12/2014 | Stone et al. |
| 8,920,421 | B2 | 12/2014 | Rupp |
| 8,926,607 | B2 | 1/2015 | Norvell et al. |
| 8,926,608 | B2 | 1/2015 | Bacher et al. |
| 8,931,682 | B2 | 1/2015 | Timm et al. |
| 8,936,614 | B2 | 1/2015 | Allen, IV |
| 8,939,974 | B2 | 1/2015 | Boudreaux et al. |
| 8,951,248 | B2 | 2/2015 | Messerly et al. |
| 8,951,272 | B2 | 2/2015 | Robertson et al. |
| 8,956,349 | B2 | 2/2015 | Aldridge et al. |
| 8,961,515 | B2 | 2/2015 | Twomey et al. |
| 8,961,547 | B2 | 2/2015 | Dietz et al. |
| 8,968,283 | B2 | 3/2015 | Kharin |
| 8,968,294 | B2 | 3/2015 | Maass et al. |
| 8,968,355 | B2 | 3/2015 | Malkowski et al. |
| 8,974,447 | B2 | 3/2015 | Kimball et al. |
| 8,974,477 | B2 | 3/2015 | Yamada |
| 8,974,479 | B2 | 3/2015 | Ross et al. |
| 8,979,843 | B2 | 3/2015 | Timm et al. |
| 8,979,844 | B2 | 3/2015 | White et al. |
| 8,979,890 | B2 | 3/2015 | Boudreaux |
| 8,986,287 | B2 | 3/2015 | Park et al. |
| 8,986,302 | B2 | 3/2015 | Aldridge et al. |
| 8,989,855 | B2 | 3/2015 | Murphy et al. |
| 8,989,903 | B2 | 3/2015 | Weir et al. |
| 8,991,678 | B2 | 3/2015 | Wellman et al. |
| 8,992,422 | B2 | 3/2015 | Spivey et al. |
| 8,992,526 | B2 | 3/2015 | Brodbeck et al. |
| 9,005,199 | B2 | 4/2015 | Beckman et al. |
| 9,011,437 | B2 | 4/2015 | Woodruff et al. |
| 9,011,471 | B2 | 4/2015 | Timm et al. |
| 9,017,326 | B2 | 4/2015 | DiNardo et al. |
| 9,017,355 | B2 | 4/2015 | Smith et al. |
| 9,017,372 | B2 | 4/2015 | Artale et al. |
| 9,023,071 | B2 | 5/2015 | Miller et al. |
| 9,023,072 | B2 | 5/2015 | Young et al. |
| 9,028,397 | B2 | 5/2015 | Naito |
| 9,028,476 | B2 | 5/2015 | Bonn |
| 9,028,494 | B2 | 5/2015 | Shelton, IV et al. |
| 9,028,519 | B2 | 5/2015 | Yates et al. |
| 9,031,667 | B2 | 5/2015 | Williams |
| 9,033,973 | B2 | 5/2015 | Krapohl et al. |
| 9,035,741 | B2 | 5/2015 | Hamel et al. |
| 9,039,690 | B2 | 5/2015 | Kersten et al. |
| 9,039,695 | B2 | 5/2015 | Giordano et al. |
| 9,039,705 | B2 | 5/2015 | Takashino |
| 9,043,018 | B2 | 5/2015 | Mohr |
| 9,044,227 | B2 | 6/2015 | Shelton, IV et al. |
| 9,044,243 | B2 | 6/2015 | Johnson et al. |
| 9,044,245 | B2 | 6/2015 | Condie et al. |
| 9,044,256 | B2 | 6/2015 | Cadeddu et al. |
| 9,044,261 | B2 | 6/2015 | Houser |
| 9,050,093 | B2 | 6/2015 | Aldridge et al. |
| 9,050,098 | B2 | 6/2015 | Deville et al. |
| 9,050,124 | B2 | 6/2015 | Houser |
| 9,055,961 | B2 | 6/2015 | Manzo et al. |
| 9,059,547 | B2 | 6/2015 | McLawhorn |
| 9,060,770 | B2 | 6/2015 | Shelton, IV et al. |
| 9,060,775 | B2 | 6/2015 | Wiener et al. |
| 9,060,776 | B2 | 6/2015 | Yates et al. |
| 9,063,049 | B2 | 6/2015 | Beach et al. |
| 9,066,723 | B2 | 6/2015 | Beller et al. |
| 9,066,747 | B2 | 6/2015 | Robertson |
| 9,072,535 | B2 | 7/2015 | Shelton, IV et al. |
| 9,072,536 | B2 | 7/2015 | Shelton, IV et al. |
| 9,072,539 | B2 | 7/2015 | Messerly et al. |
| 9,084,624 | B2 | 7/2015 | Larkin et al. |
| 9,084,878 | B2 | 7/2015 | Kawaguchi et al. |
| 9,089,327 | B2 | 7/2015 | Worrell et al. |
| 9,089,360 | B2 | 7/2015 | Messerly et al. |
| 9,095,362 | B2 | 8/2015 | Dachs, II et al. |
| 9,095,367 | B2 | 8/2015 | Olson et al. |
| 9,101,385 | B2 | 8/2015 | Shelton, IV et al. |
| 9,107,684 | B2 | 8/2015 | Ma |
| 9,107,689 | B2 | 8/2015 | Robertson et al. |
| 9,107,690 | B2 | 8/2015 | Bales, Jr. et al. |
| 9,113,900 | B2 | 8/2015 | Buysse et al. |
| 9,113,940 | B2 | 8/2015 | Twomey |
| 9,114,245 | B2 | 8/2015 | Dietz et al. |
| 9,119,657 | B2 | 9/2015 | Shelton, IV et al. |
| 9,119,957 | B2 | 9/2015 | Gantz et al. |
| 9,125,662 | B2 | 9/2015 | Shelton, IV |
| 9,125,667 | B2 | 9/2015 | Stone et al. |
| 9,125,722 | B2 | 9/2015 | Schwartz |
| 9,147,965 | B2 | 9/2015 | Lee |
| 9,149,324 | B2 | 10/2015 | Huang et al. |
| 9,149,325 | B2 | 10/2015 | Worrell et al. |
| 9,161,803 | B2 | 10/2015 | Yates et al. |
| 9,168,054 | B2 | 10/2015 | Turner et al. |
| 9,168,055 | B2 | 10/2015 | Houser et al. |
| 9,168,085 | B2 | 10/2015 | Juzkiw et al. |
| 9,168,089 | B2 | 10/2015 | Buysse et al. |
| 9,168,090 | B2 | 10/2015 | Strobl et al. |
| 9,173,656 | B2 | 11/2015 | Schurr et al. |
| 9,179,912 | B2 | 11/2015 | Yates et al. |
| 9,186,199 | B2 | 11/2015 | Strauss et al. |
| 9,186,204 | B2 | 11/2015 | Nishimura et al. |
| 9,192,380 | B2 | 11/2015 | (Tarinelli) Racenet et al. |
| 9,192,431 | B2 | 11/2015 | Woodruff et al. |
| 9,198,714 | B2 | 12/2015 | Worrell et al. |
| 9,198,715 | B2 | 12/2015 | Livneh |
| 9,204,879 | B2 | 12/2015 | Shelton, IV |
| 9,204,891 | B2 | 12/2015 | Weitzman |
| 9,204,918 | B2 | 12/2015 | Germain et al. |
| 9,204,923 | B2 | 12/2015 | Manzo et al. |
| 9,216,050 | B2 | 12/2015 | Condie et al. |
| 9,216,062 | B2 | 12/2015 | Duque et al. |
| 9,220,483 | B2 | 12/2015 | Frankhouser et al. |
| 9,220,527 | B2 | 12/2015 | Houser et al. |
| 9,220,559 | B2 | 12/2015 | Worrell et al. |
| 9,226,750 | B2 | 1/2016 | Weir et al. |
| 9,226,751 | B2 | 1/2016 | Shelton, IV et al. |
| 9,226,766 | B2 | 1/2016 | Aldridge et al. |
| 9,226,767 | B2 | 1/2016 | Stulen et al. |
| 9,232,979 | B2 | 1/2016 | Parihar et al. |
| 9,237,891 | B2 | 1/2016 | Shelton, IV |
| 9,237,921 | B2 | 1/2016 | Messerly et al. |
| 9,237,923 | B2 | 1/2016 | Worrell et al. |
| 9,241,060 | B1 | 1/2016 | Fujisaki |
| 9,241,692 | B2 | 1/2016 | Gunday et al. |
| 9,241,728 | B2 | 1/2016 | Price et al. |
| 9,241,730 | B2 | 1/2016 | Babaev |
| 9,241,731 | B2 | 1/2016 | Boudreaux et al. |
| 9,241,768 | B2 | 1/2016 | Sandhu et al. |
| D749,730 | S | 2/2016 | Dietz et al. |
| 9,247,953 | B2 | 2/2016 | Palmer et al. |

(56) References Cited

U.S. PATENT DOCUMENTS

| | | |
|---|---|---|
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,301,772 B2 | 4/2016 | Kimball et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,235 B2 | 11/2016 | Harrington et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |

(56)                References Cited

U.S. PATENT DOCUMENTS

| | | |
|---|---|---|
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,363,058 B2 | 7/2019 | Roberson et al. |
| 10,368,892 B2 | 8/2019 | Stulen et al. |
| 10,368,894 B2 | 8/2019 | Madan et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 10,512,795 B2 | 12/2019 | Voegele et al. |
| 10,517,627 B2 | 12/2019 | Timm et al. |
| 10,524,854 B2 | 1/2020 | Woodruff et al. |
| 10,531,910 B2 | 1/2020 | Houser et al. |
| 10,537,351 B2 | 1/2020 | Shelton, IV et al. |
| 10,537,352 B2 | 1/2020 | Faller et al. |
| 10,537,667 B2 | 1/2020 | Anim |
| 10,543,008 B2 | 1/2020 | Vakharia et al. |
| 10,555,750 B2 | 2/2020 | Conlon et al. |
| 10,555,769 B2 | 2/2020 | Worrell et al. |
| 10,561,436 B2 | 2/2020 | Asher et al. |
| 10,575,892 B2 | 3/2020 | Danziger et al. |
| 10,595,929 B2 | 3/2020 | Boudreaux et al. |
| 10,595,930 B2 | 3/2020 | Scheib et al. |
| 10,603,064 B2 | 3/2020 | Zhang |
| 10,610,286 B2 | 4/2020 | Wiener et al. |
| 10,624,665 B2 | 4/2020 | Noui et al. |
| 10,624,691 B2 | 4/2020 | Wiener et al. |
| 10,639,092 B2 | 5/2020 | Corbett et al. |
| 10,646,267 B2 | 5/2020 | Ding |
| 10,677,764 B2 | 6/2020 | Ross et al. |
| 10,687,884 B2 | 6/2020 | Wiener et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,261 B2 | 7/2020 | Houser et al. |
| 10,729,458 B2 | 8/2020 | Stoddard et al. |
| 10,736,649 B2 | 8/2020 | Messerly et al. |
| 10,736,685 B2 | 8/2020 | Wiener et al. |
| 10,751,108 B2 | 8/2020 | Yates et al. |
| 10,758,294 B2 | 9/2020 | Jones |
| 10,779,845 B2 | 9/2020 | Timm et al. |
| 10,779,847 B2 | 9/2020 | Messerly et al. |
| 10,779,848 B2 | 9/2020 | Houser |
| 10,779,849 B2 | 9/2020 | Shelton, IV et al. |
| 10,779,879 B2 | 9/2020 | Yates et al. |
| 10,820,920 B2 | 11/2020 | Scoggins et al. |
| 10,820,938 B2 | 11/2020 | Fischer et al. |
| 10,828,056 B2 | 11/2020 | Messerly et al. |
| 10,828,057 B2 | 11/2020 | Neurohr et al. |
| 10,828,058 B2 | 11/2020 | Shelton, IV et al. |
| 10,828,059 B2 | 11/2020 | Price et al. |
| 10,835,307 B2 | 11/2020 | Shelton, IV et al. |
| 10,835,768 B2 | 11/2020 | Robertson et al. |
| 10,842,522 B2 | 11/2020 | Messerly et al. |
| 10,842,523 B2 | 11/2020 | Shelton, IV et al. |
| 10,842,580 B2 | 11/2020 | Gee et al. |
| 10,856,896 B2 | 12/2020 | Eichmann et al. |
| 10,874,418 B2 | 12/2020 | Houser et al. |
| 10,881,449 B2 | 1/2021 | Boudreaux et al. |
| 10,881,451 B2 | 1/2021 | Worrell et al. |
| 10,888,347 B2 | 1/2021 | Witt et al. |
| 10,893,883 B2 | 1/2021 | Dannaher |
| 10,912,603 B2 | 2/2021 | Boudreaux et al. |
| 10,952,759 B2 | 3/2021 | Messerly et al. |
| 10,959,769 B2 | 3/2021 | Mumaw et al. |
| 10,966,744 B2 | 4/2021 | Rhee et al. |
| 10,987,123 B2 | 4/2021 | Weir et al. |
| 11,000,707 B2 | 5/2021 | Voegele et al. |
| 11,006,971 B2 | 5/2021 | Faller et al. |
| 11,020,140 B2 | 6/2021 | Gee et al. |
| 11,033,292 B2 | 6/2021 | Green et al. |
| 11,033,322 B2 | 6/2021 | Wiener et al. |
| D924,400 S | 7/2021 | Kimball |
| 11,051,840 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,129,670 B2 | 9/2021 | Shelton, IV et al. |
| 11,134,978 B2 | 10/2021 | Shelton, IV et al. |
| 11,141,213 B2 | 10/2021 | Yates et al. |

(56)                References Cited

U.S. PATENT DOCUMENTS

| | | |
|---|---|---|
| 11,179,582 B2 | 11/2021 | Voegele et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,253,288 B2 | 2/2022 | Robertson |
| 11,266,433 B2 | 3/2022 | Robertson |
| 11,272,952 B2 | 3/2022 | Messerly et al. |
| 11,324,527 B2 | 5/2022 | Aldridge et al. |
| 11,350,959 B2 | 6/2022 | Messerly et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0032002 A1 | 10/2001 | McClurken et al. |
| 2001/0039419 A1 | 11/2001 | Francischelli et al. |
| 2002/0002377 A1 | 1/2002 | Cimino |
| 2002/0002378 A1 | 1/2002 | Messerly |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0026184 A1* | 2/2002 | Witt ............... A61B 17/320092 606/40 |
| 2002/0029054 A1 | 3/2002 | Rabiner et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0099373 A1 | 7/2002 | Schulze et al. |
| 2002/0107446 A1 | 8/2002 | Rabiner et al. |
| 2002/0107517 A1 | 8/2002 | Witt et al. |
| 2002/0120266 A1 | 8/2002 | Truckai et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0120306 A1 | 6/2003 | Burbank et al. |
| 2003/0130675 A1 | 7/2003 | Kasahara et al. |
| 2003/0130693 A1 | 7/2003 | Levin et al. |
| 2003/0139741 A1 | 7/2003 | Goble et al. |
| 2003/0144652 A1 | 7/2003 | Baker et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0195496 A1 | 10/2003 | Maguire et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212391 A1 | 11/2003 | Fenton et al. |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0039242 A1 | 2/2004 | Tolkoff et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0147946 A1 | 7/2004 | Mastri et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0199194 A1 | 10/2004 | Witt et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0085728 A1 | 4/2005 | Fukuda |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0228425 A1 | 10/2005 | Boukhny et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0025802 A1 | 2/2006 | Sowers |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0095046 A1 | 5/2006 | Trieu et al. |
| 2006/0100652 A1 | 5/2006 | Beaupre |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0241580 A1 | 10/2006 | Mittelstein et al. |
| 2006/0247558 A1 | 11/2006 | Yamada |
| 2006/0253050 A1 | 11/2006 | Yoshimine et al. |

(56)                    References Cited

U.S. PATENT DOCUMENTS

| 2006/0257819 A1 | 11/2006 | Johnson |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0198005 A1 | 8/2007 | Ichihashi et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0276419 A1 | 11/2007 | Rosenthal |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097281 A1 | 4/2008 | Zusman et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0294051 A1 | 11/2008 | Koshigoe et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0099582 A1* | 4/2009 | Isaacs ................ A61B 17/3201 |
| | | 606/169 |
| 2009/0118751 A1 | 5/2009 | Wiener et al. |
| 2009/0143678 A1 | 6/2009 | Keast et al. |
| 2009/0143796 A1* | 6/2009 | Stulen ...................... B06B 3/00 |
| | | 606/169 |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042126 A1 | 2/2010 | Houser et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228191 A1 | 9/2010 | Alvarez et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0312186 A1 | 12/2010 | Suchdev et al. |
| 2010/0331742 A1 | 12/2010 | Masuda |
| 2010/0331873 A1* | 12/2010 | Dannaher .......... A61B 17/2816 |
| | | 606/169 |
| 2011/0004233 A1 | 1/2011 | Muir et al. |
| 2011/0028964 A1 | 2/2011 | Edwards |

(56)  References Cited

U.S. PATENT DOCUMENTS

| | | |
|---|---|---|
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0291526 A1 | 12/2011 | Abramovich et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0078249 A1 | 3/2012 | Eichmann et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116363 A1* | 5/2012 | Houser ................. A61B 34/25 |
| | | 606/1 |
| 2012/0136279 A1 | 5/2012 | Tanaka et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2012/0330338 A1 | 12/2012 | Messerly |
| 2013/0023925 A1 | 1/2013 | Mueller |
| 2013/0072948 A1 | 3/2013 | States, III et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0197511 A1* | 8/2013 | Balanev ......... A61B 17/320092 |
| | | 606/41 |
| 2013/0231691 A1 | 9/2013 | Houser |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2013/0331873 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0207163 A1 | 7/2014 | Eichmann et al. |
| 2014/0276963 A1 | 9/2014 | Ranucci et al. |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0083774 A1 | 3/2015 | Measamer et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0165240 A1* | 6/2015 | Stoddard ........ A61B 17/320092 |
| | | 606/171 |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0114355 A1 | 4/2016 | Sakai et al. |
| 2016/0128769 A1 | 5/2016 | Rontal et al. |
| 2016/0175029 A1 | 6/2016 | Witt et al. |
| 2016/0206342 A1 | 7/2016 | Robertson et al. |
| 2016/0240768 A1 | 8/2016 | Fujii et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2017/0027624 A1 | 2/2017 | Wilson et al. |
| 2017/0036044 A1 | 2/2017 | Ito |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0189095 A1 | 7/2017 | Danziger et al. |
| 2017/0202595 A1 | 7/2017 | Shelton, IV |
| 2017/0205234 A1 | 7/2017 | Honda |
| 2018/0125523 A1 | 5/2018 | Johnson |
| 2019/0053822 A1 | 2/2019 | Robertson et al. |
| 2019/0239919 A1 | 8/2019 | Witt et al. |
| 2019/0350615 A1 | 11/2019 | Messerly et al. |
| 2019/0380733 A1 | 12/2019 | Stulen et al. |
| 2020/0008857 A1 | 1/2020 | Conlon et al. |
| 2020/0015798 A1 | 1/2020 | Wiener et al. |
| 2020/0046401 A1 | 2/2020 | Witt et al. |
| 2020/0054386 A1 | 2/2020 | Houser et al. |
| 2020/0054899 A1 | 2/2020 | Wiener et al. |
| 2020/0085466 A1 | 3/2020 | Faller et al. |
| 2020/0323551 A1 | 10/2020 | Faller et al. |
| 2021/0038248 A1 | 2/2021 | Houser |
| 2021/0121197 A1 | 4/2021 | Houser et al. |
| 2021/0145531 A1 | 5/2021 | Gee et al. |
| 2021/0236157 A1 | 8/2021 | Rhee et al. |
| 2021/0315605 A1 | 10/2021 | Gee et al. |
| 2021/0378700 A1 | 12/2021 | Houser |
| 2022/0257276 A1 | 8/2022 | Robertson |
| 2022/0346824 A1 | 11/2022 | Messerly et al. |
| 2022/0387068 A1 | 12/2022 | Witt et al. |
| 2023/0191161 A1 | 6/2023 | Wiener et al. |

FOREIGN PATENT DOCUMENTS

| | | |
|---|---|---|
| CA | 2214413 A1 | 9/1996 |
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 101766869 A | 7/2010 |
| CN | 202027624 U | 11/2011 |
| CN | 102335778 A | 2/2012 |
| CN | 103417267 A | 12/2013 |
| CN | 103668171 A | 3/2014 |
| CN | 103921215 A | 7/2014 |
| CN | 106077718 A | 11/2016 |
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1543854 A1 | 6/2005 |
| EP | 1698289 A2 | 9/2006 |

(56)          References Cited

FOREIGN PATENT DOCUMENTS

| | | | |
|---|---|---|---|
| EP | 1862133 | A1 | 12/2007 |
| EP | 1972264 | A1 | 9/2008 |
| EP | 2060238 | A1 | 5/2009 |
| EP | 1747761 | B1 | 10/2009 |
| EP | 2131760 | A1 | 12/2009 |
| EP | 1214913 | B1 | 7/2010 |
| EP | 1946708 | B1 | 6/2011 |
| EP | 1767164 | B1 | 1/2013 |
| EP | 2578172 | A2 | 4/2013 |
| EP | 2510891 | B1 | 6/2016 |
| FR | 2454351 | A1 | 11/1980 |
| FR | 2964554 | A1 | 3/2012 |
| GB | 2032221 | A | 4/1980 |
| GB | 2317566 | A | 4/1998 |
| GB | 2318298 | A | 4/1998 |
| GB | 2425480 | A | 11/2006 |
| JP | S50100891 | A | 8/1975 |
| JP | S5968513 | U | 5/1984 |
| JP | S59141938 | A | 8/1984 |
| JP | S62213746 | A | 9/1987 |
| JP | S62221343 | A | 9/1987 |
| JP | S62227343 | A | 10/1987 |
| JP | S62292153 | A | 12/1987 |
| JP | S62292154 | A | 12/1987 |
| JP | S63109386 | A | 5/1988 |
| JP | S63315049 | A | 12/1988 |
| JP | H01151452 | A | 6/1989 |
| JP | H01198540 | A | 8/1989 |
| JP | H0271510 | U | 5/1990 |
| JP | H02286149 | A | 11/1990 |
| JP | H02292193 | A | 12/1990 |
| JP | H0337061 | A | 2/1991 |
| JP | H0425707 | U | 2/1992 |
| JP | H0464351 | A | 2/1992 |
| JP | H0430508 | U | 3/1992 |
| JP | H04152942 | A | 5/1992 |
| JP | H04161078 | A | 6/1992 |
| JP | H0595955 | A | 4/1993 |
| JP | H05115490 | A | 5/1993 |
| JP | H0647048 | A | 2/1994 |
| JP | H0670938 | A | 3/1994 |
| JP | H06104503 | A | 4/1994 |
| JP | H07185457 | A | 7/1995 |
| JP | H07299415 | A | 11/1995 |
| JP | H0824266 | A | 1/1996 |
| JP | H08229050 | A | 9/1996 |
| JP | H08275950 | A | 10/1996 |
| JP | H08275951 | A | 10/1996 |
| JP | H08299351 | A | 11/1996 |
| JP | H08336545 | A | 12/1996 |
| JP | H09135553 | A | 5/1997 |
| JP | H09140722 | A | 6/1997 |
| JP | H105236 | A | 1/1998 |
| JP | H105237 | A | 1/1998 |
| JP | H10295700 | A | 11/1998 |
| JP | H11128238 | A | 5/1999 |
| JP | 2000139943 | A | 5/2000 |
| JP | 2000210296 | A | 8/2000 |
| JP | 2000210299 | A | 8/2000 |
| JP | 2000271145 | A | 10/2000 |
| JP | 2000287987 | A | 10/2000 |
| JP | 2000312682 | A | 11/2000 |
| JP | 2001029353 | A | 2/2001 |
| JP | 2001057985 | A | 3/2001 |
| JP | 2001170066 | A | 6/2001 |
| JP | 2001198137 | A | 7/2001 |
| JP | 2002035002 | A | 2/2002 |
| JP | 2002186901 | A | 7/2002 |
| JP | 2002233533 | A | 8/2002 |
| JP | 2002263579 | A | 9/2002 |
| JP | 2002330977 | A | 11/2002 |
| JP | 2003000612 | A | 1/2003 |
| JP | 2003010201 | A | 1/2003 |
| JP | 2003116870 | A | 4/2003 |
| JP | 2003126104 | A | 5/2003 |
| JP | 2003126110 | A | 5/2003 |
| JP | 2003153919 | A | 5/2003 |
| JP | 2003230567 | A | 8/2003 |
| JP | 2003339730 | A | 12/2003 |
| JP | 2004129871 | A | 4/2004 |
| JP | 2004147701 | A | 5/2004 |
| JP | 2004209043 | A | 7/2004 |
| JP | 2005027026 | A | 1/2005 |
| JP | 2005074088 | A | 3/2005 |
| JP | 2005094552 | A | 4/2005 |
| JP | 2005253674 | A | 9/2005 |
| JP | 2006217716 | A | 8/2006 |
| JP | 2006288431 | A | 10/2006 |
| JP | 3841627 | B2 | 11/2006 |
| JP | 2007177931 | A | 7/2007 |
| JP | D339835 | S | 8/2008 |
| JP | 2009071439 | A | 4/2009 |
| JP | 2009082904 | A | 4/2009 |
| JP | 2009236177 | A | 10/2009 |
| JP | 2009297352 | A | 12/2009 |
| JP | 2010009686 | A | 1/2010 |
| JP | 2010121865 | A | 6/2010 |
| JP | 2011160586 | A | 8/2011 |
| JP | 2012235658 | A | 11/2012 |
| JP | 2014121340 | A | 7/2014 |
| JP | 2015123519 | A | 7/2015 |
| JP | 2015529140 | A | 10/2015 |
| JP | 2016022136 | A | 2/2016 |
| KR | 100789356 | B1 | 12/2007 |
| RU | 2154437 | C1 | 8/2000 |
| RU | 22035 | U1 | 3/2002 |
| RU | 2201169 | C2 | 3/2003 |
| RU | 2405603 | C1 | 12/2010 |
| SU | 850068 | A1 | 7/1981 |
| WO | WO-8103272 | A1 | 11/1981 |
| WO | WO-9308757 | A1 | 5/1993 |
| WO | WO-9314708 | A1 | 8/1993 |
| WO | WO-9421183 | A1 | 9/1994 |
| WO | WO-9424949 | A1 | 11/1994 |
| WO | WO-9639086 | A1 | 12/1996 |
| WO | WO-9800069 | A1 | 1/1998 |
| WO | WO-9805437 | A1 | 2/1998 |
| WO | WO-9816157 | A1 | 4/1998 |
| WO | WO-9920213 | A1 | 4/1999 |
| WO | WO-9923960 | A1 | 5/1999 |
| WO | WO-0024322 | A1 | 5/2000 |
| WO | WO-0024330 | A1 | 5/2000 |
| WO | WO-0064358 | A2 | 11/2000 |
| WO | WO-0128444 | A1 | 4/2001 |
| WO | WO-0132087 | A1 | 5/2001 |
| WO | WO-0167970 | A1 | 9/2001 |
| WO | WO-0170112 | A1 | 9/2001 |
| WO | WO-0195810 | A2 | 12/2001 |
| WO | WO-02076685 | A1 | 10/2002 |
| WO | WO-02080799 | A1 | 10/2002 |
| WO | WO-2004037095 | A2 | 5/2004 |
| WO | WO-2004078051 | A2 | 9/2004 |
| WO | WO-2004098426 | A1 | 11/2004 |
| WO | WO-2005084250 | A2 | 9/2005 |
| WO | WO-2007008710 | A2 | 1/2007 |
| WO | WO-2008118709 | A1 | 10/2008 |
| WO | WO-2008130793 | A1 | 10/2008 |
| WO | WO-2008154338 | A1 | 12/2008 |
| WO | WO-2010104755 | A1 | 9/2010 |
| WO | WO-2011008672 | A2 | 1/2011 |
| WO | WO-2011052939 | A2 | 5/2011 |
| WO | WO-2011060031 | A1 | 5/2011 |
| WO | WO-2012044606 | A2 | 4/2012 |
| WO | WO-2012066983 | A1 | 5/2012 |
| WO | WO-2013048963 | A2 | 4/2013 |

OTHER PUBLICATIONS

Jang, J. et al. "Neuro-fuzzy and Soft Computing." Prentice Hall, 1997, pp. 13-89, 199-293, 335-393, 453-496, 535-549.

Leonard I. Malis, M.D., "The Value of Irrigation During Bipolar Coagulation," 1989.

(56)                    References Cited

OTHER PUBLICATIONS http://www.4-traders.com/JOHNSON-JOHNSON-4832/news/Johnson-Johnson-Ethicon-E . . . .

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Lacourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

Gerhard, Glen C., "Surgical Electrotechnology: Quo Vadis?," IEEE Transactions on Biomedical Engineering, vol. BME-31, No. 12, pp. 787-792, Dec. 1984.

Fowler, K.R., "A Programmable, Arbitrary Waveform Electrosurgical Device," IEEE Engineering in Medicine and Biology Society 10th Annual International Conference, pp. 1324, 1325 (1988).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Technology Overview, printed from www.harmonicscalpel.com, Internet site, website accessed on Jun. 13, 2007, (3 pages).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Weir, C.E., "Rate of shrinkage of tendon collagen - heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Henriques. F.C., "Studies in thermal injury V. The predictability and the significance of thermally induced rate processes leading to irreversible epidermal injury." Archives of Pathology, 434, pp. 489-502 (1947).

Chen et al., "Heat-induced changes in the mechanics of a collagenous tissue: pseudoelastic behavior at 37° C.," Journal of Biomechanics, 31, pp. 211-216 (1998).

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Covidien 501 (k) Summary Sonicision, dated Feb. 24, 2011 (7 pages).

http://www.valleylab.com/product/es/generators/index.html.

http://www.megadyne.com/es_generator.php.

http://www.medicalexpo.com/medical-manufacturer/electrosurgical-generator-6951.html.

http:/www.ethicon.com/gb-en/healthcare-professionals/products/energy-devices/capital/ge . . . .

http://www.dotmed.com/listing/electrosurical-unit/ethicon/ultracision-g110-/1466724.

http://www.apicalinstr.com/generators.htm.

Walsh, S. J., White, R. G., "Vibrational Power Transmission in Curved Beams," Journal of Sound and Vibration, 233(3), 455-488 (2000).

Morley, L. S. D., "Elastic Waves in a Naturally Curved Rod," Quarterly Journal of Mechanics and Applied Mathematics, 14: 155-172 (1961).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Graff, K.F., "Elastic Wave Propagation in a Curved Sonic Transmission Line," IEEE Transactions on Sonics and Ultrasonics, SU-17(1), 1-6 (1970).

Campbell et al., "Thermal Imaging in Surgery," p. 19-3, in Medical Infrared Imaging, N. A. Diakides and J. D. Bronzino, Eds. (2008).

F. A. Duck, "Optical Properties of Tissue Including Ultraviolet and Infrared Radiation," pp. 43-71 in Physical Properties of Tissue (1990).

Lim et al., "A Review of Mechanism Used in Laparoscopic Surgical Instruments," Mechanism and Machine Theory, vol. 38, pp. 1133-1147, (2003).

AST Products, Inc., "Principles of Video Contact Angle Analysis," 20 pages, (2006).

Wall et al., "Thermal modification of collagen," J Shoulder Elbow Surg, No. 8, pp. 339-344 (Jul/Aug. 1999).

Covidien Brochure, [Value Analysis Brief], LigaSure Advance™ Pistol Grip, dated Rev. Apr. 2010 (7 pages).

Kurt Gieck & Reiner Gieck, Engineering Formulas § Z.7 (7th ed. 1997).

Covidien Brochure, The LigaSure Precise™ Instrument, dated Mar. 2011 (2 pages).

Covidien Brochure, The LigaSure™ 5 mm Blunt Tip Sealer/Divider Family, dated Apr. 2013 (2 pages).

National Semiconductors Temperature Sensor Handbook—http://www.national.com/appinfo/tempsensors/files/temphb.pdf; accessed online: Apr. 1, 2011.

Sullivan, "Optimal Choice for Number of Strands in a Litz-Wire Transformer Winding," IEEE Transactions on Power Electronics, vol. 14, No. 2, Mar. 1999, pp. 283-291.

Douglas, S.C. "Introduction to Adaptive Filter". Digital Signal Processing Handbook. Ed. Vijay K. Madisetti and Douglas B. Williams. Boca Raton: CRC Press LLC, 1999.

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

Covidien Brochure, LigaSure Atlas™ Hand Switching Instruments, dated Dec. 2008 (2 pages).

Covidien Brochure, LigaSure Impact™ Instrument LF4318, dated Feb. 2013 (3 pages).

Wright, et al., "Time-Temperature Equivalence of Heat-Induced Changes in Cells and Proteins," Feb. 1998. ASME Journal of Biomechanical Engineering, vol. 120, pp. 22-26.

Humphrey, J.D., "Continuum Thermomechanics and the Clinical Treatment of Disease and Injury," Appl. Mech. Rev., vol. 56, No. 2 pp. 231-260 (Mar. 2003).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Moran et al., "Thermally Induced Shrinkage of Joint Capsule," Clinical Orthopaedics and Related Research, No. 281, pp. 248-255 (Dec. 2000).

Lee et al., "A multi-sample denaturation temperature tester for collagenous biomaterials," Med. Eng. Phy., vol. 17, No. 2, pp. 115-121 (Mar. 1995).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

(56)　　　　　References Cited

OTHER PUBLICATIONS

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Chen et al., "Heat-Induced Changes in the Mechanics of a Collagenous Tissue: Isothermal Free Shrinkage," Transactions of the ASME, vol. 119, pp. 372-378 (Nov. 1997).

Glaser and Subak-Sharpe,Integrated Circuit Engineering, Addison-Wesley Publishing, Reading, MA (1979). (book—not attached).

Incropera et al., Fundamentals of Heat and Mass Transfer, Wiley, New York (1990). (Book—not attached).

Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.

Emam, Tarek A. et al., "How Safe is High-Power Ultrasonic Dissection?," Annals of Surgery, (2003), pp. 186-191, vol. 237, No. 2, Lippincott Williams & Wilkins, Inc., Philadelphia, PA.

Feil, Wolfgang, M.D., et al., "Ultrasonic Energy for Cutting, Coagulating, and Dissecting," (2005), pp. IV, 17, 21, and 23; ISBN 3-13-127521-9 (New York, NY, Thieme, New York).

McCarus, Steven D. M.D., "Physiologic Mechanism of the Ultrasonically Activated Scalpel," The Journal of the American Association of Gynecologic Laparoscopists; (Aug. 1996), vol. 3, No. 4., pp. 601-606 and 608.

International Search Report and Written Opinion received in PCT Application No. PCT/US2017/041852, mailed on Oct. 6, 2017, 20 Pages.

Extended European Search Report received in European Patent Application No. 20169084.9, mailed on Jul. 3, 2020, 9 pages.

\* cited by examiner

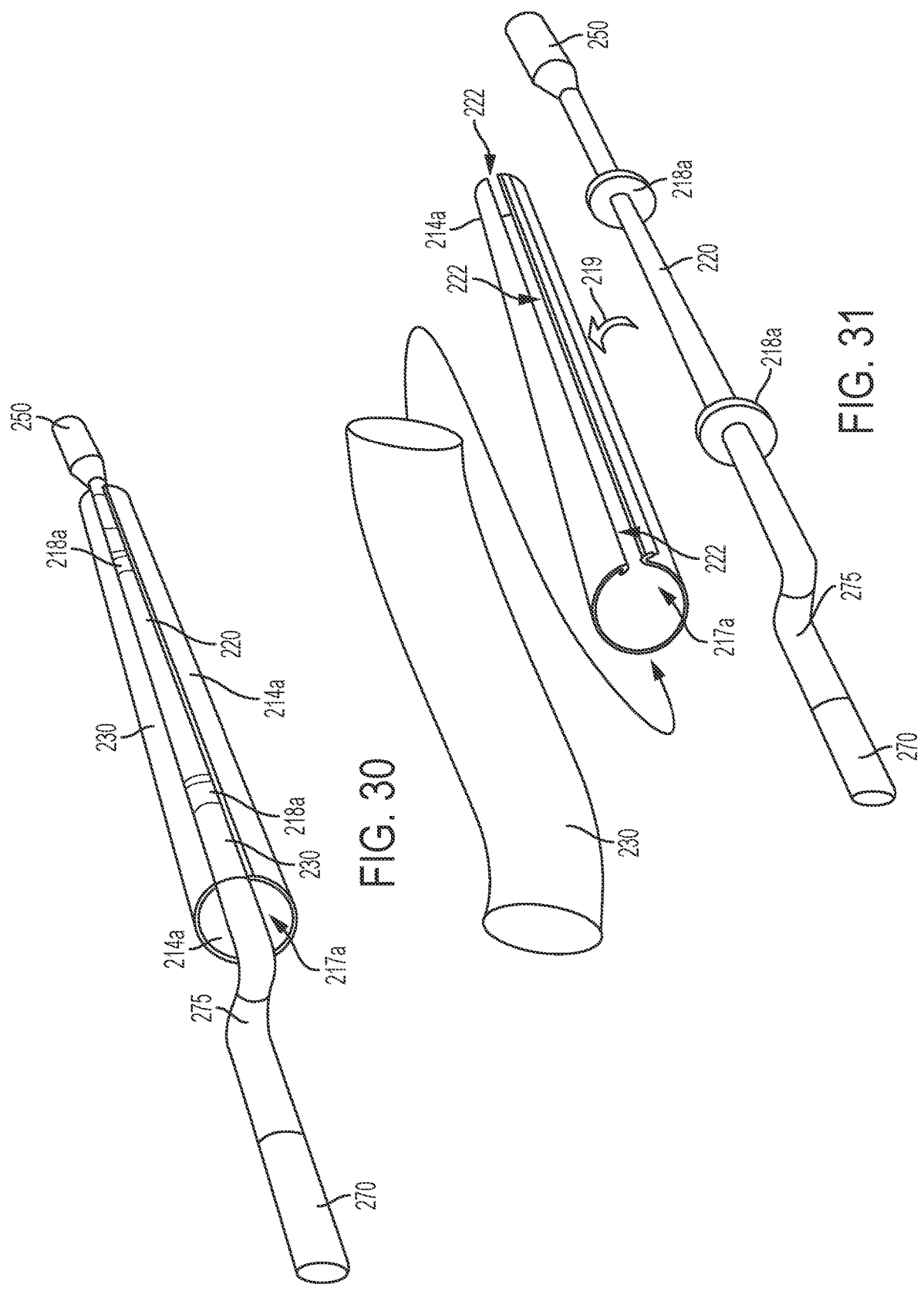

ULTRASONIC SURGICAL INSTRUMENTS HAVING OFFSET BLADES

CROSS-REFERENCE TO RELATED APPLICATION

This application is a divisional application claiming priority under 35 U.S.C. § 121 to U.S. patent application Ser. No. 15/211,402, titled ULTRASONIC SURGICAL INSTRUMENTS HAVING OFFSET BLADES, filed Jul. 15, 2016, now U.S. Patent Application Publication No. 2018/0014848, the entire disclosure of which is hereby incorporated by reference herein.

BACKGROUND

Ultrasonic surgical instruments may be used to cut and/or coagulate biological tissue using energy in the form of mechanical vibrations transmitted to a surgical end-effector (comprising a cutting blade, for example) at ultrasonic frequencies (e.g., 55.5 kilohertz). Activating an end-effector at ultrasonic frequencies induces rapid longitudinal vibratory movement that generates localized heat within contacting tissue, which denatures protein in the tissue, locally disrupts intercellular cohesion, and forms a sticky coagulum. Pressure exerted on tissue surfaces with the blade of an ultrasonic surgical instrument collapses blood vessels and allows the coagulum to form a hemostatic seal.

The ultrasonic mechanical vibrations, when transmitted to biological tissue at suitable energy levels and using a suitable end-effector, may effectively and efficiently cut, dissect, and/or coagulate tissue in an accurate and precise manner. Thus, ultrasonic surgical instruments can minimize patient trauma during surgical procedures by facilitating substantially simultaneous cutting of tissue and hemostatic coagulation. Accordingly, ultrasonic surgical instruments are used by clinicians to perform various surgical procedures, including open (invasive), laparoscopic, endoscopic, and robotic-assisted surgical procedures.

Although ultrasonic surgical instruments have gained wide acceptance among surgeons and other clinicians, some areas of improvement still remain. For example, ultrasonic surgical instruments that facilitate increased surgical site access, visibility, and manipulability would be advantageous. Additionally, ultrasonic surgical instruments with decreased manufacturing costs would be advantageous.

SUMMARY

The invention described in this specification generally relates to ultrasonic surgical instruments. More specifically, the invention comprises ultrasonic surgical instruments having offset blade configurations, which provide for increased surgical site access and visibility to surgeons. The invention also comprises ultrasonic surgical instruments having blades that may be fabricated from sheet metal stock, which decreases manufacturing cost. The invention further comprises ultrasonic surgical blades and end-effectors configured for use with ultrasonic surgical instruments, and related assemblies and systems.

In one example, an ultrasonic surgical instrument comprises an ultrasonic transducer having a central transducer axis, an acoustic horn acoustically coupled to the ultrasonic transducer, and an ultrasonic transmission waveguide acoustically coupled to the acoustic horn. The ultrasonic transmission waveguide comprises a curved portion and a linear portion. An ultrasonic surgical blade is acoustically coupled to the ultrasonic transmission waveguide. The linear portion of the ultrasonic transmission waveguide and the ultrasonic surgical blade are angularly off-set from the central transducer axis.

In another example, an ultrasonic surgical instrument comprises an ultrasonic transducer, an acoustic horn acoustically coupled to the ultrasonic transducer, and an ultrasonic transmission waveguide acoustically coupled to the acoustic horn. The ultrasonic transmission waveguide has a central waveguide axis. An ultrasonic surgical blade is acoustically coupled to the ultrasonic transmission waveguide through a compound curvature component. The compound curvature component transversely off-sets the ultrasonic surgical blade from the central waveguide axis.

In another example, an ultrasonic surgical instrument comprises an ultrasonic transducer, an ultrasonic transmission waveguide acoustically coupled to the ultrasonic transducer, and an ultrasonic surgical blade integrally formed with the ultrasonic transmission waveguide. The ultrasonic transmission waveguide has a tapered width that decreases from a maximum at the acoustic coupling with the ultrasonic transducer to a minimum at a transition to the ultrasonic surgical blade.

It is understood that the invention described in this specification is not necessarily limited to the examples summarized in this Summary.

BRIEF DESCRIPTION OF THE DRAWINGS

Various features and characteristics of the invention described in this specification may be better understood by reference to the accompanying figures, in which:

FIG. 30 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath;

FIG. 31 is an exploded perspective view schematic diagram of the assembly shown in FIG. 30;

Figure 1:
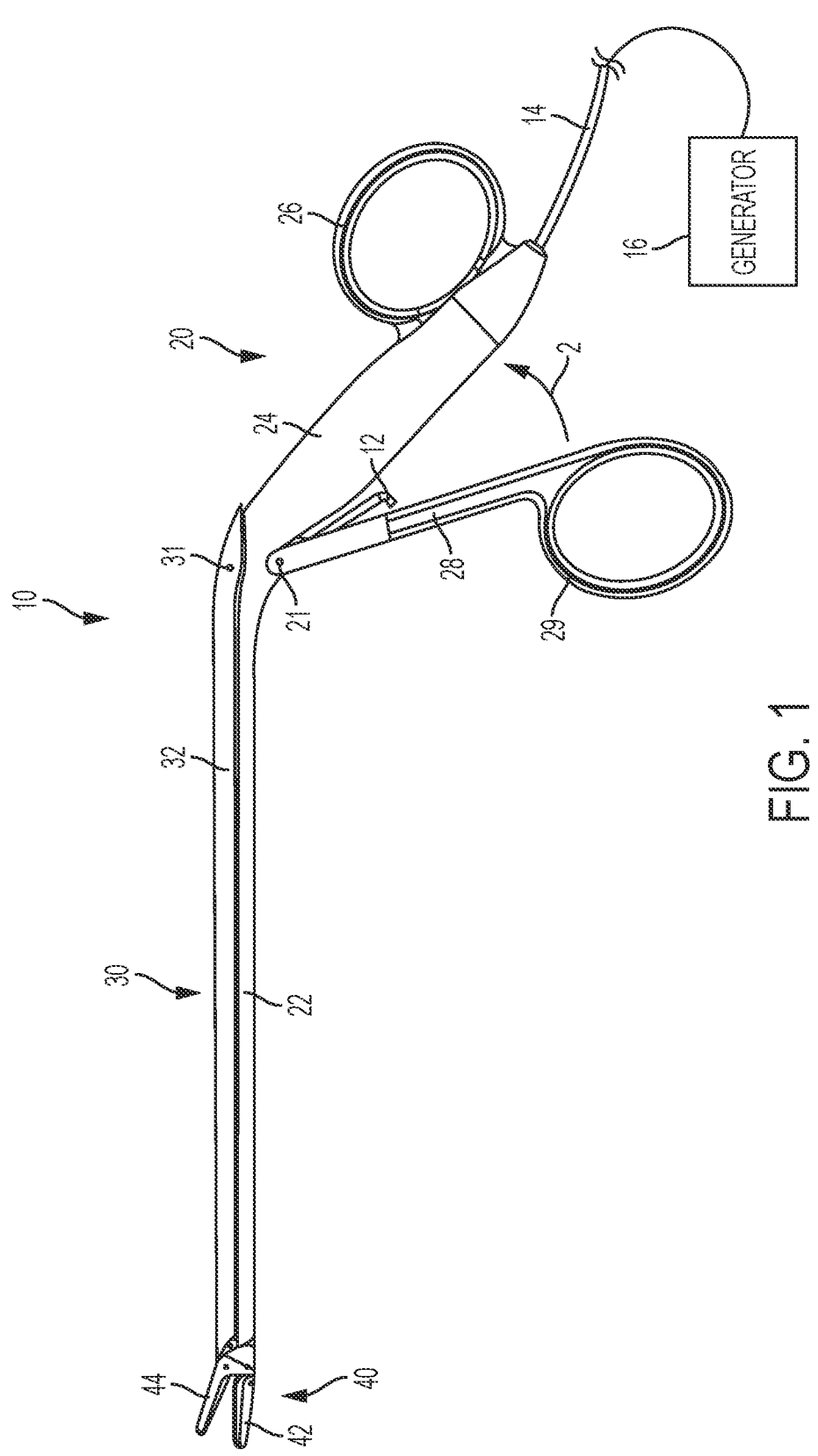
FIG. 1 is a side view of an ultrasonic surgical instrument having a tissue clamping mechanism, shown in an open position, with an angled scissor grip configuration and comprising an ultrasonic surgical blade that is angularly off-set from an ultrasonic transducer located within a handle assembly.
Figure 2:
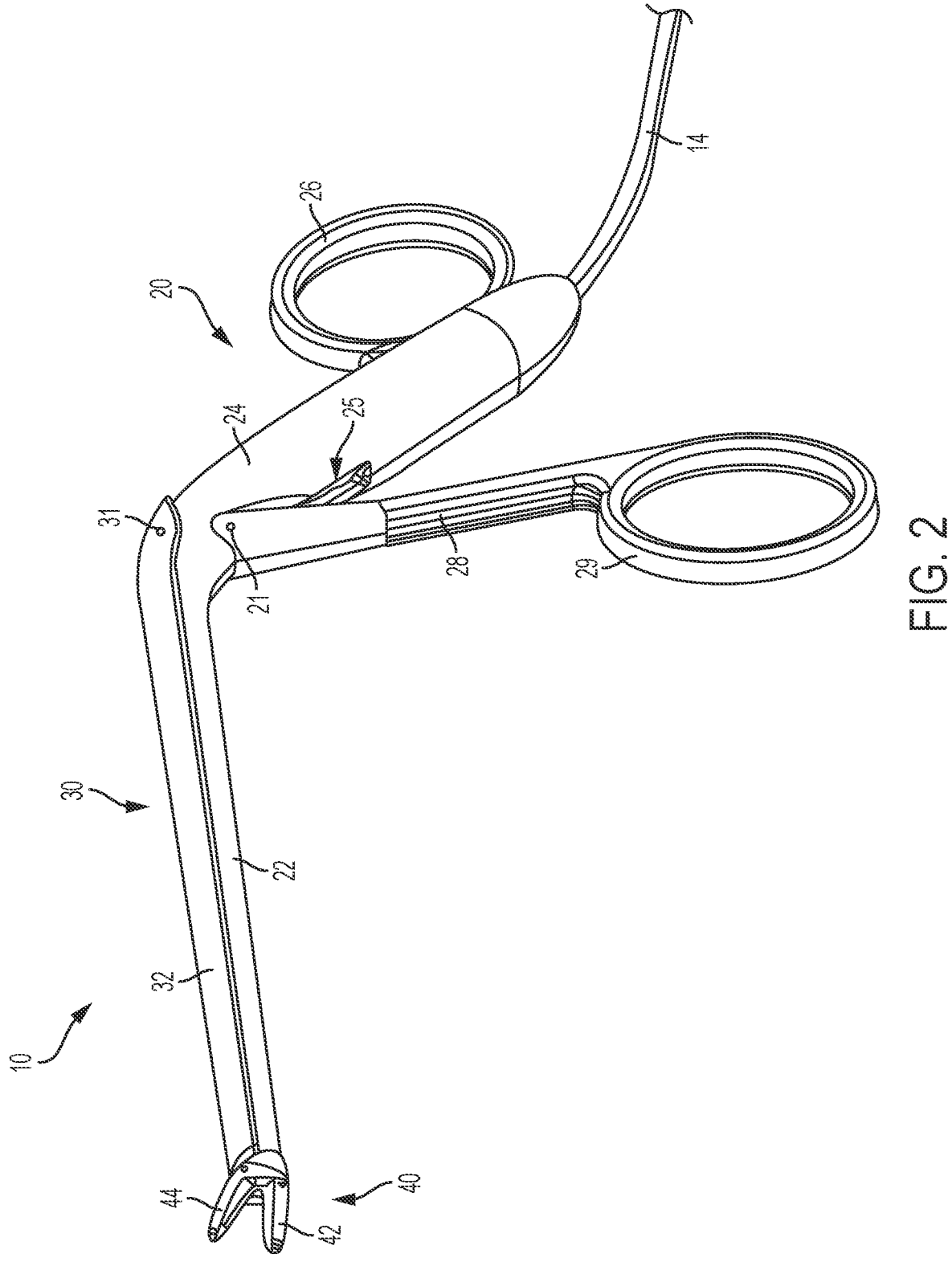
FIG. 2 is a front perspective view of the ultrasonic surgical instrument shown in FIG. 1.
Figure 3:
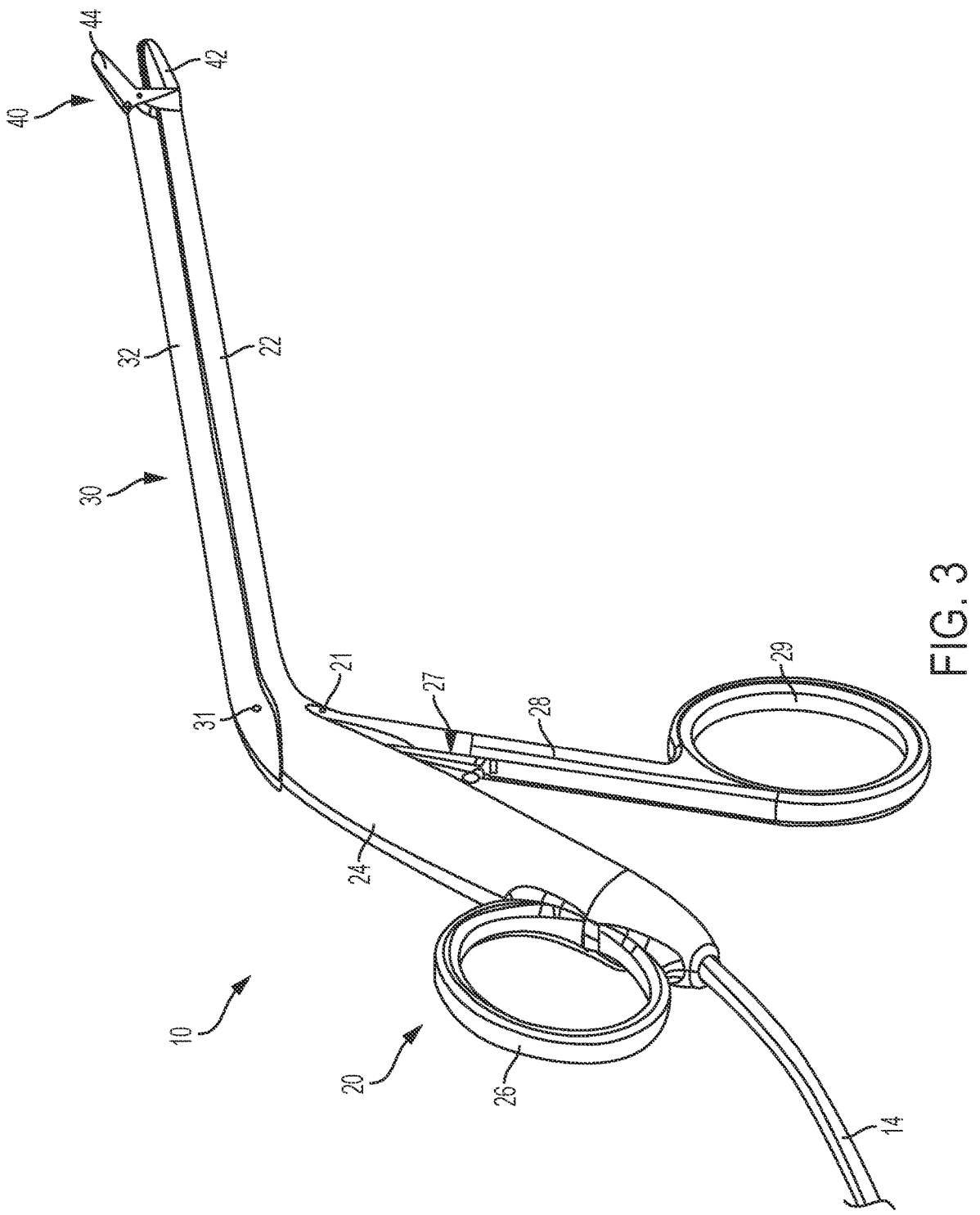
FIG. 3 is a rear perspective view of the ultrasonic surgical instrument shown in FIGS. 1 and 2.

The reader will appreciate the foregoing features and characteristics, as well as others, upon considering the following detailed description of the invention according to this specification.

DESCRIPTION

In this specification, including the claims, spatial terms (e.g., front, rear, back, top, bottom, upper, lower, vertical, horizontal, above, below, over, under, and the like), used to describe the relative orientation, location, or positioning of components, are used for clarity and convenience and are not to be construed as limited to any absolute frame of reference. Additionally, the terms "proximal" and "distal" (and grammatical variants such as "proximally" and "distally") are used in this specification with reference to a surgeon or other operator holding the handle portion of a surgical instrument comprising the feature or characteristic described as "proximal" or "distal," wherein the term "proximal" refers to the portion closest to the operator and the term "distal" refers to the portion located away from the operator. Also, where materials of construction are described for certain components is this specification, the components are not necessarily limited to the materials of construction so described, and other materials of construction may be used to implement the invention in practice.

Ultrasonic surgical instruments generally comprise an ultrasonic transducer acoustically coupled to an ultrasonic surgical blade through an ultrasonic transmission waveguide. In prior ultrasonic surgical instruments, the ultrasonic transducer, the ultrasonic transmission waveguide, and the ultrasonic surgical blade are co-axially aligned along a common longitudinal axis. Examples of such ultrasonic surgical instruments are described, for example, in the following documents, which are incorporated by reference into this specification.

U.S. Pat. No. 5,322,055, entitled CLAMP COAGULATOR/CUTTING SYSTEM FOR ULTRASONIC SURGICAL INSTRUMENTS, issued Jun. 21, 1994;

U.S. Pat. No. 5,873,873, entitled ULTRASONIC CLAMP COAGULATOR APPARATUS HAVING IMPROVED CLAMP MECHANISM, issued Feb. 23, 1999;

U.S. Pat. No. 5,980,510, entitled ULTRASONIC CLAMP COAGULATOR APPARATUS HAVING IMPROVED CLAMP ARM PIVOT MOUNT, issued Nov. 9, 1999;

U.S. Pat. No. 6,325,811, entitled BLADES WITH FUNCTIONAL BALANCE ASYMMETRIES FOR USE WITH ULTRASONIC SURGICAL INSTRUMENTS, issued Dec. 4, 2001;

U.S. Pat. No. 6,773,444, entitled BLADES WITH FUNCTIONAL BALANCE ASYMMETRIES FOR USE WITH ULTRASONIC SURGICAL INSTRUMENTS, issued Aug. 10, 2004;

U.S. Pat. No. 6,783,524, entitled ROBOTIC SURGICAL TOOL WITH ULTRASOUND CAUTERIZING AND CUTTING INSTRUMENT, issued Aug. 31, 2004;

U.S. Patent Application Publication No. 2006/0079874, entitled TISSUE PAD FOR USE WITH AN ULTRASONIC SURGICAL INSTRUMENT, published Apr. 13, 2006;

U.S. Patent Application Publication No. 2007/0191713, entitled ULTRASONIC DEVICE FOR CUTTING AND COAGULATING, published Aug. 16, 2007;

U.S. Patent Application Publication No. 2007/0282333, entitled ULTRASONIC WAVEGUIDE AND BLADE, published Dec. 6, 2007;

U.S. Patent Application Publication No. 2008/0200940, entitled ULTRASONIC DEVICE FOR CUTTING AND COAGULATING, published Aug. 21, 2008;

U.S. Patent Application Publication No. 2009/0105750, entitled ERGONOMIC SURGICAL INSTRUMENTS, published Apr. 23, 2009, now U.S. Pat. No. 8,623,027;

U.S. Patent Application Publication No. 2010/0069940, entitled ULTRASONIC DEVICE FOR FINGERTIP CONTROL, published Mar. 18, 2010, now U.S. Pat. No. 9,023,071;

U.S. Patent Application Publication No. 2011/0015660, entitled ROTATING TRANSDUCER MOUNT FOR ULTRASONIC SURGICAL INSTRUMENTS, published Jan. 20, 2011, now U.S. Pat. No. 8,461,744;

U.S. Patent Application Publication No. 2012/0029546, entitled ULTRASONIC SURGICAL INSTRUMENT BLADES, published Feb. 2, 2012, now U.S. Pat. No. 8,591,536;

U.S. Patent Application Publication No. 2012/0112687, entitled RECHARGE SYSTEM FOR MEDICAL DEVICES, published May 10, 2012, now U.S. Pat. No. 9,381,058;

U.S. Patent Application Publication No. 2012/0116265, entitled SURGICAL INSTRUMENT WITH CHARGING DEVICES, published May 10, 2012;

U.S. Patent Application Publication No. 2014/0005701, entitled SURGICAL INSTRUMENTS WITH

7

ARTICULATING SHAFTS, published Jan. 2, 2014, now U.S. Pat. No. 9,393,037;

U.S. Patent Application Publication No. 2014/0005704, entitled ULTRASONIC SURGICAL INSTRUMENTS WITH DISTALLY POSITIONED JAW ASSEMBLIES, published Jan. 2, 2014, now U.S. Pat. No. 9,351,754;

U.S. Patent Application Publication No. 2014/0114334, entitled FLEXIBLE HARMONIC WAVEGUIDES/ BLADES FOR SURGICAL INSTRUMENTS, published Apr. 24, 2014, now U.S. Pat. No. 9,095,367;

U.S. Patent Application Publication No. 2015/0148831, entitled HANDPIECE AND BLADE CONFIGURATIONS FOR ULTRASONIC SURGICAL INSTRUMENT, published May 28, 2015, now U.S. Pat. No. 9,943,325; and U.S. Patent Application Publication No. 2016/0030076, entitled ACTUATION MECHANISM AND LOAD ADJUSTMENT ASSEMBLIES FOR SURGICAL INSTRUMENTS, published Feb. 4, 2016, now U.S. Pat. No. 10,285,724.

The ultrasonic surgical instruments described in this specification comprise angularly and/or transversely (linearly) off-set ultrasonic surgical blades. Referring to FIGS. 1-11, an ultrasonic surgical instrument 10 has tissue clamping functionality and an angled scissor grip configuration. The ultrasonic surgical instrument 10 comprises a handle assembly 20, a shaft assembly 30 connected to the handle assembly 20, and an end-effector 40 connected to the shaft assembly 30. The handle assembly 20 comprises a handle body 24 comprising a finger grip ring 26 integrally formed on the rear distal surface of the handle body 24 at the bottom end of the handle body 24. The shaft assembly 30 comprises a lower shaft member 22 that is integrally formed with the handle body 24 and a reciprocating upper shaft member 32 located above the lower shaft member 22. Although the lower shaft member 22 is shown integrally formed with the handle body 24, it is understood that the lower shaft member 22 can be otherwise fixedly attached (e.g., welded, fastened, and the like) to the handle body 24, and that the lower shaft member 22 and the handle body 24 are not necessarily required to be formed from a contiguous piece of material.

Figure 11:
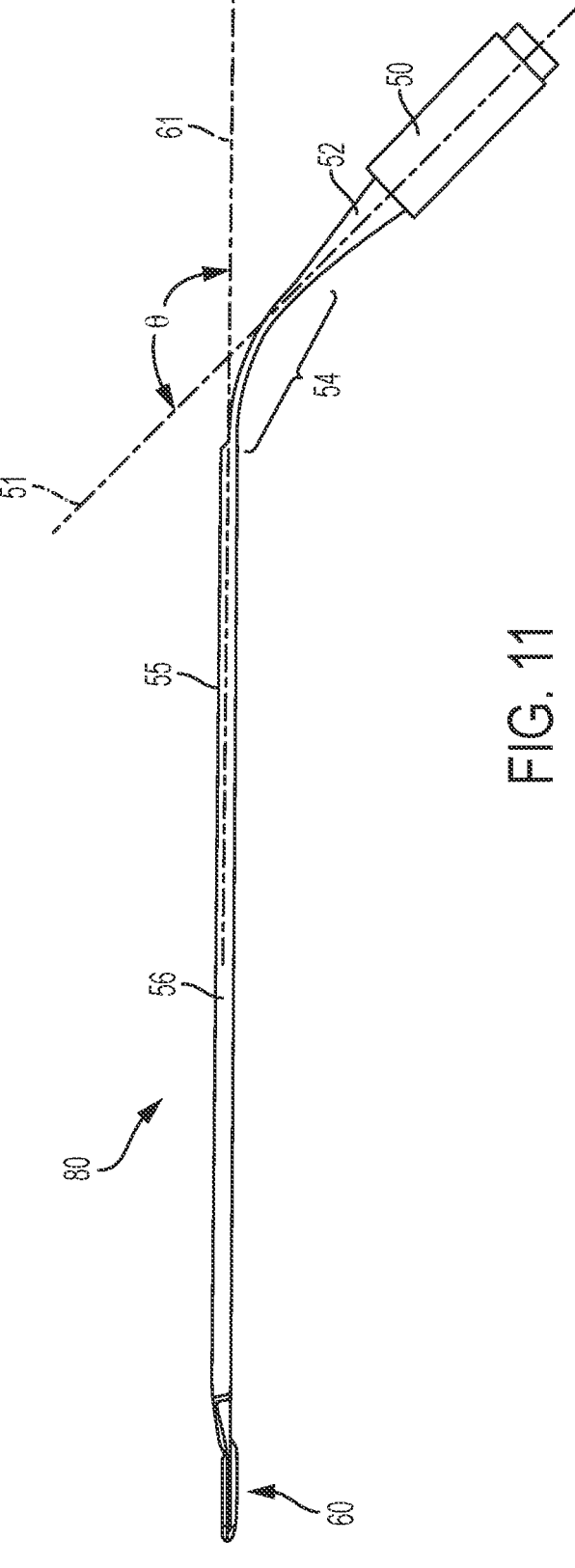
FIG. 11 is a side view schematic diagram of an acoustic system comprising an ultrasonic transducer, an ultrasonic transmission waveguide, and an ultrasonic surgical blade, showing the ultrasonic surgical blade angularly off-set from the ultrasonic transducer.
Figures 12, 13:
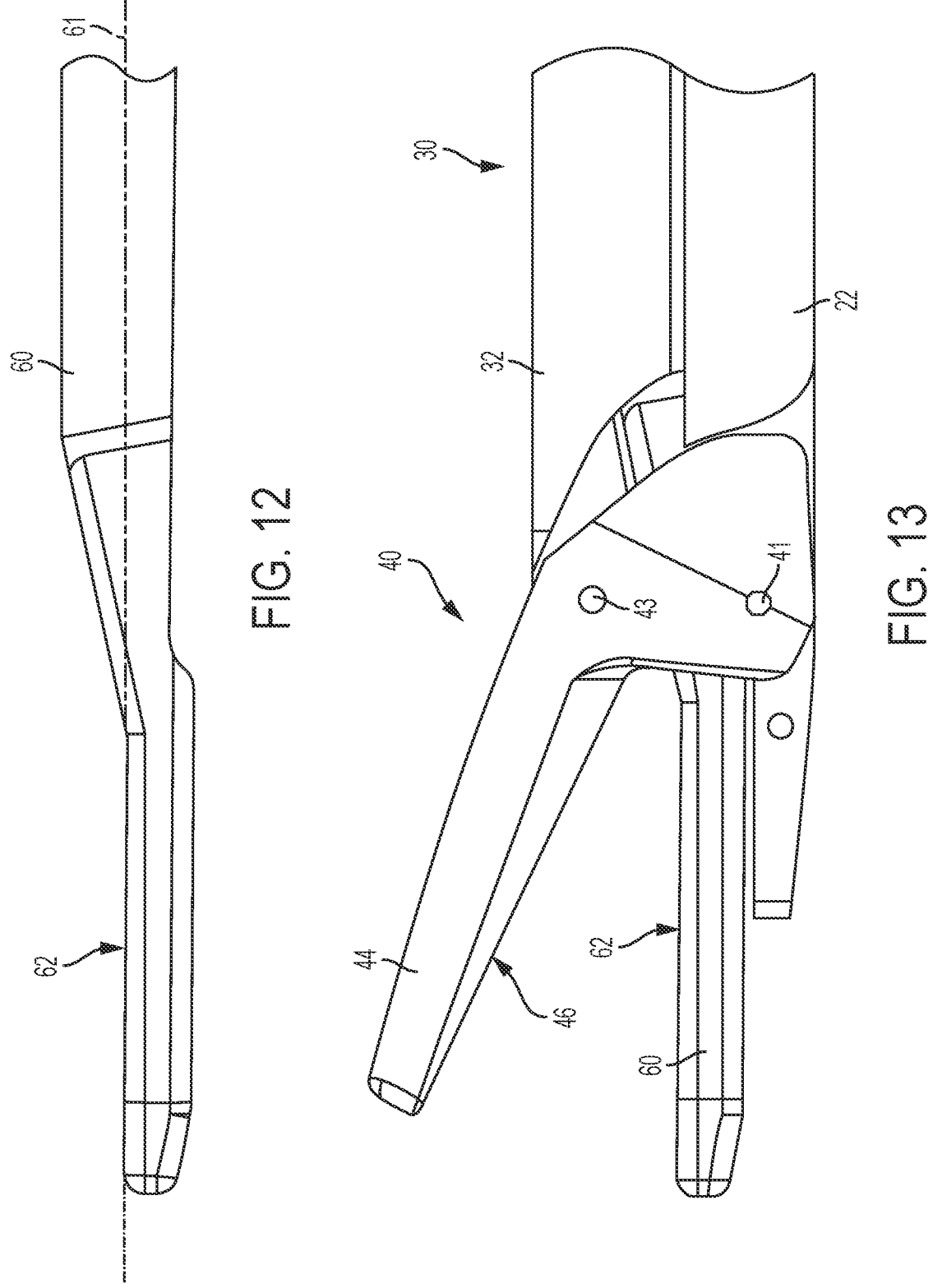
FIG. 12 is a side view schematic diagram of the ultrasonic surgical blade shown in FIG. 11.
FIG. 13 is a side view of the end-effector of the ultrasonic surgical instrument shown in FIGS. 1-10 with a blade housing component removed to show the ultrasonic surgical blade.
Figure 14:
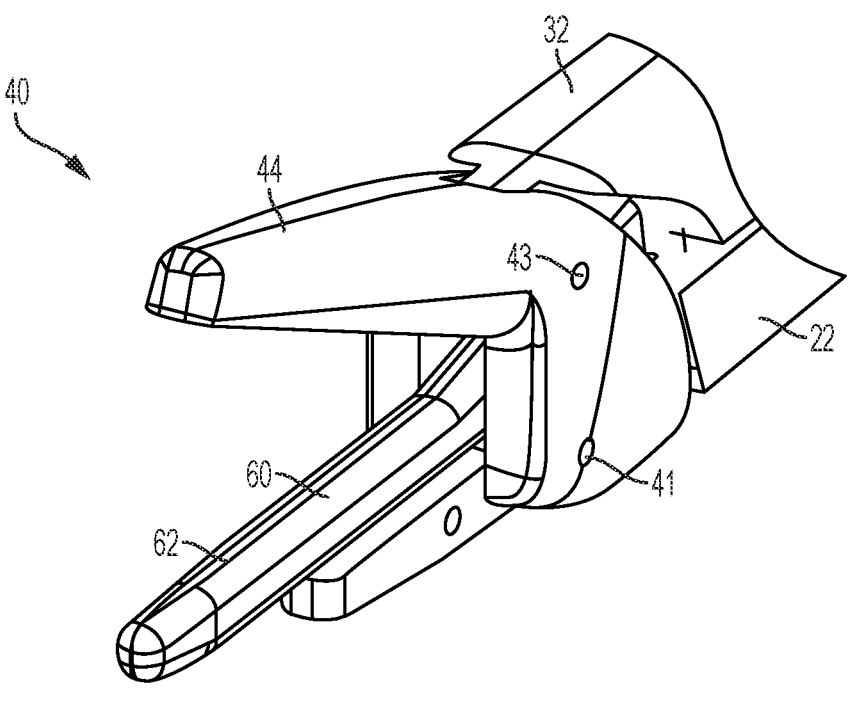
FIG. 14 is a perspective view of the end-effector shown in FIG. 13.
Figure 15:
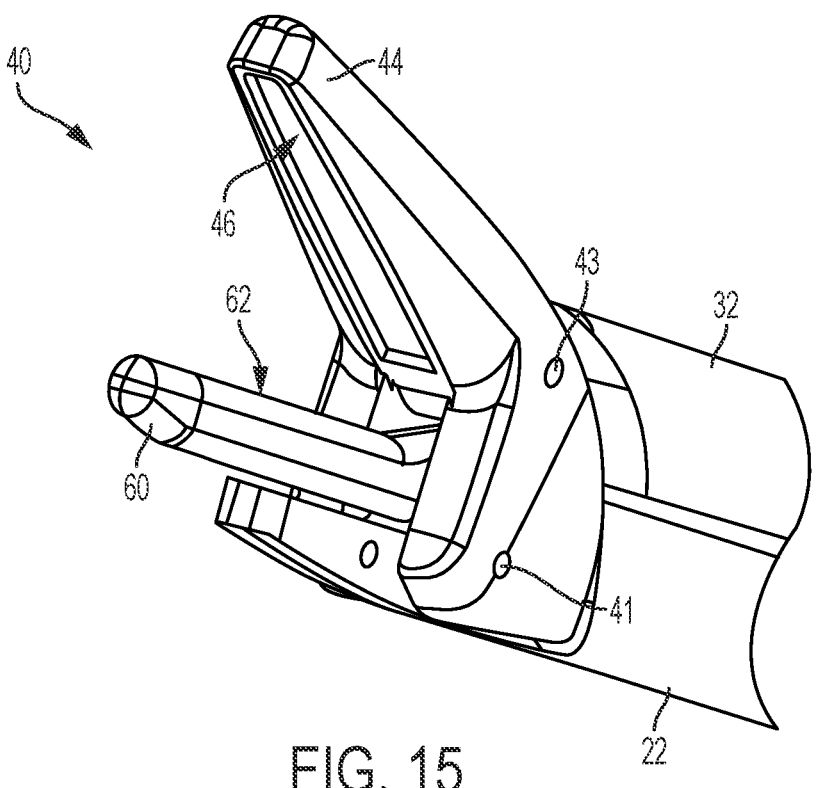
FIG. 15 is a perspective view of the end-effector shown in FIGS. 13 and 14.

The end-effector 40 comprises an ultrasonic surgical blade 60 (see FIGS. 9-15), a blade housing 42, and a clamp arm 44. The blade housing 42 of the end-effector 40 surrounds the non-tissue-engaging surfaces of the ultrasonic surgical blade 60, but the tissue-engaging surfaces 62 of the ultrasonic surgical blade 60 remain exposed for the cutting and coagulation of tissue during operation. The blade housing 42 of the end-effector 40 is connected to the lower shaft member 22 of the shaft assembly 30 using a suitable attachment (e.g., a fastener such as a pin, rivet, or screw). Referring to FIGS. 13-15, the end-effector 40 is shown with the blade housing 42 removed for ease of illustration. The clamp arm 44 is pivotably coupled to the lower shaft member 22 of the shaft assembly 30 through a pivotable joint 41 (e.g., a cylindrical pin located within a pin aperture 41a in the clamp arm 44 and a pin aperture 41b in the distal end of the lower shaft member 22—see FIGS. 9 and 10). The clamp arm 44 is also pivotably coupled to the reciprocating upper shaft member 32 of the shaft assembly 30 through a pivotable joint 43 (e.g., a cylindrical pin located within a pin aperture 43a in the clamp arm 44 and a pin aperture 43b in the distal end of the reciprocating upper shaft member 32—see FIGS. 9 and 10).

As described in more detail below, longitudinal translation of the reciprocating upper shaft member 32 causes pivoting actuation of the clamp arm 44 toward and away from the ultrasonic surgical blade 60 at the end-effector 40. In the open position, as shown in FIGS. 1-4 and 13-17, wherein the clamp arm 44 is pivoted away from the ultrasonic surgical blade 60, the end-effector 40 can be positioned in a surgical site so that tissue is located between a tissue-engaging surface 62 of the ultrasonic surgical blade 60 and a tissue-engaging surface 46 of the clamp arm 44. In the closed position, as shown in FIGS. 5-8 and 18, tissue is mechanically clamped between the respective tissue-engaging surfaces 62 and 46 of the ultrasonic surgical blade 60 and the clamp arm 44, and ultrasonic activation of the blade 60 can cause cutting and/or coagulation of the clamped tissue.

Figure 4:
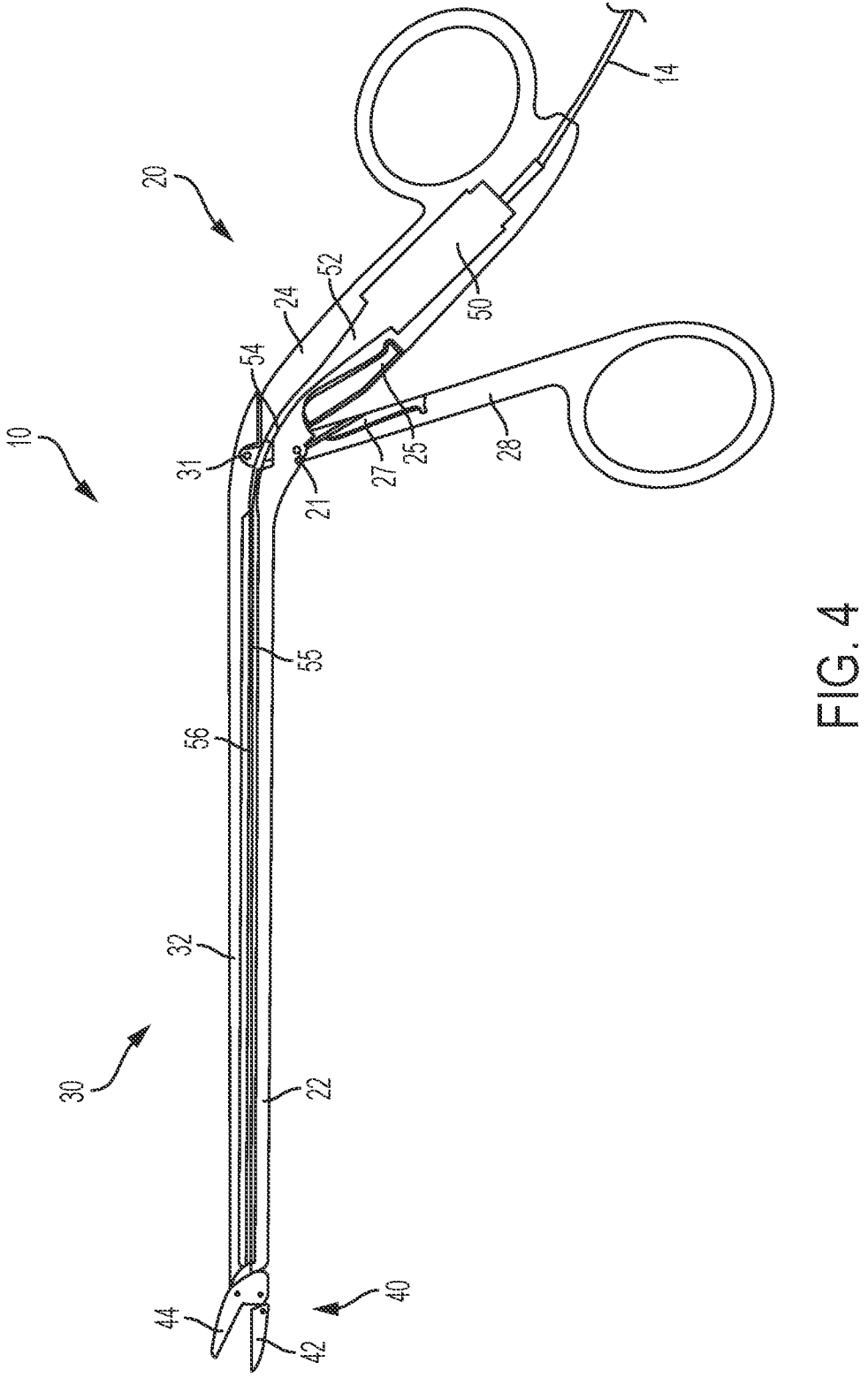
FIG. 4 is a side cross-sectional view of the ultrasonic surgical instrument shown in FIGS. 1-3.
Figure 5:
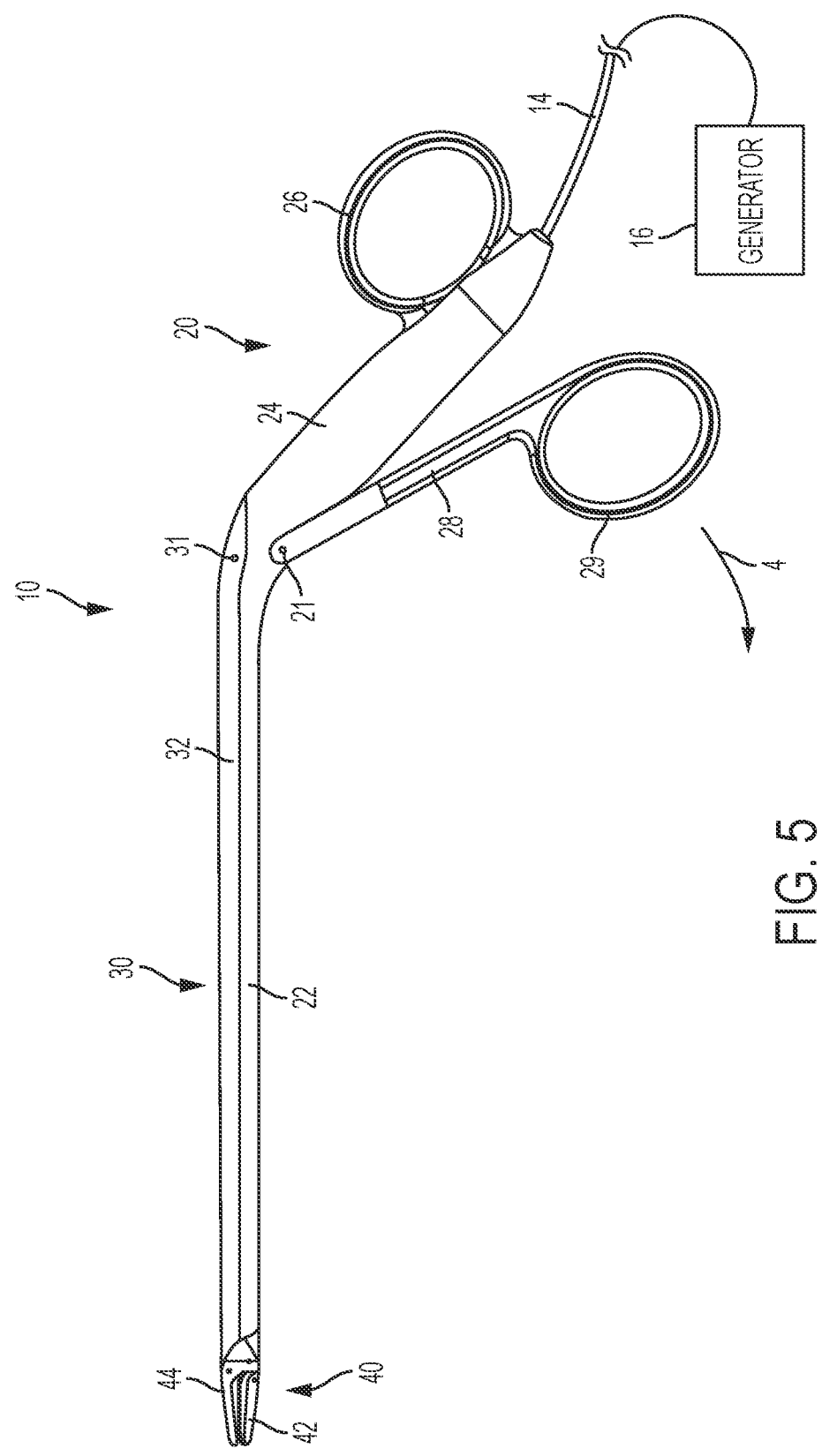
FIG. 5 is a side view of the ultrasonic surgical instrument shown in FIGS. 1-4 with the tissue clamping mechanism shown in a closed position.
Figure 6:
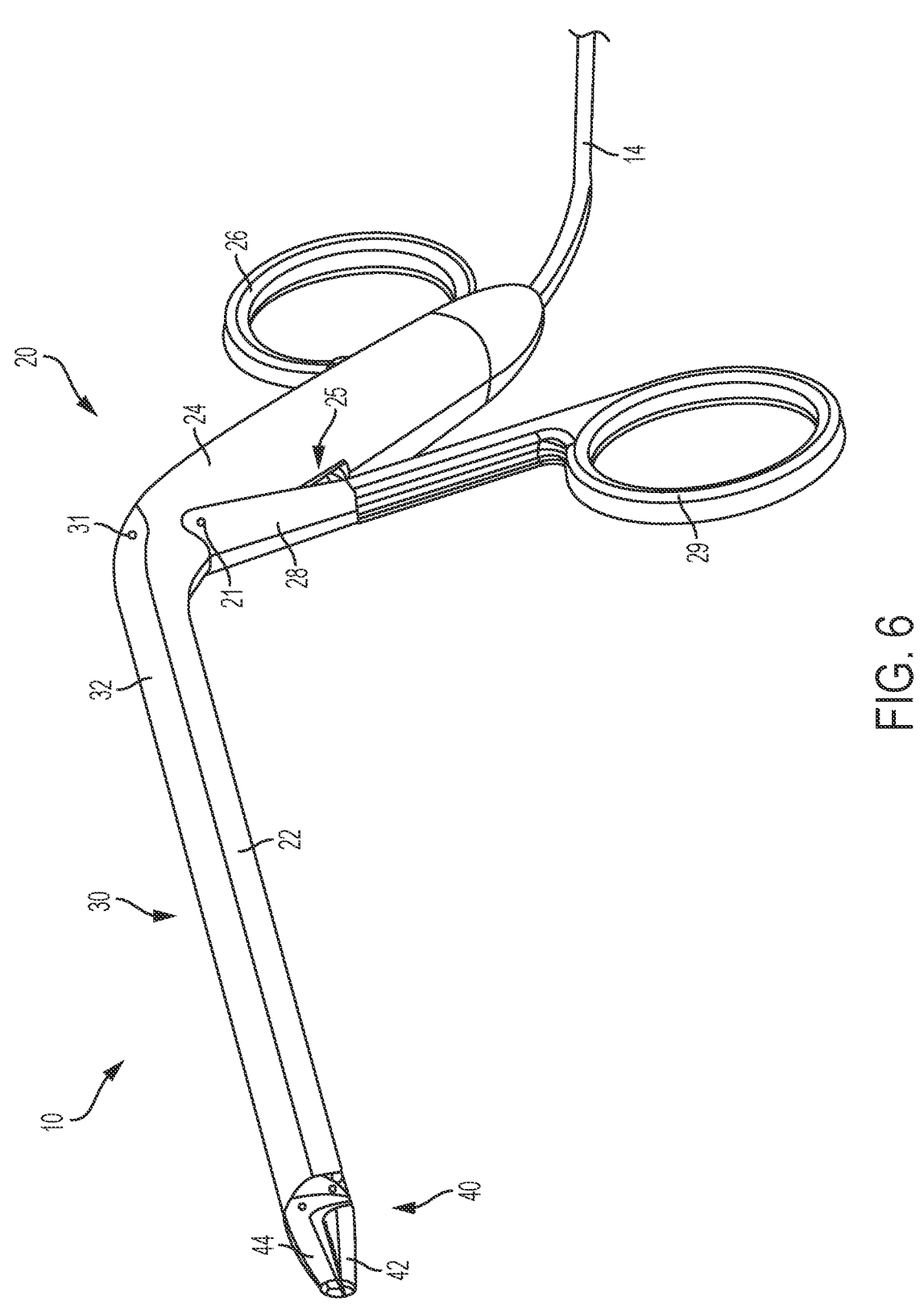
FIG. 6 is a front perspective view of the ultrasonic surgical instrument shown in FIG. 5.
Figure 7:
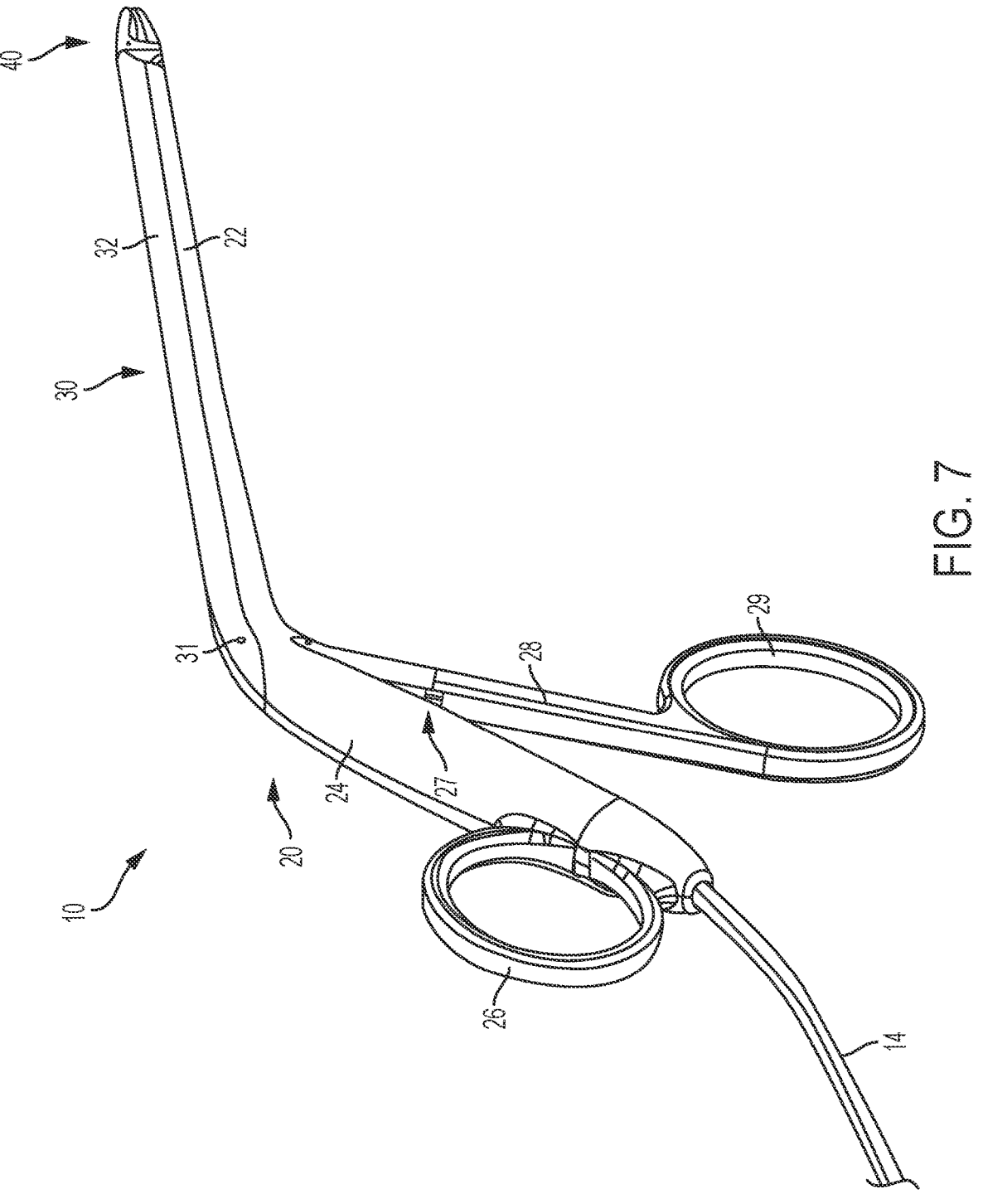
FIG. 7 is a rear perspective view of the ultrasonic surgical instrument shown in FIGS. 5 and 6.
Figure 8:
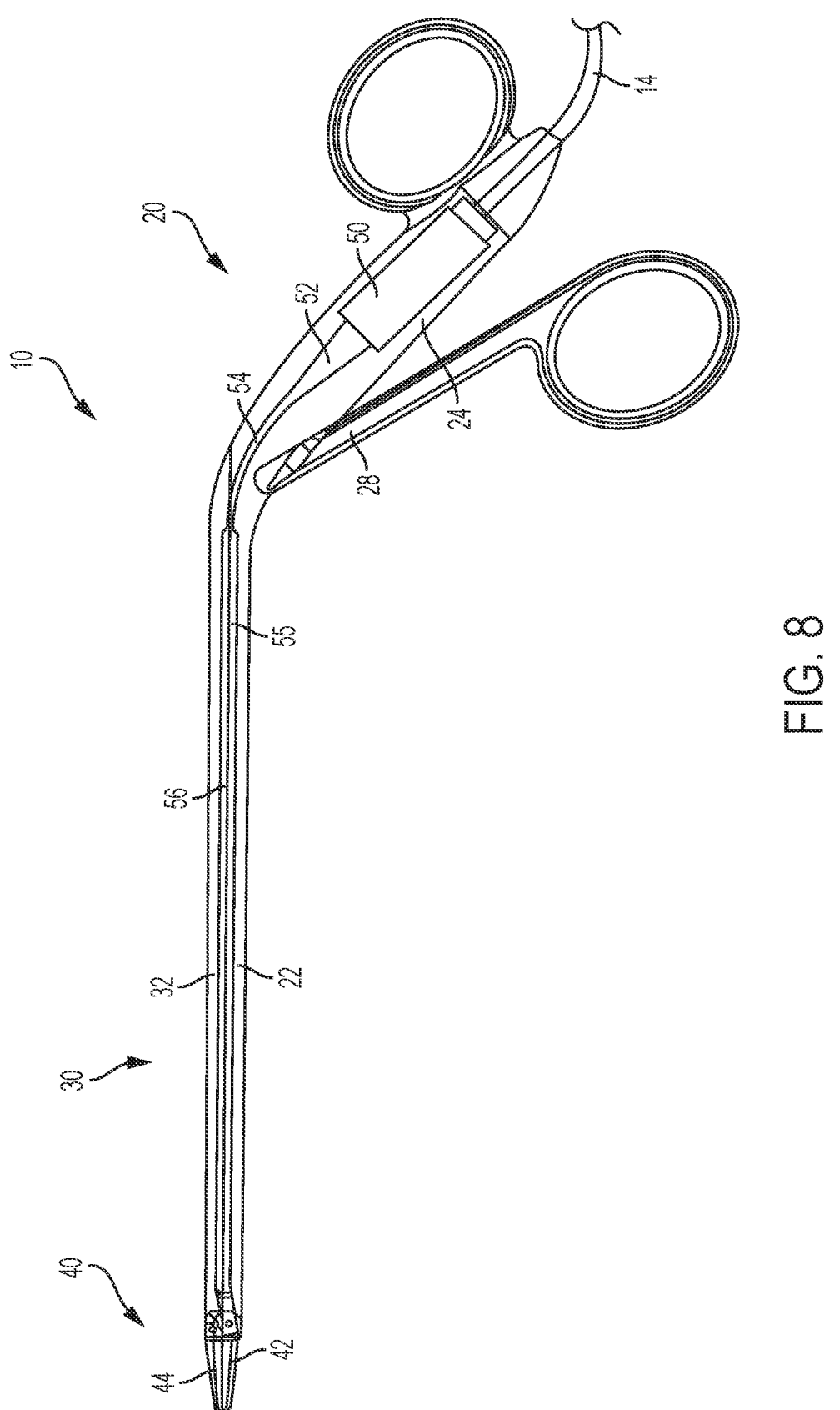
FIG. 8 is a side cross-sectional view of the ultrasonic surgical instrument shown in FIGS. 5-7.

Referring to FIGS. 4 and 8-11, the ultrasonic surgical blade 60 is acoustically coupled to an ultrasonic transmission waveguide 56. The ultrasonic transmission waveguide 56 is in turn acoustically coupled to an acoustic horn 52, which is in turn acoustically coupled to an ultrasonic transducer 50. The ultrasonic transmission waveguide 56 comprises a linear portion 55 located within the shaft assembly 30 between the lower shaft member 22 and the reciprocating upper shaft member 32. The ultrasonic transmission waveguide 56 further comprises a curved portion 54 acoustically coupled between the linear portion 55 and the acoustic horn 52. Referring to FIGS. 4 and 8, the curved portion 54 of the ultrasonic transmission waveguide 56, the acoustic horn 52, and the ultrasonic transducer 50 are located within the handle body 24 of the handle assembly 20. The ultrasonic transducer 50 is electrically coupled to a generator 16 (see FIGS. 1 and 16) via a cable 14.

During operation, the ultrasonic transducer 50 receives electrical power from the generator 16 and converts the electrical power into ultrasonic vibrations using at least one, and typically a stack of, for example, four to eight ceramic piezoelectric elements with a motion null point located at some point along the stack such as at the proximal rear end of the stack, for example. The generator 16 may include a power source and control module that is configured to provide an electrical power profile to the ultrasonic transducer 50 that is configured for the generation of ultrasonic vibrations through the transducer 50. By way of example only, the generator 16 may comprise a GEN 300 available from Ethicon Endo-Surgery, Inc. of Cincinnati, Ohio. The generator 16 may be constructed as described in U.S. Patent Application Publication No. 2011/0087212, entitled SURGICAL GENERATOR FOR ULTRASONIC AND ELECTROSURGICAL DEVICES, published Apr. 14, 2011, now U.S. Pat. No. 8,986,302, which is incorporated by reference into this specification. It is understood that at least some of the functionality of the generator 16 may be integrated into the handle assembly 20; for example, the handle assembly 20 may include a battery or other on-board power source such that cable 14 is omitted.

The functionality provided by the generator 16 may also be provided as described in U.S. Pat. No. 6,480,796 (METHOD FOR IMPROVING THE START UP OF AN ULTRASONIC SYSTEM UNDER ZERO LOAD CONDITIONS); U.S. Pat. No. 6,537,291 (METHOD FOR DETECTING A LOOSE BLADE IN A HAND PIECE CONNECTED TO AN ULTRASONIC SURGICAL SYSTEM); U.S. Pat. No. 6,626,926 (METHOD FOR DRIVING AN ULTRASONIC SYSTEM TO IMPROVE ACQUISITION OF BLADE RESONANCE FREQUENCY AT STARTUP); U.S. Pat. No. 6,633,234 (METHOD FOR DETECTING BLADE BREAKAGE USING RATE AND/OR IMPEDANCE INFORMATION); U.S. Pat. No. 6,662,127 (METHOD FOR DETECTING PRESENCE OF A

9

BLADE IN AN ULTRASONIC SYSTEM); U.S. Pat. No. 6,678,621 (OUTPUT DISPLACEMENT CONTROL USING PHASE MARGIN IN AN ULTRASONIC SURGICAL HAND PIECE); U.S. Pat. No. 6,679,899 (METHOD FOR DETECTING TRANSVERSE VIBRATIONS IN AN ULTRASONIC HAND PIECE); U.S. Pat. No. 6,908,472 (APPARATUS AND METHOD FOR ALTERING GENERATOR FUNCTIONS IN AN ULTRASONIC SURGICAL SYSTEM); U.S. Pat. No. 6,977,495 (DETECTION CIRCUITRY FOR SURGICAL HANDPIECE SYSTEM); U.S. Pat. No. 7,077,853 (METHOD FOR CALCULATING TRANSDUCER CAPACITANCE TO DETERMINE TRANSDUCER TEMPERATURE); U.S. Pat. No. 7,179,271 (METHOD FOR DRIVING AN ULTRASONIC SYSTEM TO IMPROVE ACQUISITION OF BLADE RESONANCE FREQUENCY AT STARTUP); and U.S. Pat. No. 7,273,483 (APPARATUS AND METHOD FOR ALERTING GENERATOR FUNCTIONS IN AN ULTRASONIC SURGICAL SYSTEM), each of which is incorporated by reference into this specification.

Figure 9:
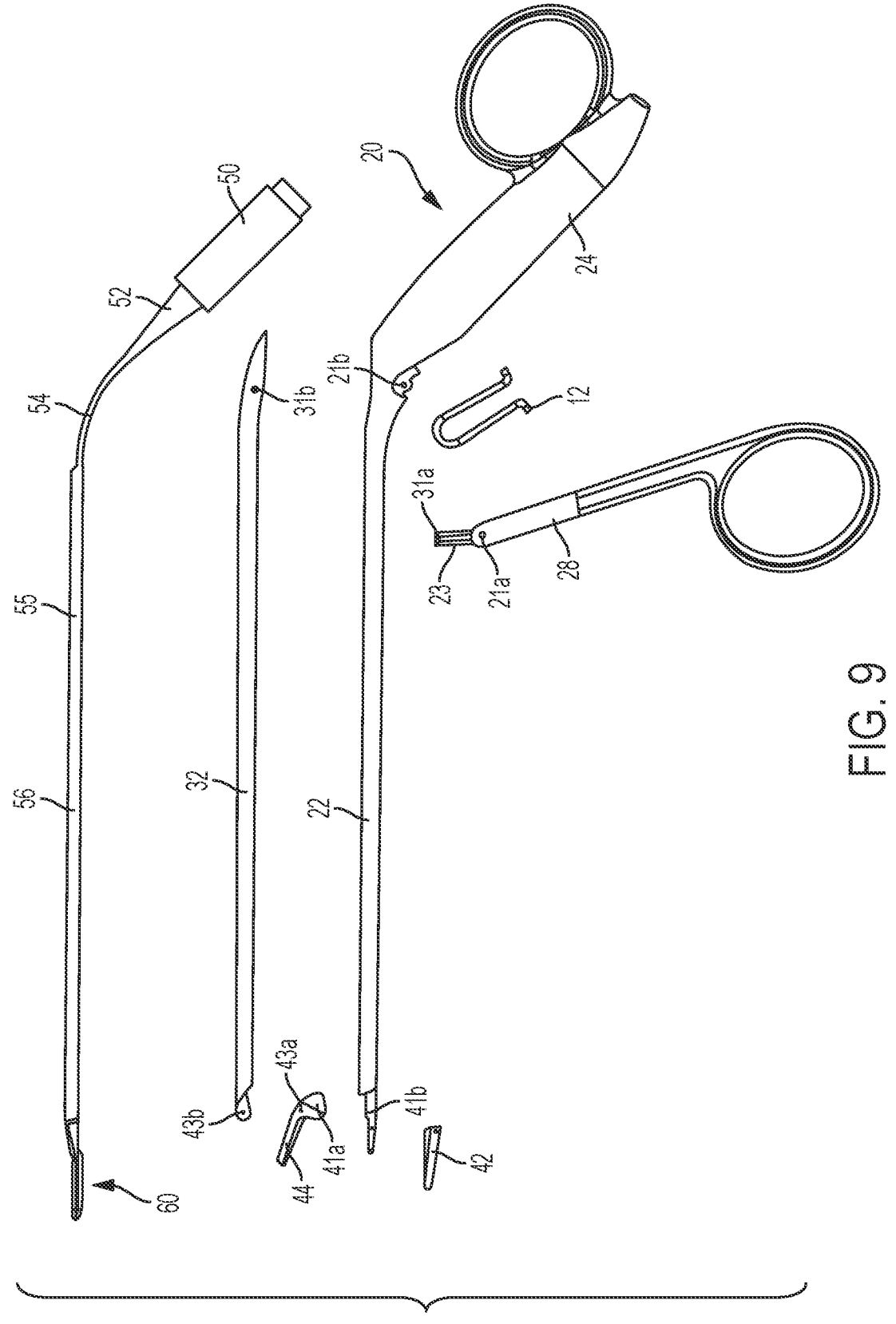
FIG. 9 is an exploded side view of the ultrasonic surgical instrument shown in FIGS. 1-8.
Figure 10:
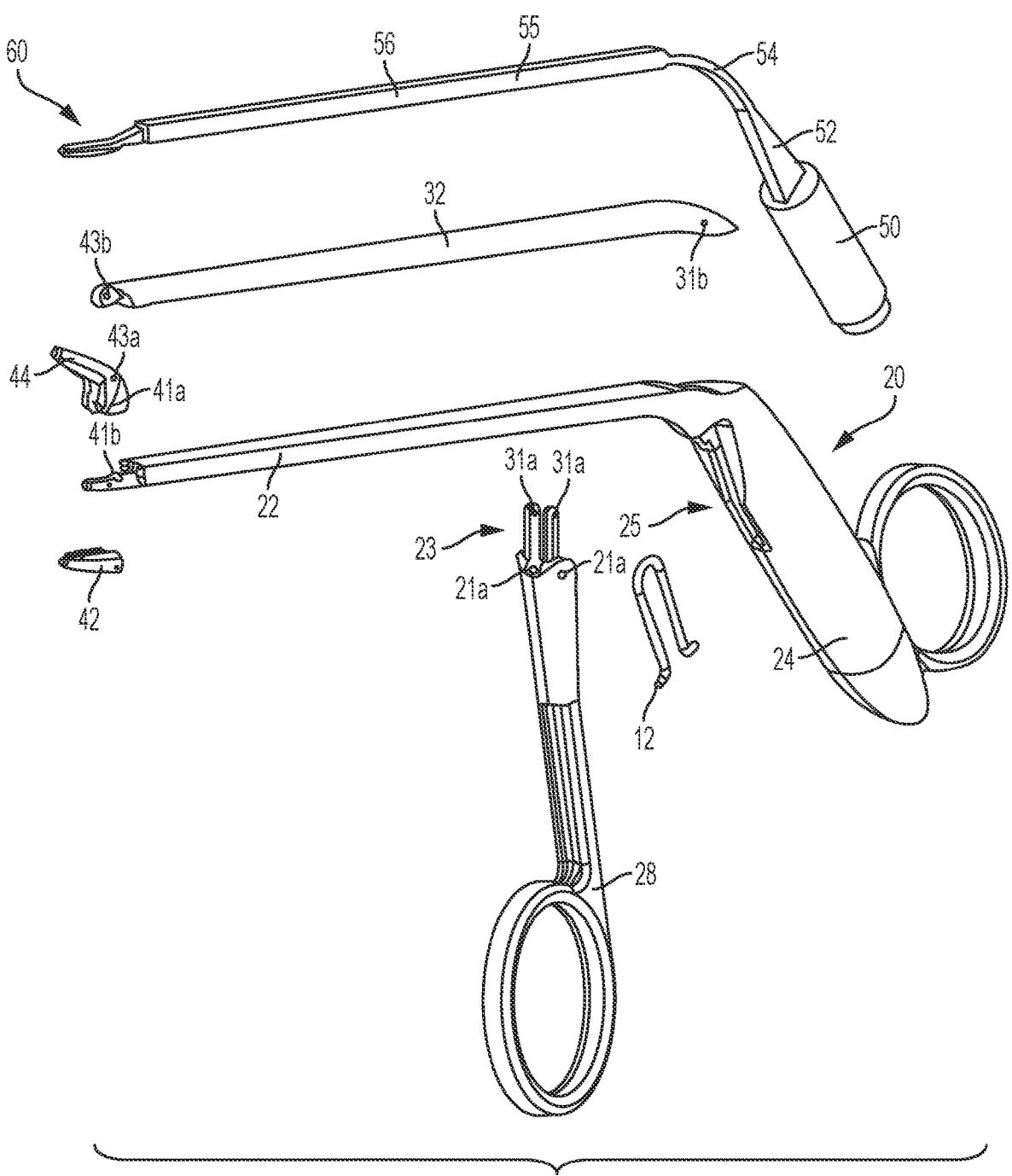
FIG. 10 an exploded front perspective view of the ultrasonic surgical instrument shown in FIGS. 1-9.

Referring again to FIGS. 1-11, the handle assembly 20 further comprises a clamp actuation member 28 comprising a finger grip ring 29 integrally formed on the front proximal surface of the clamp actuation member 28 at the bottom end of the clamp actuation member 28. Referring to FIGS. 9 and 10, the clamp actuation member 28 further comprises levering projections 23 extending from the top end of the clamp actuation member 28. The clamp actuation member 28 is pivotably coupled to the handle body 24 of the handle assembly 20 through a pivotable joint 21 (e.g., a cylindrical pin located within a pin aperture 21a in the clamp actuation member 28 and a pin aperture 21b in the handle assembly 20). The levering projections 23 of the clamp actuation member 28 are pivotably coupled to the reciprocating upper shaft member 32 of the shaft assembly 30 through a pivotable joint 31 (e.g., a cylindrical pin located within a pin aperture 31a in the levering projections 23 and a pin aperture 31b in the reciprocating upper shaft member 32).

As described above, the handle assembly 20 comprises a scissor grip configuration. It is understood, however, that a handle assembly can be structured in other configurations including, but not necessarily limited to, a pistol grip configuration as described below in connection with FIG. 21. In the illustrated scissor grip configuration, the pivoting of the clamp actuation member 28 toward and away from the handle body 24 (for example, by a surgeon's or other operator's hand with their thumb located through the finger grip ring 26 and their middle finger located through the finger grip ring 29—see FIGS. 17 and 18) longitudinally translates the reciprocating upper shaft member 32 distally and proximally, respectively, which in turn pivots the clamp arm 44 toward and away from the ultrasonic surgical blade 60, respectively, which closes and opens the clamping action of the end-effector 40. The reciprocating upper shaft member 32 translates distally and proximally relative to the lower shaft member 22, and over the linear portion 55 of the ultrasonic transmission waveguide 56, during closing and opening action of the ultrasonic surgical instrument 10.

Referring again to FIGS. 9 and 10, the handle assembly 20 comprises a biasing member 12. The biasing member 12 is illustrated in the form of a U-shaped spring clip, but it is understood that other biasing member configurations may be used. The biasing member 12 is located between the handle body 24 and the clamp actuation member 28. Referring to FIGS. 2-4, 6, 7, and 10, the biasing member 12 is seated within a recess 25 in the front proximal surface of the handle body 24 and a recess 27 in the rear distal surface of the clamp actuation member 28. The biasing member 12 biases the clamp actuation member 28 away from the handle body 24, which biases the reciprocating upper shaft member 32 proximally away from the end-effector 40, which biases the clamp arm 44 away from the ultrasonic surgical blade 60, thereby biasing the end-effector into an open position.

When a surgeon or other operator pivots the clamp actuation member 28 proximally about the joint 21, against the biasing force provided by the biasing member 12, and toward the handle body 20 (as indicated by arrow 2 in FIG. 1), the levering projections 23 pivot distally and transmit the distal motion to the reciprocating upper shaft member 32 through the joint 31. The distal motion of the reciprocating upper shaft member 32 transmits through the joint 43 to the clamp arm 44. The distal motion transmitted through the joint 43 causes the clamp arm 44 to pivot about the joint 41 toward the ultrasonic surgical blade 60, thereby closing the end-effector 40.

To open the end-effector 40, a surgeon or other operator releases the force provided by their hand against the biasing force provided by the biasing member 12. The biasing member 12 then pivots the clamp actuation member 28 distally about the joint 21 away from the handle body 20 (as indicated by arrow 4 in FIG. 5), and the levering projections 23 pivot proximally and transmit the proximal motion to the reciprocating upper shaft member 32 through the joint 31. The proximal motion of the reciprocating upper shaft member 32 transmits through the joint 43 to the clamp arm 44. The proximal motion transmitted through the joint 43 causes the clamp arm 44 to pivot about the joint 41 away from the ultrasonic surgical blade 60, thereby opening the end-effector 40.

The ultrasonic surgical instrument 10 comprises an acoustic system 80. Referring to FIG. 11, the acoustic system 80 comprises the ultrasonic transducer 50, the acoustic horn 52, the ultrasonic transmission waveguide 56, and the ultrasonic surgical blade 60. As described above, the ultrasonic surgical blade 60 is acoustically coupled to the acoustic horn 52 and the ultrasonic transducer 50 through the ultrasonic transmission waveguide 56, which comprises a linear portion 55 located within the shaft assembly 30 and a curved portion 54 located within the handle assembly 20.

The orientation of the ultrasonic transducer 50 within the handle assembly 20 defines a central (linear) transducer axis 51, and the orientation of the linear portion 55 of the ultrasonic transmission waveguide 56 within the shaft assembly 30 defines a central (linear) waveguide/shaft axis 61. The central transducer axis 51 and the central waveguide/shaft axis 61 intersect and form an angle θ that angularly off-sets the ultrasonic surgical blade 60 from the central transducer axis 51. The angular off-set of the ultrasonic surgical blade 60 (and the linear portion 55 of the ultrasonic transmission waveguide 56) from the central transducer axis 51 is provided by the curved portion 54 of the ultrasonic transmission waveguide 56, which acoustically couples the linear portion 55 to the horn 52. The off-set angle θ may range, for example, from 120-degrees to 150-degrees, or any sub-range subsumed therein, such as, for example, from 130-degrees to 140-degrees. An off-set angle θ of approximately 135-degrees may provide an optimal balance of human factors and ergonomics for a surgeon or other operator of the ultrasonic surgical instrument 10 and effectiveness and efficiency of acoustic transmission through the curved portion 54 of the ultrasonic transmission waveguide 56.

The components of the acoustic system 80 may be configured to ultrasonically vibrate at the same resonant frequency. When the ultrasonic transducer 50 is energized, a standing wave is established in the ultrasonic transmission waveguide 56 defining nodes and antinodes, where the nodes represent regions of minimal or no displacement and the antinodes represent regions of maximum displacement. The nodes and antinodes occur periodically based on the driving frequency of approximately 55.5 kilohertz, for example, and the structure and materials of construction of the acoustic horn 52, the ultrasonic transmission waveguide 56, and the ultrasonic surgical blade 60. The nodes and antinodes are located at one quarter wavelength apart.

The ultrasonic transducer 50, the acoustic horn 52, the ultrasonic transmission waveguide 56, and the ultrasonic surgical blade 60 may be tuned such that the resulting length of each such element is one-half wavelength or a multiple thereof. The back and forth vibrating motion provided by the ultrasonic transducer 50 is amplified as the diameter of the acoustic horn 52 decreases closer to the ultrasonic transmission waveguide 56. The acoustic horn 52 and the ultrasonic transmission waveguide 56 may be shaped and dimensioned to amplify the motion of the ultrasonic surgical blade 60 and provide ultrasonic vibration in resonance with the rest of the acoustic system 80, which produces the maximum vibratory motion of the distal end of the acoustic horn 52 where it transitions to the ultrasonic transmission waveguide 56. For example, vibratory motion from 20 to 25 microns peak-to-peak at the piezoelectric elements of the ultrasonic transducer 50 may be amplified by the horn 52 into movement in the ultrasonic surgical blade 60 of about 40 to 100 microns peak-to-peak.

The ultrasonic vibrations that are generated by the ultrasonic transducer 50 and amplified by the horn 52 are transmitted along the ultrasonic transmission waveguide 56, through the handle assembly 20 and the shaft assembly 30, and reach the ultrasonic surgical blade 60 in the end-effector 40. The ultrasonic transmission waveguide 56 is secured within and acoustically isolated from the handle assembly 20 and the shaft assembly 30 using, for example, attachments and/or isolation spacers (not shown). The attachments and/or isolation spacers used to secure and isolate the ultrasonic transmission waveguide 56 within the handle assembly 20 and the shaft assembly 30 are located at position(s) along the length of the waveguide 56 corresponding to a node (no vibratory motion) associated with resonant ultrasonic vibrations transmitted through the ultrasonic transmission waveguide 56.

As described above, when the ultrasonic surgical blade 60 is in an activated state (i.e., vibrating ultrasonically), the ultrasonic surgical blade 60 is operable to effectively cut through and seal tissue, particularly when the tissue is being clamped between the clamp arm 44 and the ultrasonic surgical blade 60. It is understood that the waveguide 56, like the horn 52, may be configured to amplify ultrasonic mechanical vibrations transmitted through the waveguide 56, and may include features operable to control the gain of the vibrations along the waveguide 56 and/or features to tune the waveguide 56 to the resonant frequency of the acoustic system 80.

In one example, the distal end of the ultrasonic surgical blade 60 is located at a position corresponding to an antinode associated with resonant ultrasonic vibrations communicated through the ultrasonic transmission waveguide 56, in order to tune the acoustic system 80 to a preferred resonant frequency $f_0$ when the acoustic system 80 is not loaded by tissue. When the ultrasonic transducer 50 is energized, the distal end of the ultrasonic surgical blade 60 is configured to move longitudinally along the central waveguide/shaft axis

61 (see FIG. 12) in the range of, for example, approximately 10 to 500 microns peak-to-peak, and in some instances in the range of about 20 to about 200 microns at a predetermined vibratory frequency $f_0$ of, for example, 55.5 kHz. When the ultrasonic transducer 50 is activated, the piezoelectric-mechanical vibrations are transmitted through the acoustic horn 52 and the ultrasonic transmission waveguide 56 to reach the ultrasonic surgical blade 60, thereby providing vibration of the ultrasonic surgical blade 60 at the resonant ultrasonic frequency.

In another example, the distal end of the ultrasonic surgical blade 60 is located at a position corresponding to a node associated with resonant ultrasonic vibrations communicated through the waveguide 56. When the ultrasonic transducer 50 is energized, the distal end of the ultrasonic surgical blade 60 does not move longitudinally, but a region of the tissue-engaging surface 62 corresponds to an antinode, and that portion of the ultrasonic surgical blade 60 moves along the central waveguide/shaft axis 61 (see FIG. 12) in the range of, for example, approximately 10 to 500 microns peak-to-peak, and in some instances in the range of about 20 to about 200 microns at a predetermined vibratory frequency $f_0$ of, for example, 55.5 kHz. When the ultrasonic transducer 50 is activated, the piezoelectric-mechanical vibrations are transmitted through the acoustic horn 52 and the ultrasonic transmission waveguide 56 to reach the ultrasonic surgical blade 60, thereby providing vibration of the ultrasonic surgical blade 60 at the resonant ultrasonic frequency.

Thus, when tissue is clamped between the ultrasonic surgical blade 60 and the clamp arm 44, the ultrasonic vibration of the ultrasonic surgical blade 60 may simultaneously sever the tissue and denature the proteins in the adjacent cells and intercellular matrix of the tissue, thereby providing a coagulative effect with relatively little thermal spread. In some examples, an alternating electrical current (e.g., at radio frequencies (RF)), may also be provided through the ultrasonic surgical blade 60 and/or through electrode(s) (not shown) located on the tissue-engaging surfaces 46 of the clamp arm 44 to provide cauterization and additional tissue sealing functionality.

In various examples, a foot pedal or other switching device (not shown) operably connected to the generator 16 may be employed to control the application of electrical power from the generator 16 to the ultrasonic transducer 50. When power is applied to the ultrasonic transducer 50 by operation of a foot pedal or other switch arrangement, the acoustic system 80 may, for example, cause the ultrasonic surgical blade 60 to vibrate longitudinally along the central waveguide/shaft axis 61 (see FIGS. 11 and 12) at approximately 55.5 kHz, and the amount of longitudinal movement will vary proportionately with the amount of driving power (electrical current) applied, which may be adjustably selected by a surgeon or other operator of the ultrasonic surgical instrument 10.

When relatively high power is applied, the ultrasonic surgical blade 60 may be configured to move longitudinally in the range of about 40 to 100 microns at the ultrasonic vibrational rate. Such ultrasonic vibration of the blade 60 will generate heat as the blade contacts tissue, i.e., the acceleration of the ultrasonic surgical blade 60 through the tissue converts the mechanical energy of the moving ultrasonic surgical blade 60 to thermal energy in the localized tissue-contact area. This localized heat creates a narrow zone of coagulation, which will reduce or eliminate bleeding in small blood vessels, such as blood vessels less than one millimeter in diameter. The cutting efficiency of the ultrasonic surgical blade 60, as well as the degree of hemostasis, will vary with the level of driving power applied, the cutting rate or force applied by the surgeon to the blade 60 through the clamp arm 44, and the properties of the tissue type and the vascularity of the tissue.

Figure 16:
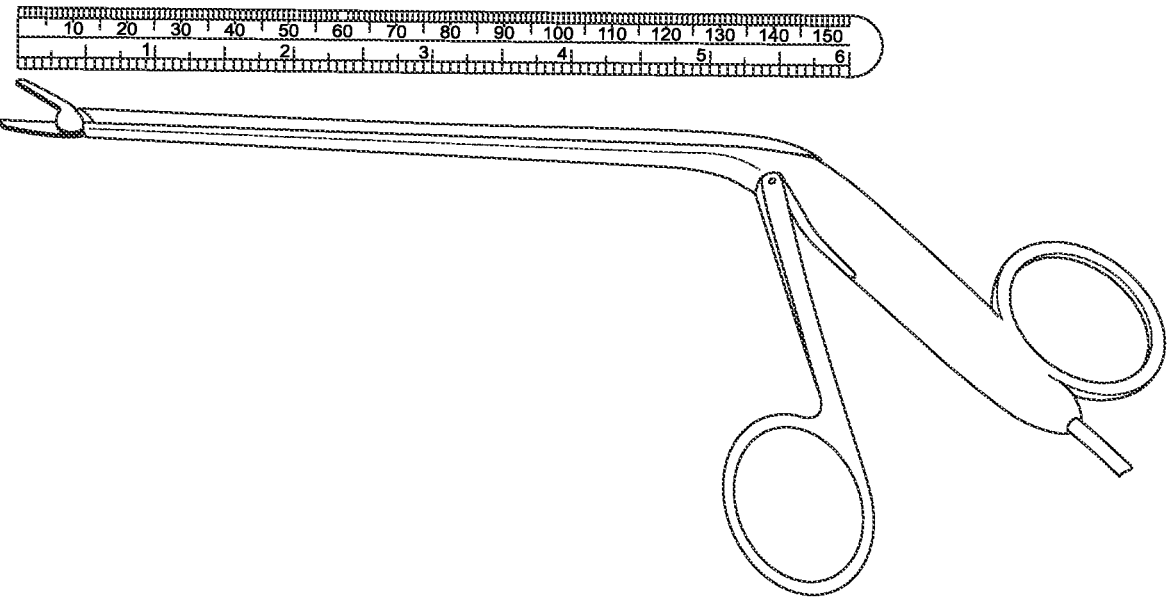
FIG. 16 is a drawing of a prototype ultrasonic surgical instrument comprising features shown in FIGS. 1-15.
Figure 17:
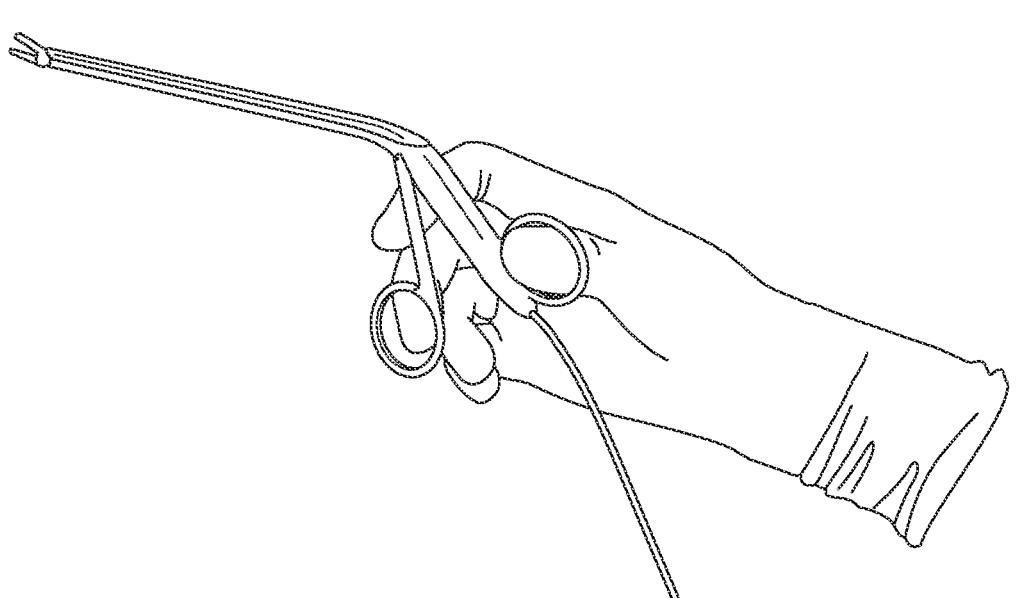
FIG. 17 is a drawing of the prototype ultrasonic surgical instrument shown in FIG. 16 in an open position in a surgeon's or other operator's hand.
Figure 18:
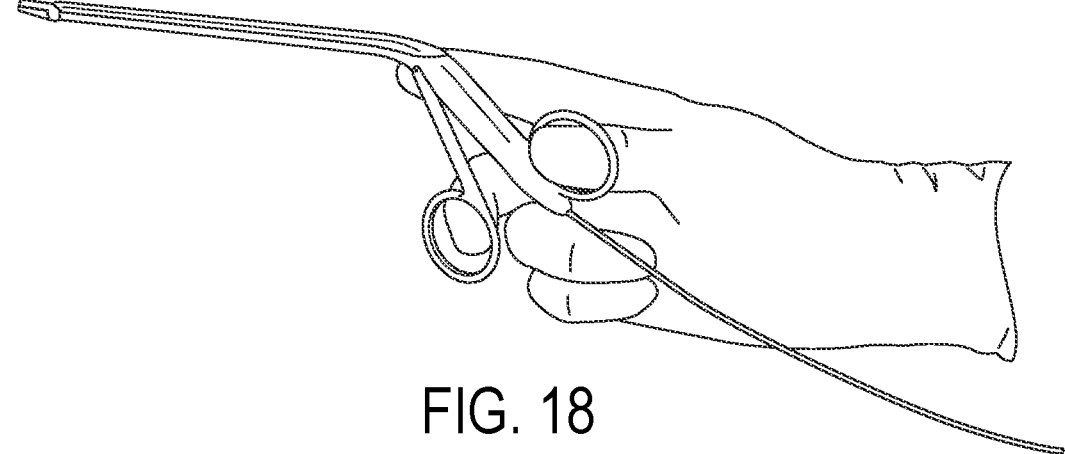
FIG. 18 is a drawing of the prototype ultrasonic surgical instrument shown in FIG. 17 in a closed position actuated by the surgeon's or other operator's hand.

Referring to FIGS. 16-18, a prototype ultrasonic surgical instrument is shown comprising the features shown in FIGS. 1-15 and described above. The prototype ultrasonic surgical instrument is shown in FIGS. 16 and 17 in an open position with the clamp arm pivoted away from the ultrasonic surgical blade, the reciprocating upper shaft member translated proximally, and the clamp actuation member pivoted away from the handle body (compare with FIG. 1). The prototype ultrasonic surgical instrument is shown in FIG. 18 in a closed position with the clamp arm pivoted toward the ultrasonic surgical blade, the reciprocating upper shaft member translated distally, and the clamp actuation member pivoted toward the handle body (compare with FIG. 5).

The ultrasonic surgical instrument 10 shown in FIGS. 1-15 (and the prototype shown in FIGS. 16-18) may facilitate improved surgical technique and execution in procedures where the surgical area is too small for the effective use of conventional scissor clamp ultrasonic devices. The angled scissor grip configuration of the ultrasonic surgical instrument 10 (provided by the angular off-set of the ultrasonic surgical blade 60 from the central transducer axis 51 of the ultrasonic transducer 50) moves the ultrasonic transducer 50 out of longitudinal alignment with the blade, which increases surgical site access, visibility, and manipulability because the shaft assembly 30 extends away from the operator's hand when grasping the handle assembly 20. In this manner, a surgeon or other operator can readily see the end-effector 40 without any obscuring or impairment of their line-of-sight by the location of the ultrasonic transducer 50 or by the location of their hand when grasping the instrument 10.

Figures 19, 20:
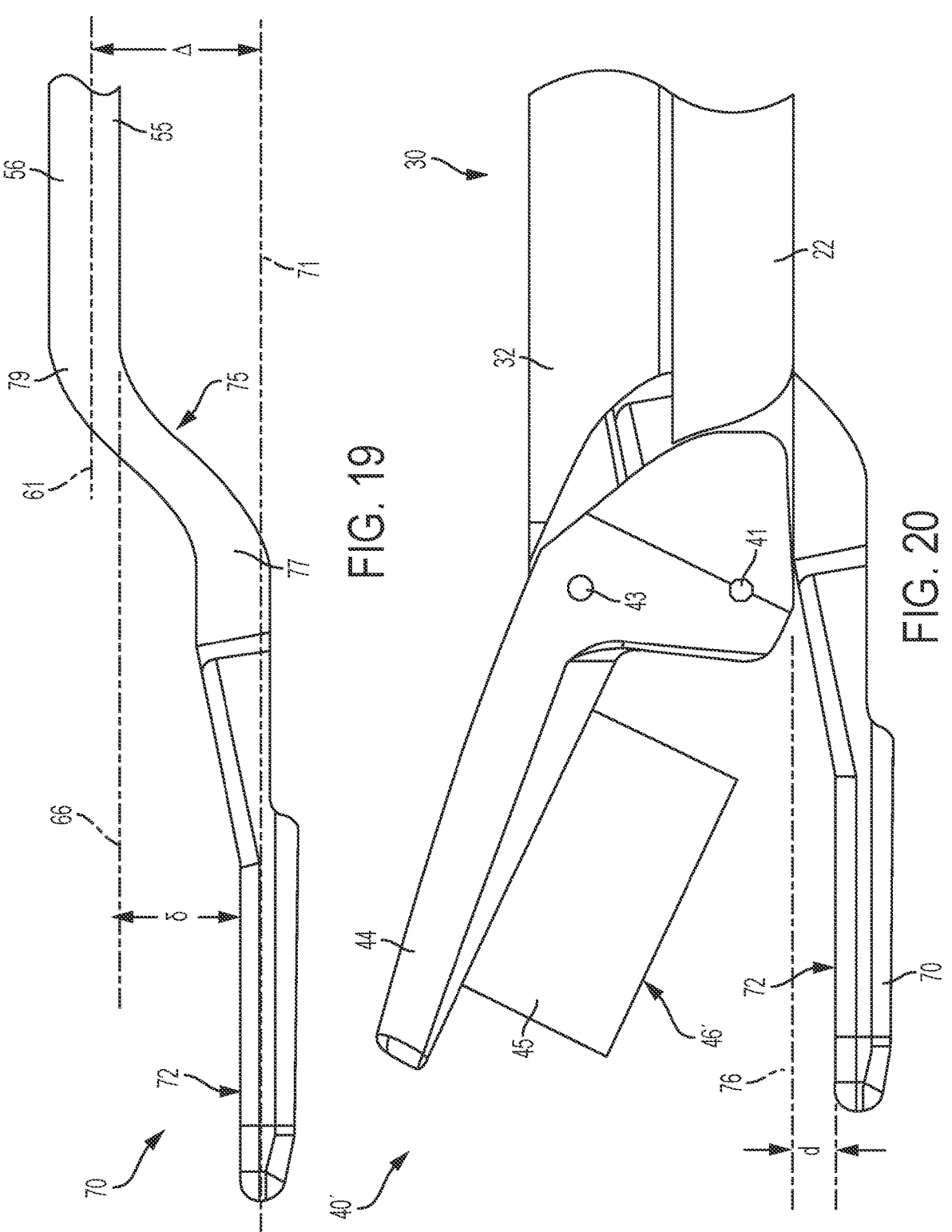
FIG. 19 is a side view schematic diagram of an ultrasonic surgical blade transversely off-set from an ultrasonic transmission waveguide through a compound curvature component connecting the ultrasonic surgical blade to the ultrasonic transmission waveguide.
FIG. 20 is a side view of an end-effector of an ultrasonic surgical instrument comprising the ultrasonic surgical blade shown in FIG. 19.

As shown in FIG. 12, the ultrasonic surgical blade 60 is aligned with the central waveguide/shaft axis 61. In some examples, it would be advantageous for an ultrasonic surgical blade to off-set transversely from the central waveguide/shaft axis 61. Referring to FIG. 19, an ultrasonic surgical blade 70 is shown transversely (linearly) off-set from the linear portion 55 of the ultrasonic transmission waveguide 56. The ultrasonic surgical blade 70 has a central blade axis 71 that is parallel to the central waveguide/shaft axis 61. The tissue-engaging surface 72 of the ultrasonic surgical blade 70 is parallel to the central blade axis 71, the central waveguide/shaft axis 61, and the lower surface (indicated by the line 66) of the linear portion 55 of the ultrasonic transmission waveguide 56.

The ultrasonic surgical blade 70 is coupled to the linear portion 55 of the ultrasonic transmission waveguide 56 through a compound curvature component 75. As used herein, the term "compound curvature component" means a transitional component of an acoustic system located between a distal ultrasonic surgical blade and a proximal ultrasonic transmission waveguide or other proximal component of an acoustic system (e.g., the distal end of an acoustic horn) comprising at least two bends along the length of the component. Still referring to FIG. 19, the compound curvature component 75 comprises a distal curved portion 77 and a proximal curved portion 79. The distal curved portion 77 of the compound curvature component 75 is coupled to the ultrasonic surgical blade 70. The proximal curved portion 79 of the compound curvature component 75 is coupled to the linear portion 55 of the ultrasonic transmission waveguide 56. Although the curved portions 77 and 79 are shown as smooth curves or bends in the material forming the compound curvature component 75, it is understood that any one or more of the at least two bends along the length of a compound curvature component can be shaped such that the compound curvature component comprises a J-shape. The shape of a compound curvature component can be generally defined using a spline function.

Still referring to FIG. 19, and as described above, the compound curvature component 75 transversely (linearly) off-sets the ultrasonic surgical blade 70 from the linear portion 55 of the ultrasonic transmission waveguide 56. The central blade axis 71 is transversely off-set from the central waveguide/shaft axis 61 by a linear distance A. As a result, the tissue-engaging surface 72 of the ultrasonic surgical blade is transversely off-set from the lower surface 66 of the linear portion 55 of the ultrasonic transmission waveguide 56 by a linear distance δ. The ultrasonic surgical blade 70 is therefore located off-axis relative to the ultrasonic transmission waveguide 56 (linearly off-axis relative to the linear portion 55, and angularly off-axis relative to the curved portion 54—see FIG. 11). The compound curvature component 75 may be connected to the linear portion 55 at a location that is distal to the most distal node in the ultrasonic transmission waveguide 56.

As illustrated in FIG. 20, the transversely (linearly) off-set ultrasonic surgical blade 70 and the compound curvature component 75 can be incorporated in place of the ultrasonic surgical blade 60 in the ultrasonic surgical instrument 10 shown in FIGS. 1-18. The end-effector 40' comprises the ultrasonic surgical blade 70 and the clamp arm 44 (for ease of illustration, an optional blade housing that surrounds the non-tissue-engaging surfaces of the ultrasonic surgical blade 70, but that exposes the tissue-engaging surface 72 of the ultrasonic surgical blade 70 for the cutting and coagulation of tissue during operation, is omitted from FIG. 20). As described above, the clamp arm 44 is pivotably coupled to the lower shaft member 22 of the shaft assembly 30 through a pivotable joint 41 (e.g., a cylindrical pin located within a pin aperture 41a in the clamp arm 44 and a pin aperture 41b in the distal end of the lower shaft member 22). The clamp arm 44 is also pivotably coupled to the reciprocating upper shaft member 32 of the shaft assembly 30 through a pivotable joint 43 (e.g., a cylindrical pin located within a pin aperture 43a in the clamp arm 44 and a pin aperture 43b in the distal end of the reciprocating upper shaft member 32). The clamp arm 44 actuates in the manner described above.

Still referring to FIG. 20, the tissue-engaging surface 72 of the ultrasonic surgical blade 70 is transversely off-set from the lower surface (indicated by line 76) of the lower shaft member 22 of the shaft assembly 30 by a linear distance (d). The ultrasonic surgical blade 70 is transversely off-set away from the central waveguide/shaft axis 61 and the clamp arm 44, while the tissue-engaging surface 72 remains parallel to the waveguide/shaft axis 61. In this manner, the ultrasonic surgical blade 70 is effectively stepped-down away from the clamp arm 44, which may improve surgical site visibility and ergonomics for a surgeon or other operator. The transverse off-set of the ultrasonic surgical blade 70 away from the waveguide/shaft axis 61 and the clamp arm 44 also allows for the optional use of a thicker clamp pad 45 (with tissue-engaging surface 46') than can be accommodated in an ultrasonic surgical instrument with an ultrasonic surgical blade that is not transversely off-set away from the clamp arm 44 (see, e.g., FIG. 13).

Figure 21:
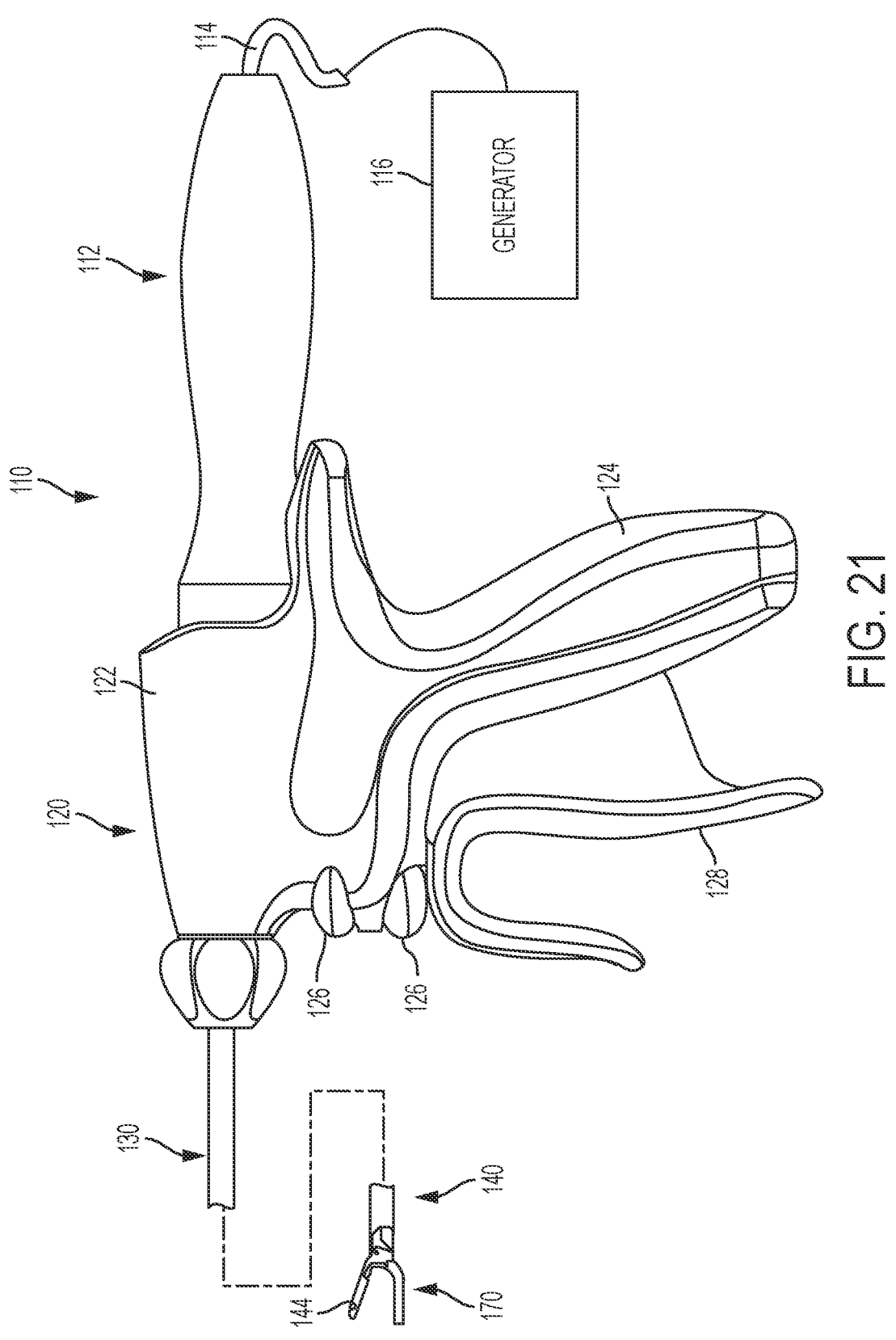
FIG. 21 is a side view of an ultrasonic surgical instrument having a tissue clamping mechanism, shown in an open position, with a pistol grip configuration and comprising an ultrasonic surgical blade that is transversely off-set from an ultrasonic transmission waveguide through a compound curvature component connecting the ultrasonic surgical blade to the ultrasonic transmission waveguide.

As described above, the examples of the ultrasonic surgical instrument 10 illustrated in FIGS. 1-20 comprise a scissor grip configuration. Although scissor grip configurations often provide excellent manual control of end-effector operation and haptic feedback from manipulated tissue, the ultrasonic surgical instruments described in this specification can be implemented using alternative configurations such as, for example, a pistol grip configuration. For example, FIG. 21 illustrates an ultrasonic surgical instrument 110 comprising a handle assembly 120, a shaft assembly 130, and an end-effector 140. As described, for example, in U.S. Patent Application Publication No. 2015/0148831, now U.S. Pat. No. 9,943,325, which is incorporated by reference into this specification, the shaft assembly 130 can comprise an outer sheath, an inner tube slidably disposed within the outer sheath, and a waveguide disposed within the inner tube. Longitudinal translation of the inner tube causes actuation of a clamp arm 144 at an end-effector 140. Still referring to FIG. 21, the handle assembly 120 comprises a body 122 including a pistol grip 124 and a pair of buttons 126. The handle assembly 120 also includes a trigger 128 that is pivotable toward and away from the pistol grip 124.

Still referring to FIG. 21, an ultrasonic transducer assembly 112 extends proximally from the body 122 of the handle assembly 120. It is understood, however, that the ultrasonic transducer assembly 112 can be located within the pistol grip 124, for example, in a manner analogous to the location of the ultrasonic transducer 50 within the handle body 24 of the handle assembly 20 of the ultrasonic surgical instrument 10 described above in connection with FIGS. 1-11. In such examples, the ultrasonic transducer assembly 112 is structured and configured as part of an acoustic system analogous to the acoustic system 80 shown in FIG. 11, wherein the central axis of an ultrasonic surgical blade 170 and the central axis of the shaft assembly 130 are both angularly off-set from the central transducer axis of the ultrasonic transducer assembly 112 located within the pistol grip 124. The transducer assembly 112 is coupled to a generator 116 via a cable 114 and may operate and comprise the features and characteristics described above.

The end-effector 140 comprises an ultrasonic surgical blade 170 and a clamp arm 144. The end-effector 140 may comprise features and characteristics described above in connection with end-effectors 40 and 40' (see, e.g., FIGS. 13-15 and 20). An operator may activate buttons 126 to selectively activate the ultrasonic transducer assembly 112 to activate the ultrasonic surgical blade 170. In the illustrated example, the ultrasonic surgical instrument 110 is activated by two buttons 126—one for activating the ultrasonic surgical blade 170 at a lower power and another for activating the ultrasonic surgical blade 170 at a higher power. However, it is understood that any other operable number of buttons, alternative activation devices, and/or selectable power levels may be implemented. For instance, a foot pedal may be provided to selectively activate the ultrasonic transducer assembly 112.

The buttons 126 are located such that an operator may readily fully operate the ultrasonic surgical instrument 110 with a single hand. For instance, the operator may position their thumb about the pistol grip 124, position their middle, ring, and/or little finger(s) about the trigger 128, and manipulate the buttons 126 using their index finger. In operation, pivoting the trigger 128 toward the pistol grip 124 causes the clamp arm 144 to pivot toward the ultrasonic surgical blade 170, thereby closing the end-effector 144. Conversely, pivoting the trigger 128 away from the pistol grip 124 causes the clamp arm 144 to pivot away from the ultrasonic surgical blade 170, thereby opening the end-effector 144.

The example ultrasonic surgical instruments described above (10/100) comprise either a scissor grip or a pistol grip configuration to actuate an end-effector (40/40'/140) comprising a clamp arm (44/144) and an ultrasonic surgical blade (60/70/170) that is off-set angularly and/or linearly to provide an off-axis configuration (relative to the central transducer axis and/or the central waveguide/shaft axis). However, off-set ultrasonic surgical blade may be advantageous in ultrasonic surgical instruments comprising end-effectors having unencumbered ultrasonic surgical blades without clamping functionality.

Figure 22:
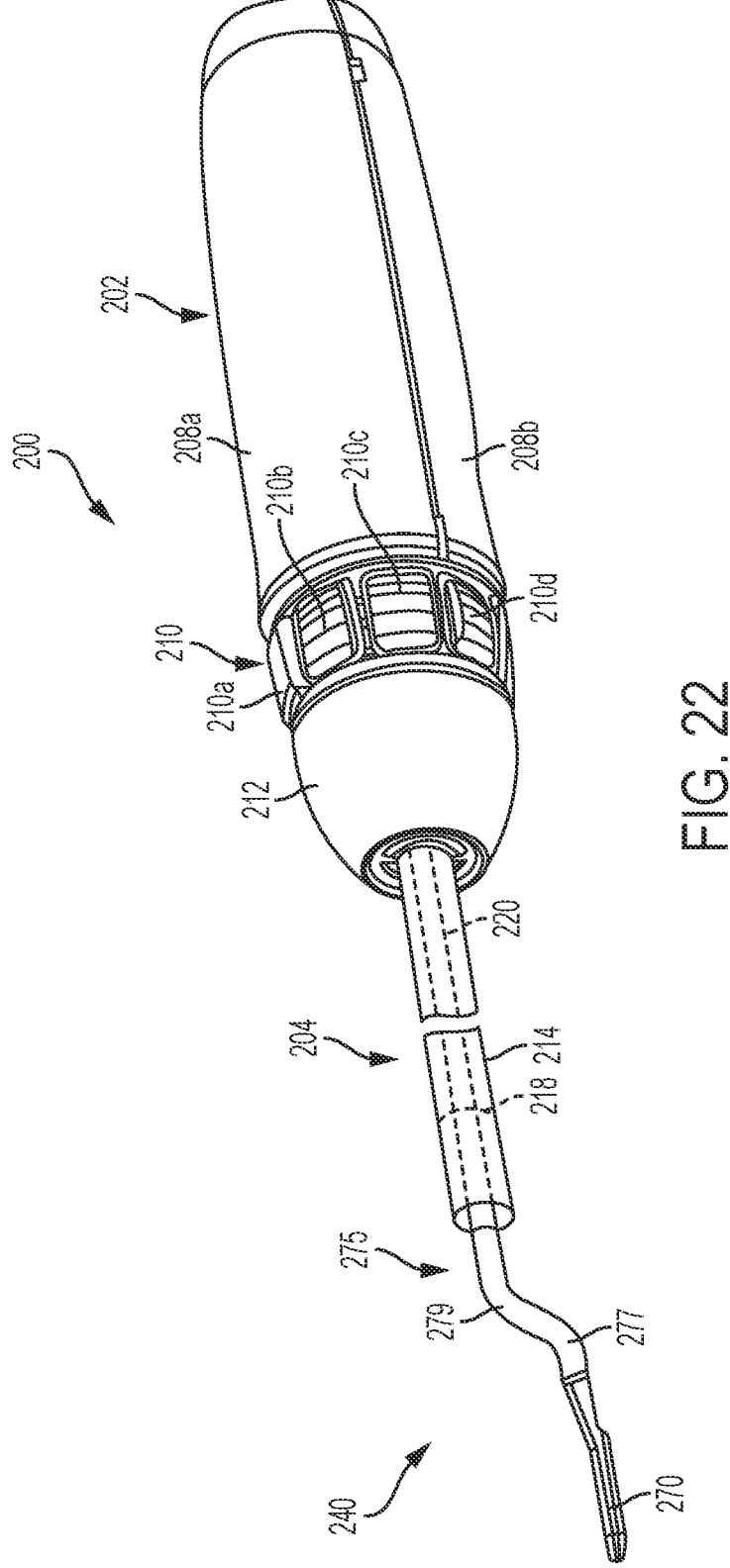
FIG. 22 is a perspective view of an ultrasonic surgical instrument without a tissue clamping mechanism and comprising an ultrasonic surgical blade that is transversely off-set from an ultrasonic transmission waveguide through a compound curvature component connecting the ultrasonic surgical blade to the ultrasonic transmission waveguide.

Referring to FIG. 22, an ultrasonic surgical instrument 200 comprises a handle assembly 202, a shaft assembly 204, and a surgical end-effector 240. The handle assembly 202 comprises a first shroud 208a and a second shroud 208b, an activation button assembly 210, and a nose cone 212. The activation button assembly 210 comprises a plurality of activation buttons 210a-210d distributed about the handle assembly 202. The shaft assembly 204 comprises an outer sheath 214. The end-effector 240 comprises an ultrasonic surgical blade 270 connected to an ultrasonic transmission waveguide 220 through a compound curvature component 275. The ultrasonic surgical blade 270 is transversely (linearly) off-set from the ultrasonic transmission waveguide 220 and the shaft assembly 204 (including the outer sheath 214). The ultrasonic transmission waveguide 220 is isolated from the outer sheath 214 with multiple isolation spacers 218, which can be overmolded over the ultrasonic transmission waveguide 220.

The handle assembly 202 also comprises an ultrasonic transducer (not shown) located within the handle assembly 202 and acoustically coupled to the ultrasonic transmission waveguide 220, which in turn is acoustically coupled to the ultrasonic surgical blade 270 through the compound curvature component 275. The handle assembly 202 is electrically connected to an ultrasonic energy generator (not shown), which can be activated by one of the plurality of activation buttons 210a-210d, for example the activation button 210a. Depressing the activation button 210a activates the ultrasonic generator and delivers electrical energy to the ultrasonic transducer located in the handle assembly 202. The ultrasonic transducer in the handle assembly 202 converts the electrical energy to ultrasonic vibratory motion, which is acoustically coupled to the ultrasonic transmission waveguide 220, the compound curvature component 275, and the ultrasonic surgical blade 270. The ultrasonic surgical blade 270 vibrates, for example, at a frequency of approximately 55.5 kilohertz and a peak-to-peak displacement of 10 to 500 microns, as described above.

Figure 23:
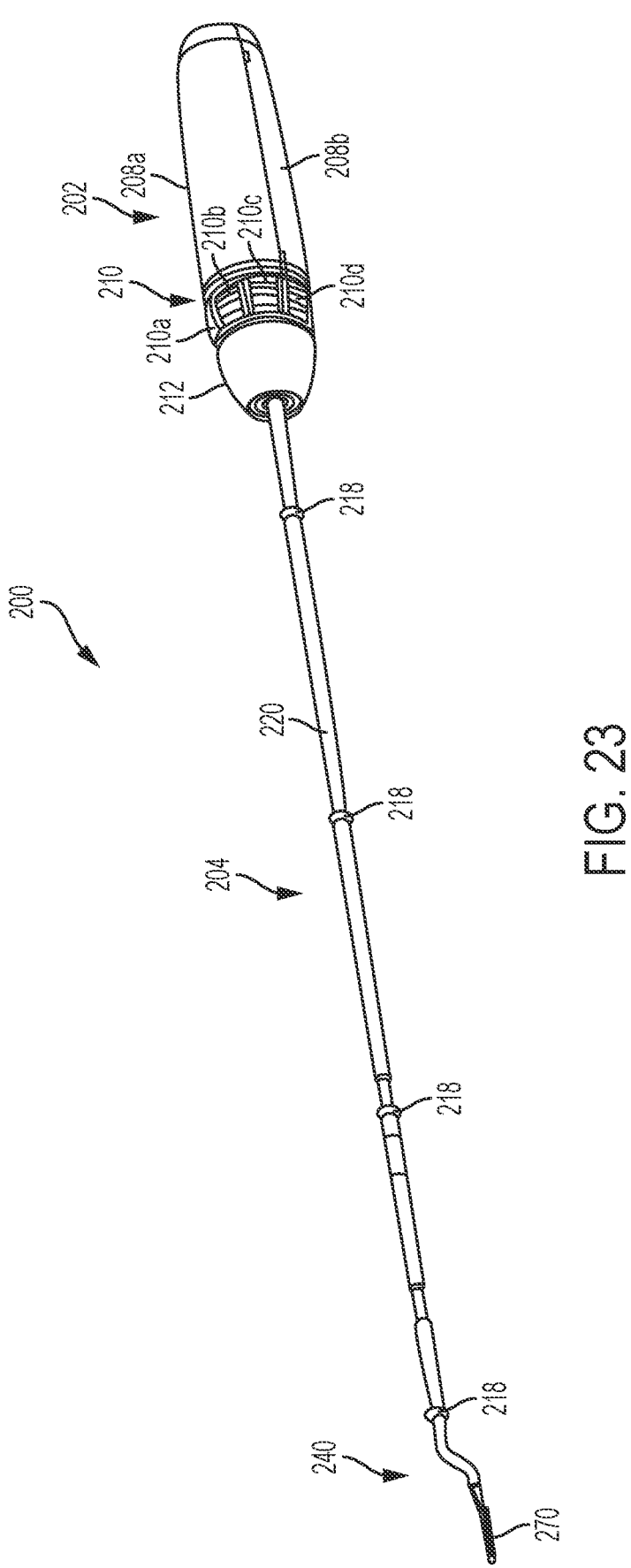
FIG. 23 is a perspective view of an ultrasonic surgical instrument comprising an ultrasonic surgical blade that is transversely off-set from an ultrasonic transmission waveguide through a compound curvature component connecting the ultrasonic surgical blade to the ultrasonic transmission waveguide.

FIG. 23 shows the ultrasonic surgical instrument 200 shown in FIG. 23 with the outer sheath 214 removed to reveal the underlying ultrasonic transmission waveguide 220. The isolation spacers 218 are located over the ultrasonic transmission waveguide 220 to acoustically isolate the outer sheath 214 from the ultrasonic transmission waveguide 220. Accordingly, the plurality of isolation spacers 218 are located on respective nodes along the ultrasonic transmission waveguide 220 to minimize the vibrations acoustically coupled to the outer sheath 214. In one example, the isolation spacers 218 may be overmolded over the ultrasonic transmission waveguide 220.

Figure 24:
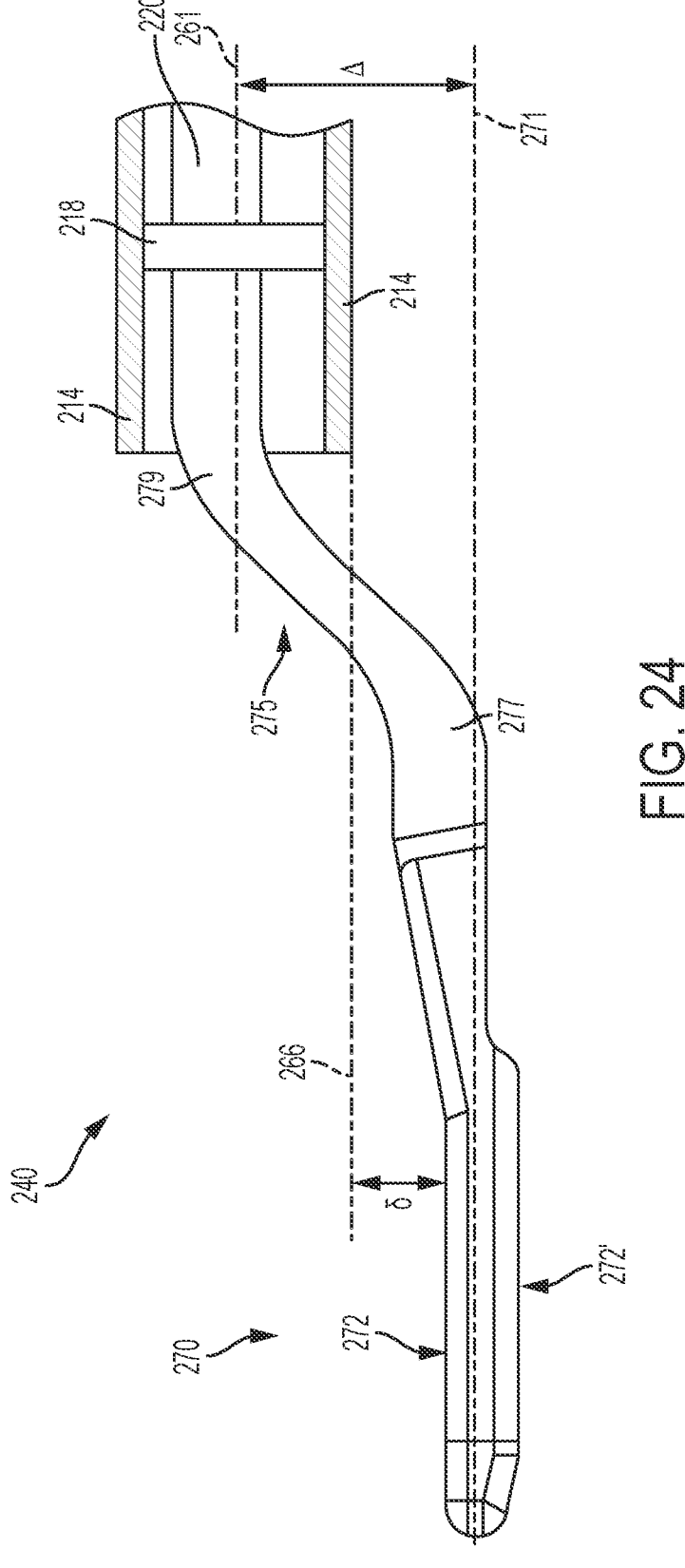
FIG. 24 is a side view schematic diagram, partially in cross-section, of an ultrasonic surgical blade that is transversely off-set from an ultrasonic transmission waveguide through a compound curvature component connecting the ultrasonic surgical blade to the ultrasonic transmission waveguide, wherein the ultrasonic transmission waveguide is located within a sheath.

Referring to FIG. 24, the ultrasonic surgical blade 270 is transversely (linearly) off-set from the ultrasonic transmission waveguide 220. The ultrasonic surgical blade 270 is coupled to the ultrasonic transmission waveguide 220 through a compound curvature component 275. The compound curvature component 275 comprises a distal curved portion 277 and a proximal curved portion 279. The distal curved portion 277 of the compound curvature component 275 is coupled to the ultrasonic surgical blade 270. The proximal curved portion 279 of the compound curvature component 275 is coupled to the ultrasonic transmission waveguide 220. Although the curved portions 277 and 279 are shown as smooth curves or bends in the material forming the compound curvature component 275, it is understood that any one or more of the at least two bends along the length of a compound curvature component can be shaped such that the compound curvature component comprises a J-shape. The shape of a compound curvature component can be generally defined using a spline function. The compound curvature component 275 may be coupled to the ultrasonic transmission waveguide 220 at a location that is distal to the most distal node in the ultrasonic transmission waveguide 220.

Still referring to FIG. 24, the compound curvature component 275 transversely off-sets the ultrasonic surgical blade 270 from the ultrasonic transmission waveguide 220. The ultrasonic surgical blade 270 defines a central blade axis 271 that is parallel to the central waveguide/shaft axis 261. The tissue-engaging surface 272 of the ultrasonic surgical blade 270 is parallel to the central blade axis 271, and the central waveguide/shaft axis 261, and the outer surface (indicated by the line 266) of the outer sheath 214. The central blade axis 271 is transversely off-set from the central waveguide/shaft axis 261 by a linear distance A. As a result, the tissue-engaging surface 272 is transversely off-set from the outer surface 266 of the ultrasonic transmission waveguide 220 by a linear distance δ. The ultrasonic surgical blade 270 is therefore located off-axis relative to the ultrasonic transmission waveguide 220 and the outer sheath 214.

The ultrasonic surgical blade 270 comprises a tissue-engaging surface 272 facing inwardly toward the central waveguide/shaft axis 261. Alternatively, or additionally, the ultrasonic surgical blade 270 may optionally comprise a tissue-engaging surface 272' facing outwardly away from the central waveguide/shaft axis 261. Because the ultrasonic surgical instrument 200 comprises an unencumbered ultrasonic surgical blade 270, and the end-effector 240 does not comprise clamping functionality, the presence of two or more tissue-engaging surfaces 272 and 272' on the ultrasonic surgical blade 270 may increase the functionality of the ultrasonic surgical instrument 200 during surgical operations.

Figure 25:
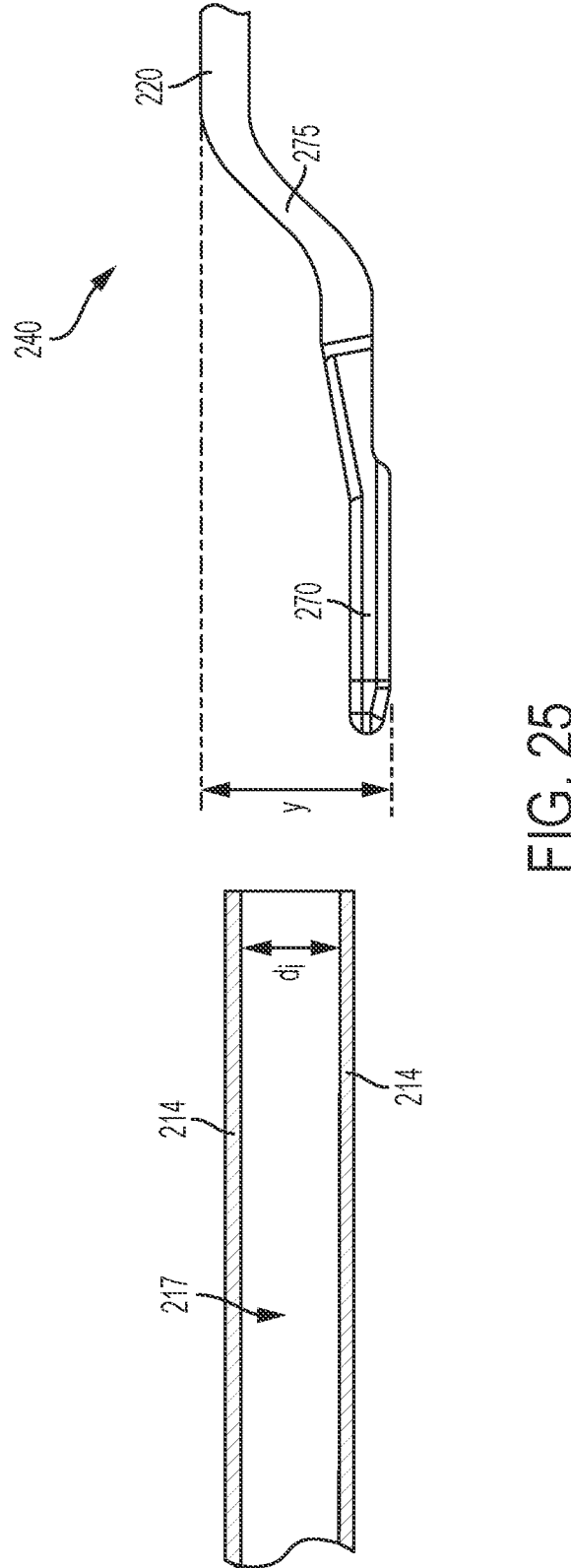
FIG. 25 is a side view schematic diagram, partially in cross-section, showing the mechanical interference caused by the size difference between a small diameter sheath and an ultrasonic surgical blade that is transversely off-set from an ultrasonic transmission waveguide through a compound curvature component connecting the ultrasonic surgical blade to the ultrasonic transmission waveguide.

The transverse off-set of the ultrasonic surgical blade 270 from the ultrasonic transmission waveguide 220 through the compound curvature component 275 increases the effective transverse size of the end-effector 240. Referring to FIG. 25, the effective transverse size (y) of the end-effector 240 may be larger than the inside diameter $(d_i)$ of the outer sheath 214. The relative size difference between the inside diameter $(d_i)$ of the outer sheath 214 and the effective transverse size (y) of the end-effector 240 may create mechanical interference that prevents the positioning of the ultrasonic transmission waveguide 220 within the lumen 217 of the outer sheath 214 because the inside diameter $(d_i)$ is too small to accommodate the effective transverse size (y). As a result, the assembly and manufacture of ultrasonic surgical instruments, such as instruments 110 and 200 that comprise a transversely off-set ultrasonic surgical blade connected to an ultrasonic transmission waveguide located within an outer sheath, may be problematic, particularly where the ultrasonic transmission waveguide, the distally-coupled compound curvature component, and proximally-coupled components (e.g., an acoustic horn having an effective transverse size greater than $d_i$) are formed from a single piece of material (e.g., machined from metal or alloy rod or bar stock).

Additionally, in surgical applications where the surgical sites are relatively small and/or awkwardly located (e.g., transcranial, ear-nose-throat, or neck surgeries), it is advantageous to minimize the cross-sectional size of the ultrasonic transmission waveguide and the outer sheath, which further increases the size difference between the inner diameter of the outer sheath and the effective transverse size of an end-effector. Examples of slotted sheath assemblies are described below which address the assembly and manufacturing issues created by size differences between the inner diameter of an outer sheath and the effective transverse size of an end-effector comprising a transversely off-set ultrasonic surgical blade. Slotted sheath assemblies, examples of which are illustrated in FIGS. 26-42, may be used with end-effectors comprising a transversely off-set ultrasonic surgical blade, such as end-effector 240, in ultrasonic surgical instruments having unencumbered ultrasonic surgical blades without clamping functionality, or in ultrasonic surgical instruments with clamping functionality and comprising, for example, either a scissor grip or a pistol grip configuration, such as the ultrasonic surgical instruments described above (10/110/200).

Figure 26:
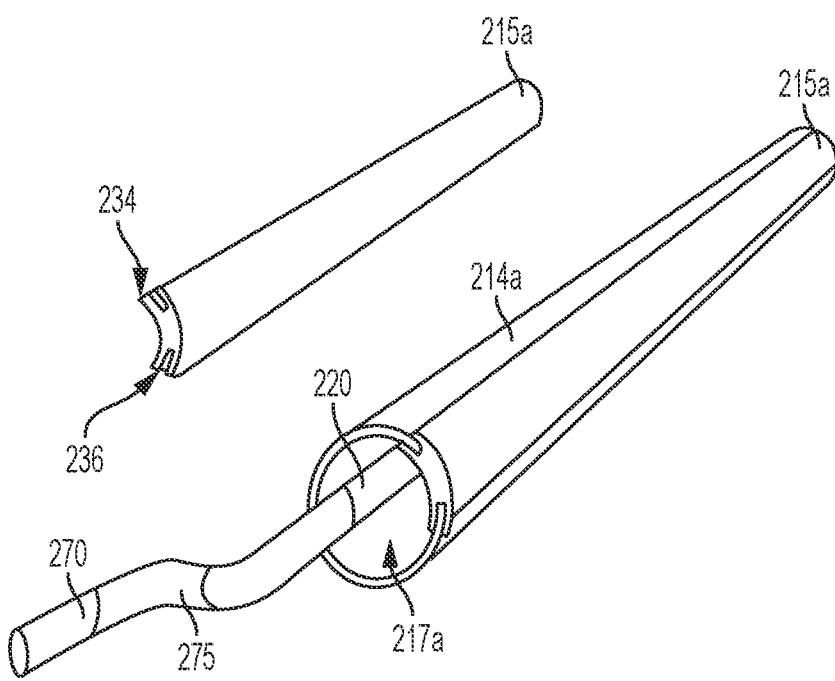
FIG. 26 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 27:
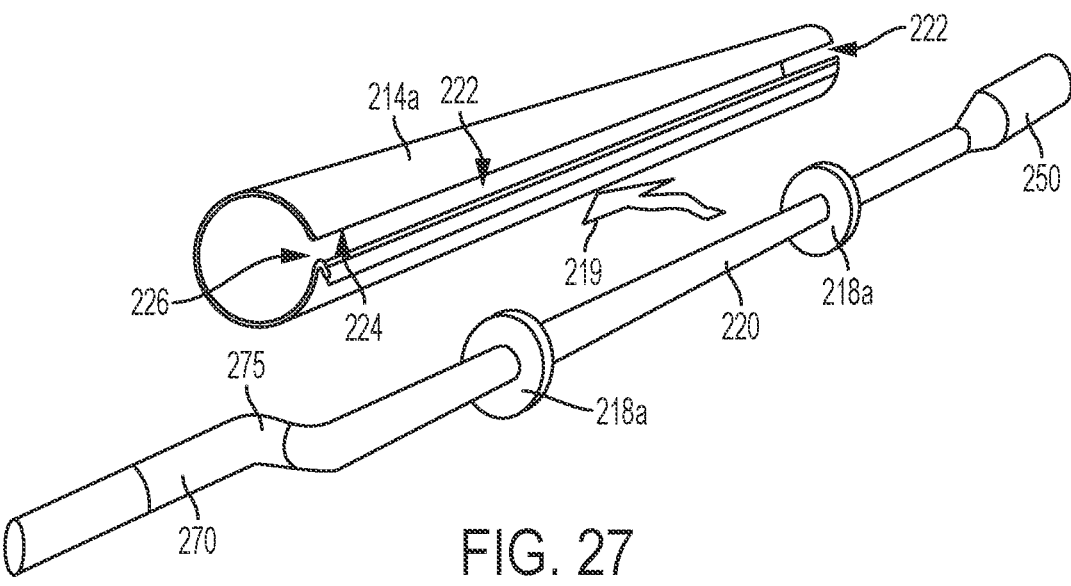
FIG. 27 is an exploded perspective view schematic diagram of the assembly shown in FIG. 26.

Referring to FIGS. 26 and 27, an acoustic system comprises an ultrasonic transducer 250, an ultrasonic transmission waveguide 220 acoustically coupled to the ultrasonic transducer 250, and an ultrasonic surgical blade 270 acoustically coupled to and transversely off-set from the ultrasonic transmission waveguide 220 through a compound curvature component 275. The proximally-coupled ultrasonic transducer 250 and the distally-coupled compound curvature component 275 prevent the ultrasonic transmission waveguide 220 and overmolded isolation spacers 218a from being inserted into a circumferentially closed sheath, as described above (see FIG. 25).

Still referring to FIGS. 26 and 27, a sheath 214a comprises an open slot 222 extending longitudinally along the proximal-distal length of the sheath 214a. The slot 222 comprises longitudinal edges 224 and 226. The sheath 214a may be made of compliant material having elastic properties (e.g., a thermoplastic material such as polytetrafluoroethylene (TEFLON) or a metallic material such as aluminum or stainless steel, for example) that permit the width of the slot 222 to be increased so that the ultrasonic transmission waveguide 220 and the isolation spacers 218a can be inserted into the lumen 217a of the sheath 214a, as indicated by the arrow 219, without the need to insert either the ultrasonic transducer 250 or the compound curvature component 275 and the ultrasonic surgical blade 270 through the lumen 217a of the sheath 214a. A sealing member 215a is then inserted into the slot 222 of the sheath 214a to bridge the slot 222, circumferentially close the sheath 214a, and seal the ultrasonic transmission waveguide 220 and the isolation spacers 218a within the lumen 217a of the sheath 214a.

The sealing member 215a comprises closed slots 234 and 236 in the longitudinal edges of the sealing member 215a and extending along the proximal-distal length of the sealing member 215a. When the sealing member 215a is inserted into the slot open 222 of the sheath 214a, the longitudinal edges 224 and 226 of the open slot 222 are secured within the closed slots 234 and 236 in the longitudinal edges of the sealing member 215a, as shown in FIG. 26. The mutual engagement of the edges 224 and 226 and the slots 234 and 236 secure the sealing member 215a in place within the slot 222, thereby bridging the slot 222, circumferentially closing the sheath 214a, and sealing the ultrasonic transmission waveguide 220 and the isolation spacers 218a within the lumen 217a of the sheath 214a. In some examples, the sealing member 215a may be made of an elastomer material (e.g., a silicone rubber material). In some examples, both the sealing member 215a and the isolation spacers 218a may be made of an elastomer material (e.g., a silicone rubber material).

Figure 28:
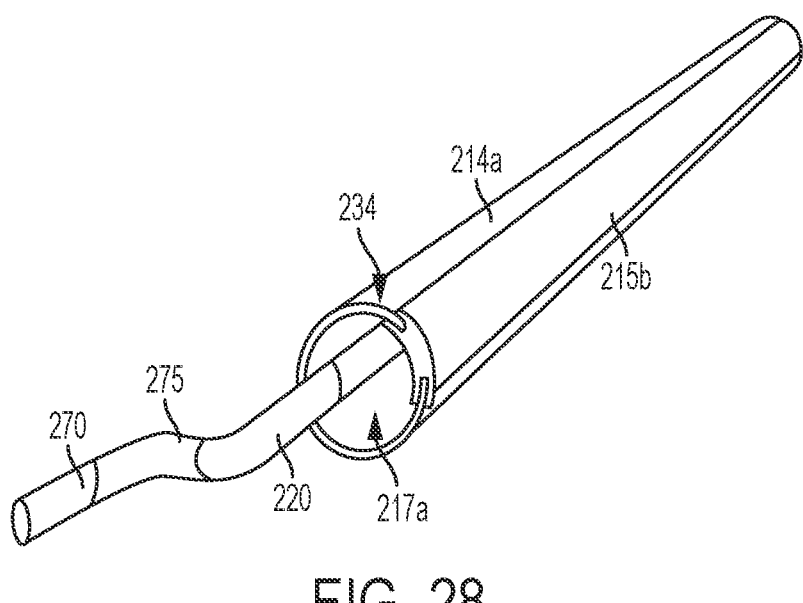
FIG. 28 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 29:
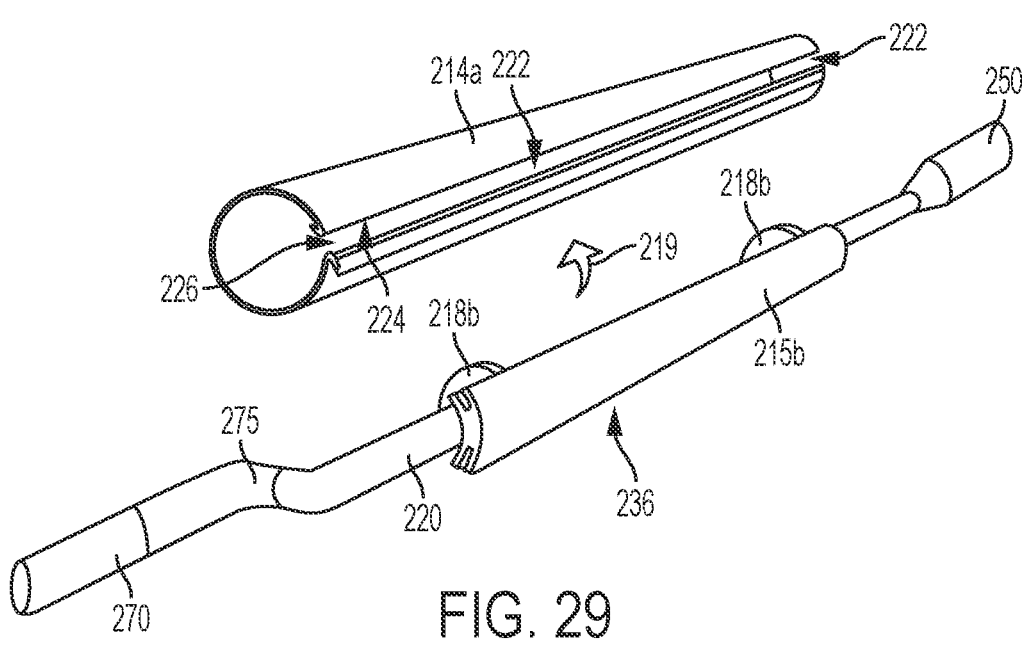
FIG. 29 is an exploded perspective view schematic diagram of the assembly shown in FIG. 28.

Referring to FIGS. 28 and 29, an alternative example is shown in which the isolation spacers 218b and the sealing member 215b are overmolded on the ultrasonic transmission waveguide 220 as a single, integral component. The ultrasonic transmission waveguide 220, the isolation spacers 218b, and the sealing member 215b are simultaneously inserted into the sheath 214a as a single assembly, as indicated by the arrow 219, without a need to insert either the ultrasonic transducer 250 or the compound curvature component 275 and the ultrasonic surgical blade 270 through the lumen 217a of the sheath 214a. When the sealing member 215b is inserted into the slot 222 of the sheath 214a, the longitudinal edges 224 and 226 of the slot 222 are secured within the slots 234 and 236 in the longitudinal edges of the sealing member 215b, as shown in FIG. 28. The mutual engagement of the edges 224 and 226 and the slots 234 and 236 secure the sealing member 215b in place within the slot 222, thereby bridging the slot 222, circumferentially closing the sheath 214a, and sealing the ultrasonic transmission waveguide 220 and the isolation spacers 218b within the lumen 217a of the sheath 214a.

Referring to FIGS. 30 and 31, an alternative example is shown in which a shrinkable tube 230 is provided instead of a sealing member 215a/215b. The ultrasonic transmission waveguide 220 and the isolation spacers 218a are inserted through the slot 222 and into the lumen 217a of the sheath 214a, as indicated by the arrow 219, without a need to insert either the ultrasonic transducer 250 or the compound curvature component 275 and the ultrasonic surgical blade 270 through the lumen 217a of the sheath 214a. The shrinkable tube 230 is then positioned over the outer circumference of the sheath 214a and shrunk to circumferentially seal the ultrasonic transmission waveguide 220 and the isolation spacers 218a within the lumen 217a of the sheath 214a. Although not shown in FIG. 30, it is understood that the shrinking of the tube 230 may impart sufficient to circumferential force to the sheath 214a to circumferentially deform the sheath 214a and bring the longitudinal edges 224 and 226 of the slot 222 into contact with each other, thereby eliminating the slot 222 and circumferentially closing the sheath 214a. The shrinkable tube 230 may be made of a heat-shrinkable material such as a crosslinked polyolefin (e.g., heat-shrinkable polyethylene, polypropylene, or poly (ethylene-propylene) copolymers).

Figure 32:
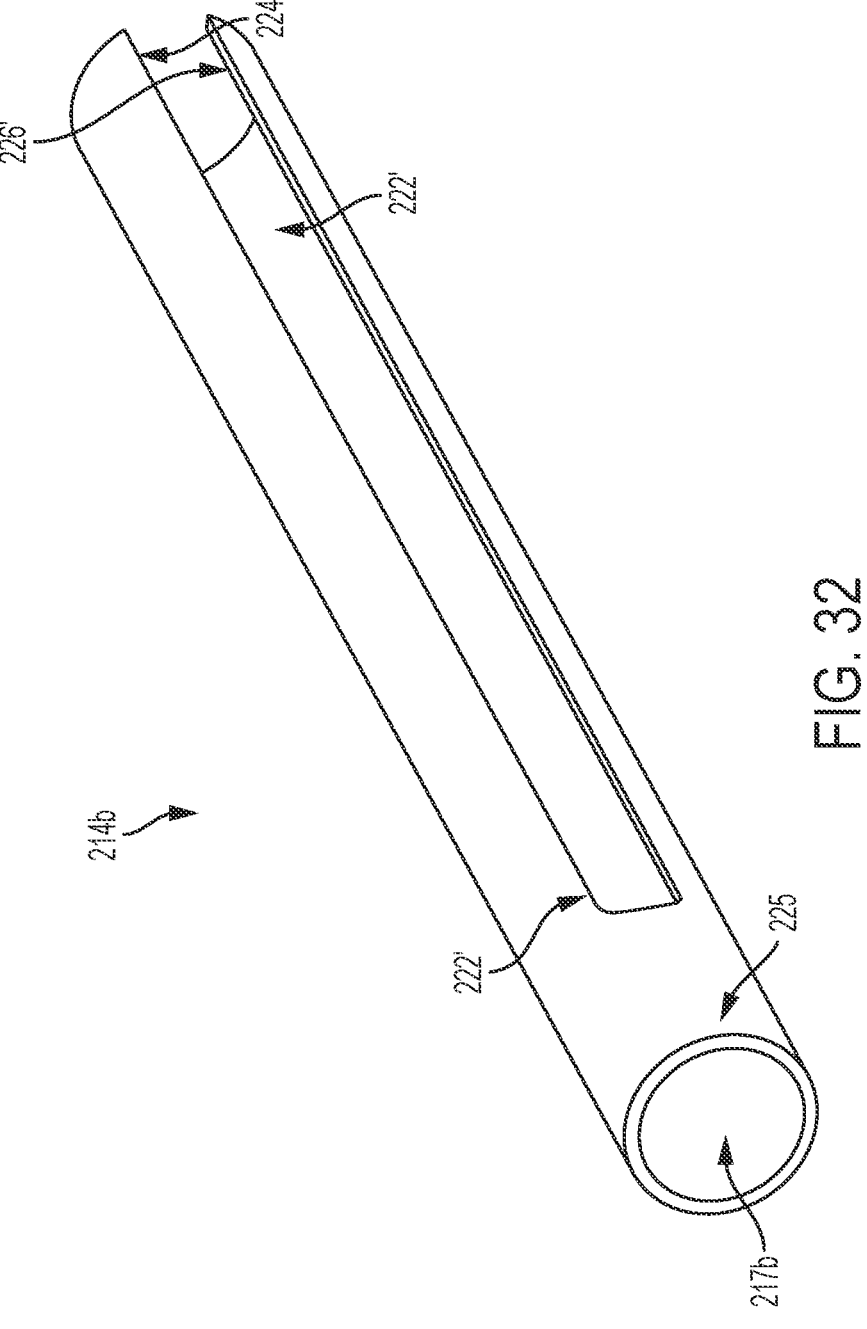
FIG. 32 is a perspective view schematic diagram of a sheath comprising a slot forming an opening located along a portion of the sheath length.

Referring to FIG. 32, an alternative example of a slotted sheath (214b) is shown, which may be used in place of the slotted sheath 214a in the examples illustrated in FIGS. 26-31. The sheath 214b comprises an open slot 222' extending longitudinally along a portion of the proximal-distal length of the sheath 214a. The sheath 214b comprises a fully-closed circumferential portion 225 at the distal end of the sheath 214b. Therefore, the slot 222' and the longitudinal edges 224' and 226' of the slot 222' only extend along a proximal portion of the total length of the sheath 214b. The fully-closed circumferential portion 225 may provided increased hoop strength to the sheath 214b.

Figures 33, 34:
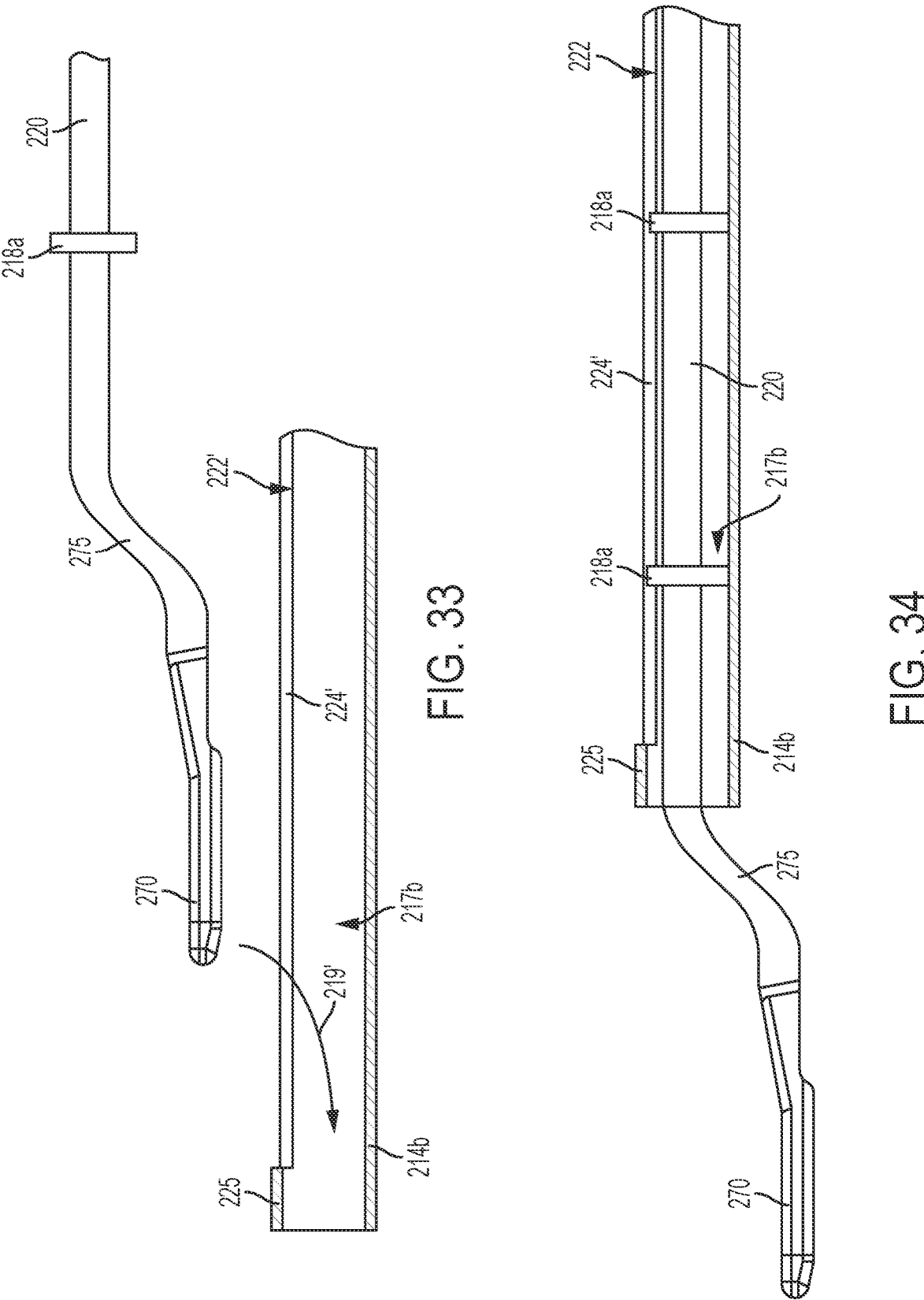
FIG. 33 is a side view schematic diagram, partially in cross-section, of an ultrasonic surgical blade, ultrasonic transmission waveguide, and sheath assembly, in a disassembled configuration, showing the positioning of the ultrasonic surgical blade into the sheath, wherein the ultrasonic surgical blade is transversely off-set from the ultrasonic transmission waveguide through a compound curvature component connecting the ultrasonic surgical blade to the ultrasonic transmission waveguide, and wherein the sheath comprises a slot forming an opening located along a portion of the sheath length.
FIG. 34 is a side view schematic diagram, partially in cross-section, showing the assembly illustrated in FIG. 33 in an assembled configuration.

Referring to FIGS. 33 and 34, the ultrasonic surgical blade 270, the compound curvature component 275, the ultrasonic transmission waveguide 220, and the isolation spacers 218a can be inserted through the slot 222' into the lumen 217b of the sheath 214b, as indicated by the arrow 219'. The ultrasonic surgical blade 270 and the compound curvature component 275 are inserted through the fully-closed circumferential portion 225. A sealing member 215a/215b (not shown, but see FIGS. 26-29) is then inserted into the slot 222' of the sheath 214b to bridge the slot 222', circumferentially close the sheath 214b, and seal the ultrasonic transmission waveguide 220 and the isolation spacers 218a within the lumen 217b of the sheath 214b. Alternatively, shrinkable tube 230 (not shown) is then positioned over the outer circumference of the sheath 214b and shrunk to circumferentially seal the ultrasonic transmission waveguide 220 and the isolation spacers 218a within the lumen 217b of the sheath 214b.

Figures 35, 36A, 36B:
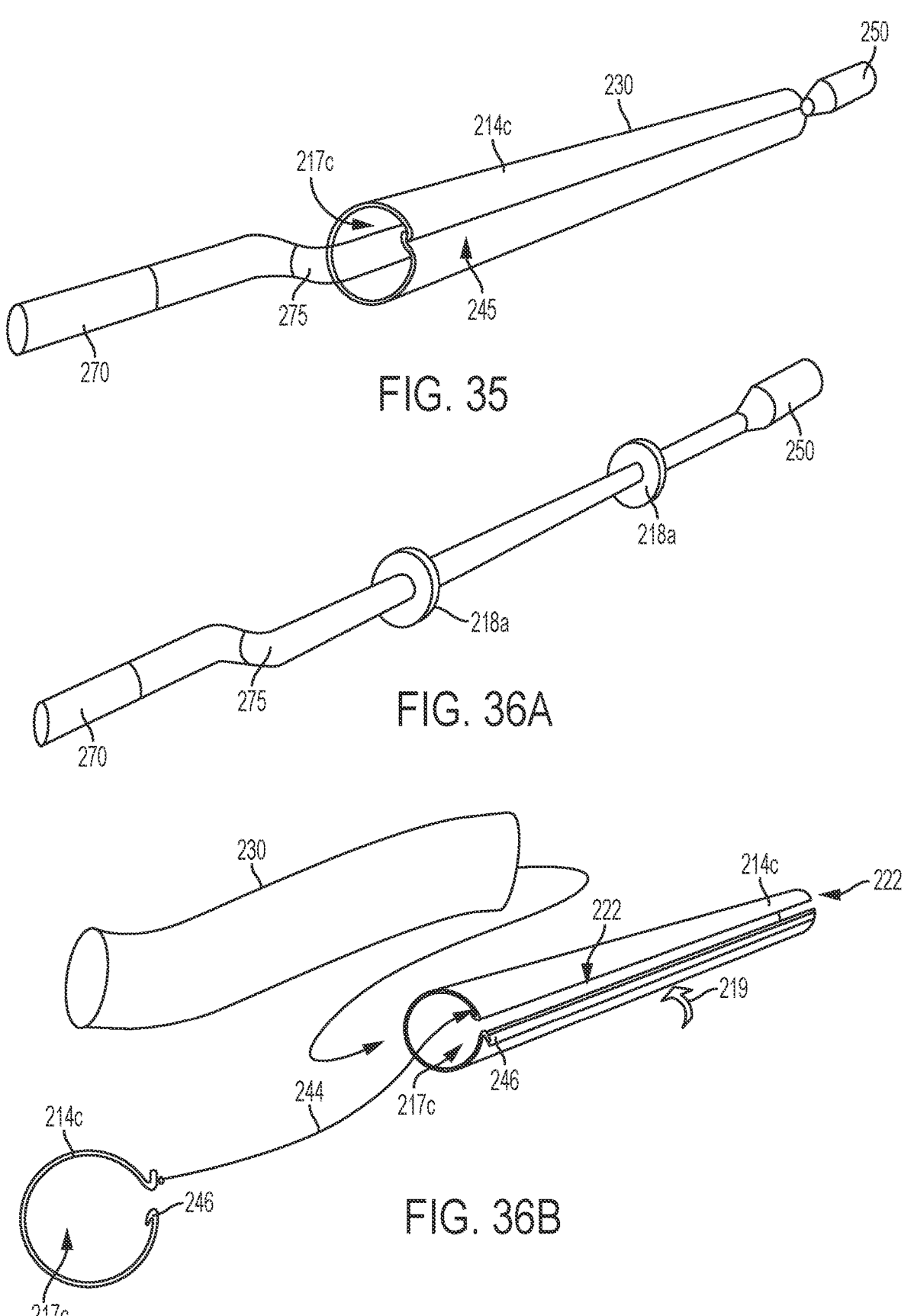
FIG. 35 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
FIG. 36A is an exploded perspective view schematic diagram of the assembly shown in FIG. 35.
FIG. 36B is an end view schematic diagram of the sheath shown in FIG. 36A.

Referring to FIGS. 35, 36A, and 36B, a sheath 214c comprises an open slot 222 extending longitudinally along the proximal-distal length of the sheath 214c. The slot 222 comprises crimped edges 244 and 246 along the length of the slot 222. The ultrasonic transmission waveguide 220 and the isolation spacers 218a are inserted into the lumen 217C of the sheath 214C, as indicated by the arrow 219, without a need to insert either the ultrasonic transducer 250 or the compound curvature component 275 and the ultrasonic surgical blade 270 through the lumen 217c of the sheath 214c. The circumference of the sheath 214c is then compressed until the crimped edges 244 and 246 meet and interlock to form a crimpled edge seam 245, as shown in FIG. 35, which closes the slot 222. A shrinkable tube 230 is then positioned over the outer circumference of the sheath 214c and shrunk to circumferentially seal the ultrasonic transmission waveguide 220 and the isolation spacers 218a within the lumen 217c of the sheath 214c.

Figure 37:
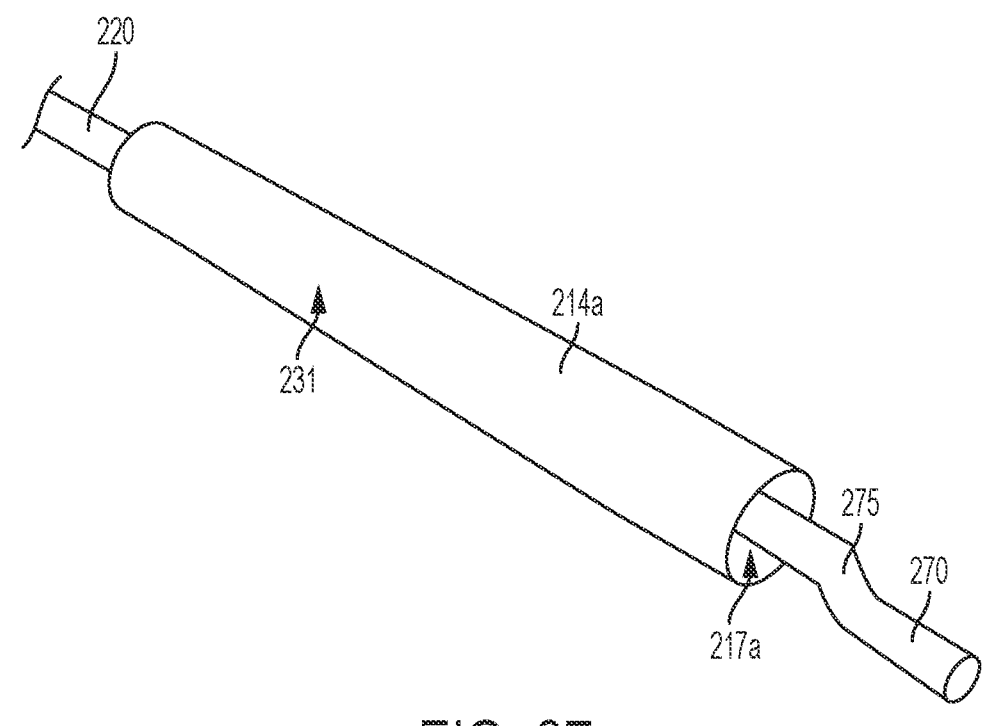
FIG. 37 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 38:
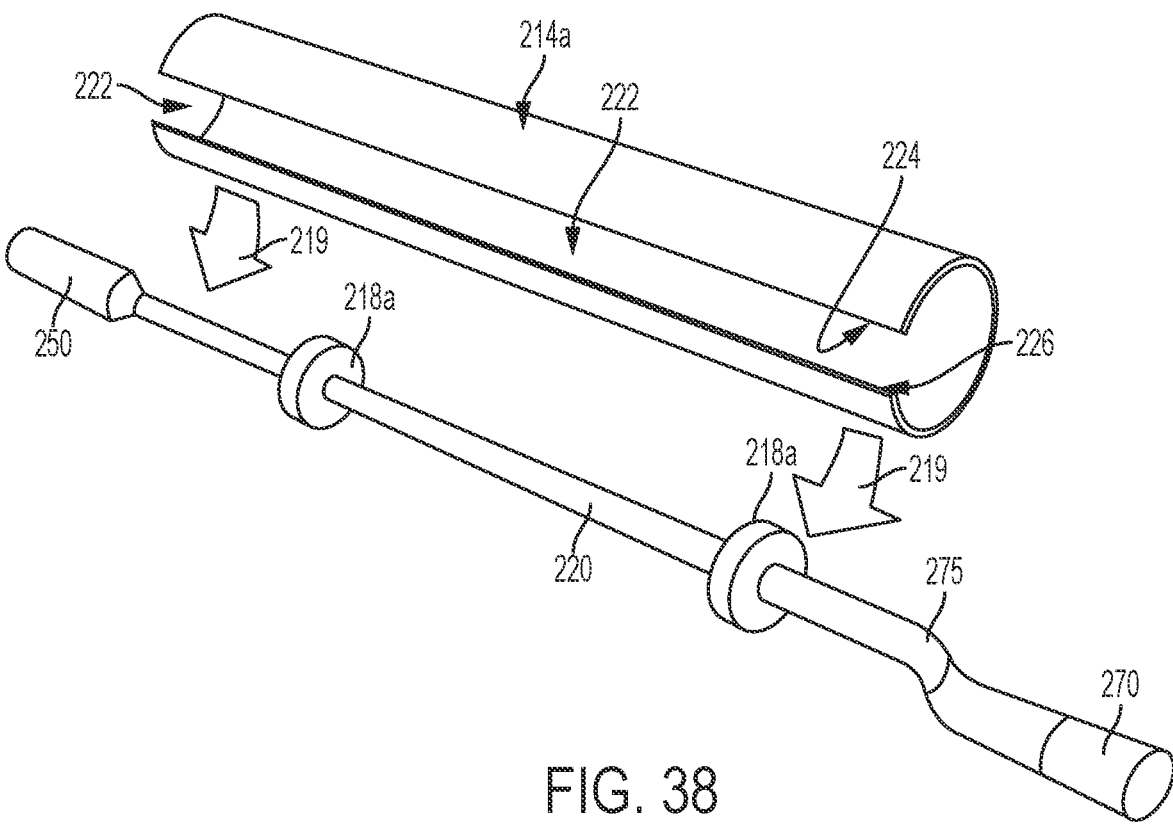
FIG. 38 is an exploded perspective view schematic diagram of the assembly shown in FIG. 37.

Referring to FIGS. 37 and 38, the ultrasonic transmission waveguide 220 and the isolation spacers 218a are inserted through the slot 222 and into the lumen 217a of the sheath 214a, as indicated by the arrows 219, without a need to insert either the ultrasonic transducer 250 or the compound curvature component 275 and the ultrasonic surgical blade 270 through the lumen 217a of the sheath 214a. The circumference of the sheath 214a is then compressed until the edges 224 and 226 of the slot 222 meet and form a seam 231, thereby closing the slot 222. The slot 222 may be permanently closed, for example, by laser welding the seam 231, ultrasonic welding the seam 231, applying adhesive to the seam 231, or otherwise bonding together the edges 224 and 226 of the slot 222 to form a bonded seam 231, which seals the ultrasonic transmission waveguide 220 and the isolation spacers 218a within the lumen 217a of the sheath 214a. Alternatively, or additionally, a shrinkable tube (not shown) is positioned over the outer circumference of the sheath 214a and shrunk to circumferentially seal the ultrasonic transmission waveguide 220 and the isolation spacers 218a within the lumen 217a of the sheath 214a.

Figure 39:
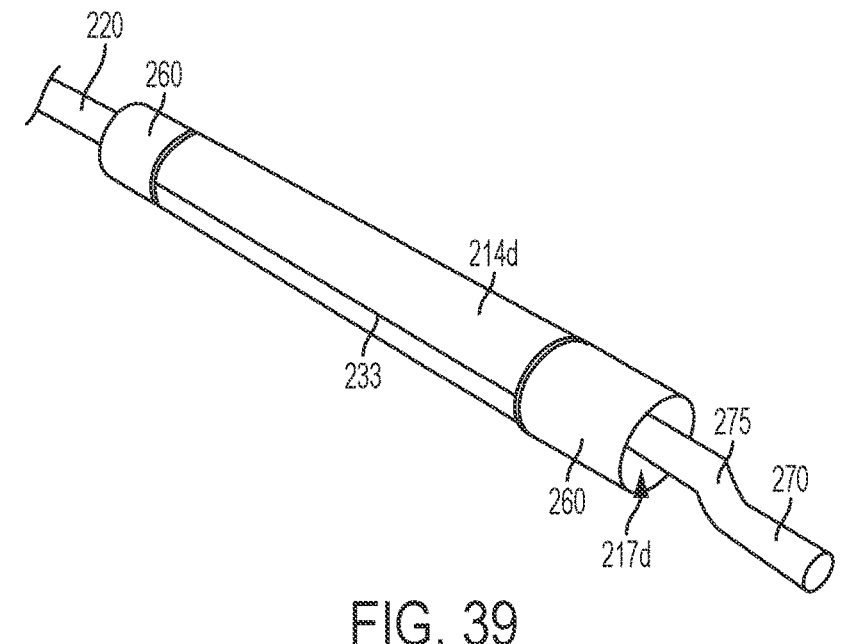
FIG. 39 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 40:
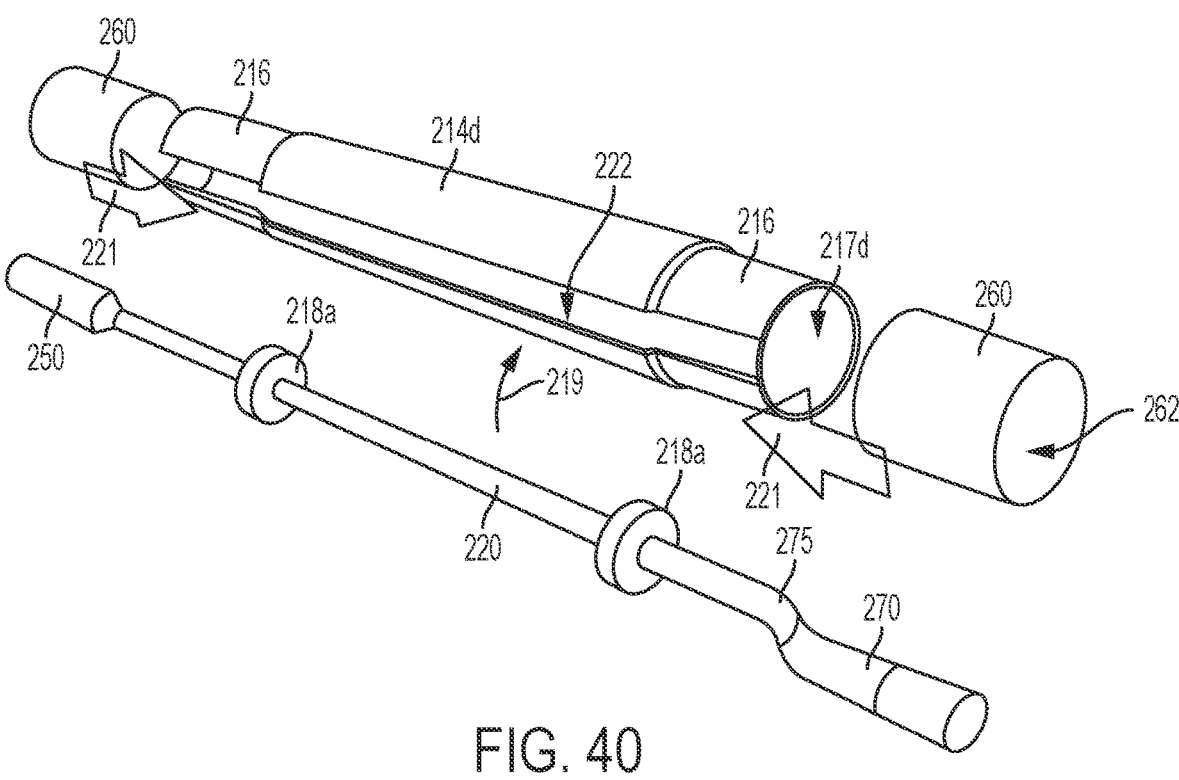
FIG. 40 is an exploded perspective view schematic diagram of the assembly shown in FIG. 39.

Referring to FIGS. 39 and 40, a sheath 214d comprises an open slot 222 extending longitudinally along the entire proximal-distal length of the sheath 214d. The sheath 214d also comprises reduced outside diameter portions 216 located on the proximal and distal ends of the sheath 214d. The ultrasonic transmission waveguide 220 and the isolation spacers 218a are inserted through the slot 222 and into the lumen 217d of the sheath 214d, as indicated by the arrow 219, without a need to insert either the ultrasonic transducer 250 or the compound curvature component 275 and the ultrasonic surgical blade 270 through the lumen 217d of the sheath 214d. The circumference of the sheath 214d is then compressed until the longitudinal edges of the slot 222 meet and form a seam 233, thereby closing the slot 222. End caps 260 are then press fit onto the proximal and distal ends of the sheath 214*d*, as indicated by arrows 221, wherein the reduced outside diameter portions 216 of the sheath 214*d* are inserted into the lumens 262 of the end caps 260.

The press fitting of the end caps 260 over the reduced outside diameter portions 216 of the sheath 214*d* close the slot 222, which seals the ultrasonic transmission waveguide 220 and the isolation spacers 218*a* within the lumen 217*d* of the sheath 214*d*. Optionally, the seam 233 may be laser welded, ultrasonic welded, bonded with an adhesive, or otherwise bonded. Alternatively, or additionally, a shrinkable tube (not shown) is positioned over the outer circumference of the sheath 214*d* and shrunk to further circumferentially seal the ultrasonic transmission waveguide 220 and the isolation spacers 218*a* within the lumen 217*d* of the sheath 214*d*.

Figures 41, 42:
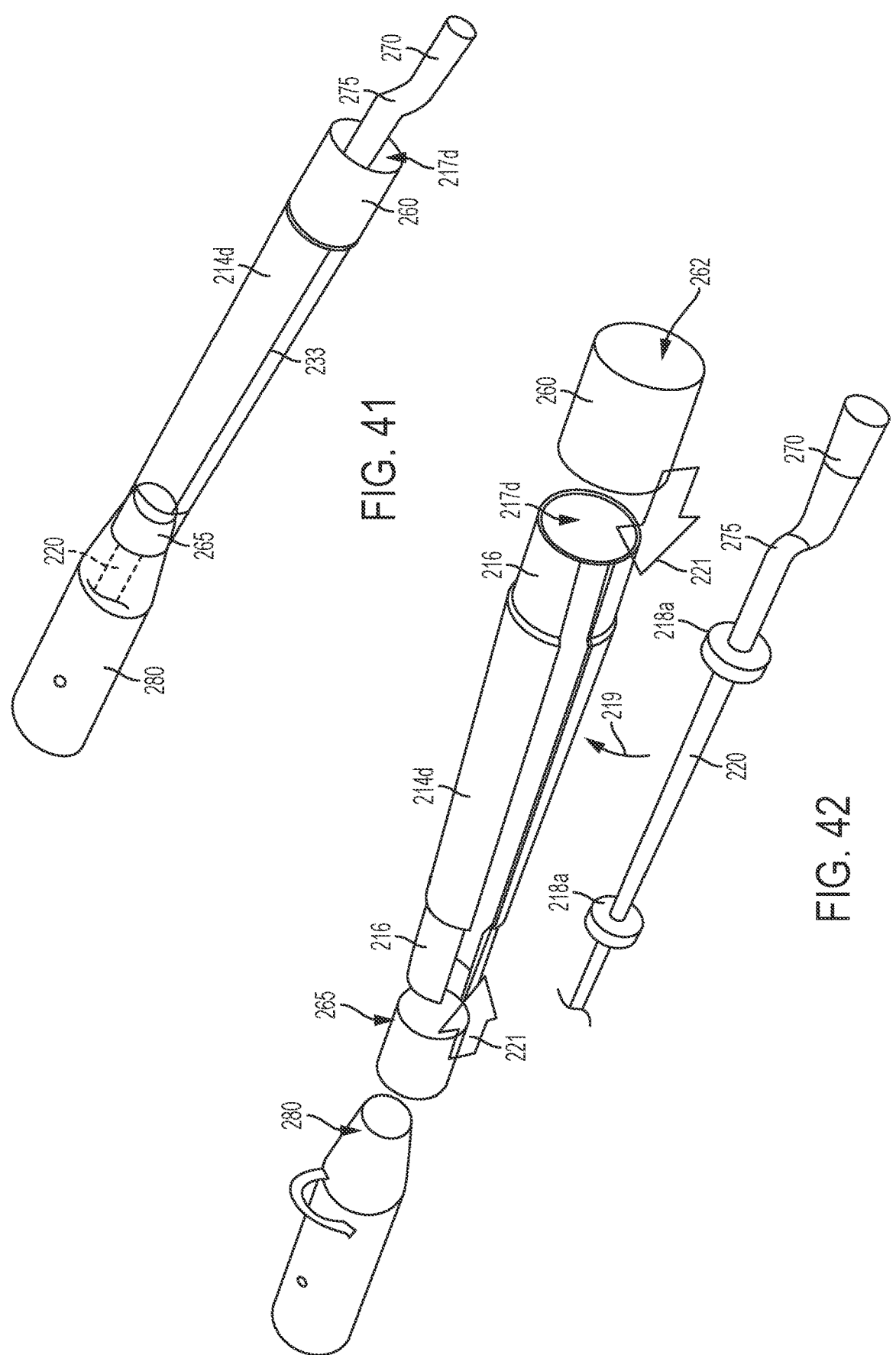
FIG. 41 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
FIG. 42 is an exploded perspective view schematic diagram of the assembly shown in FIG. 41.
Figure 43:
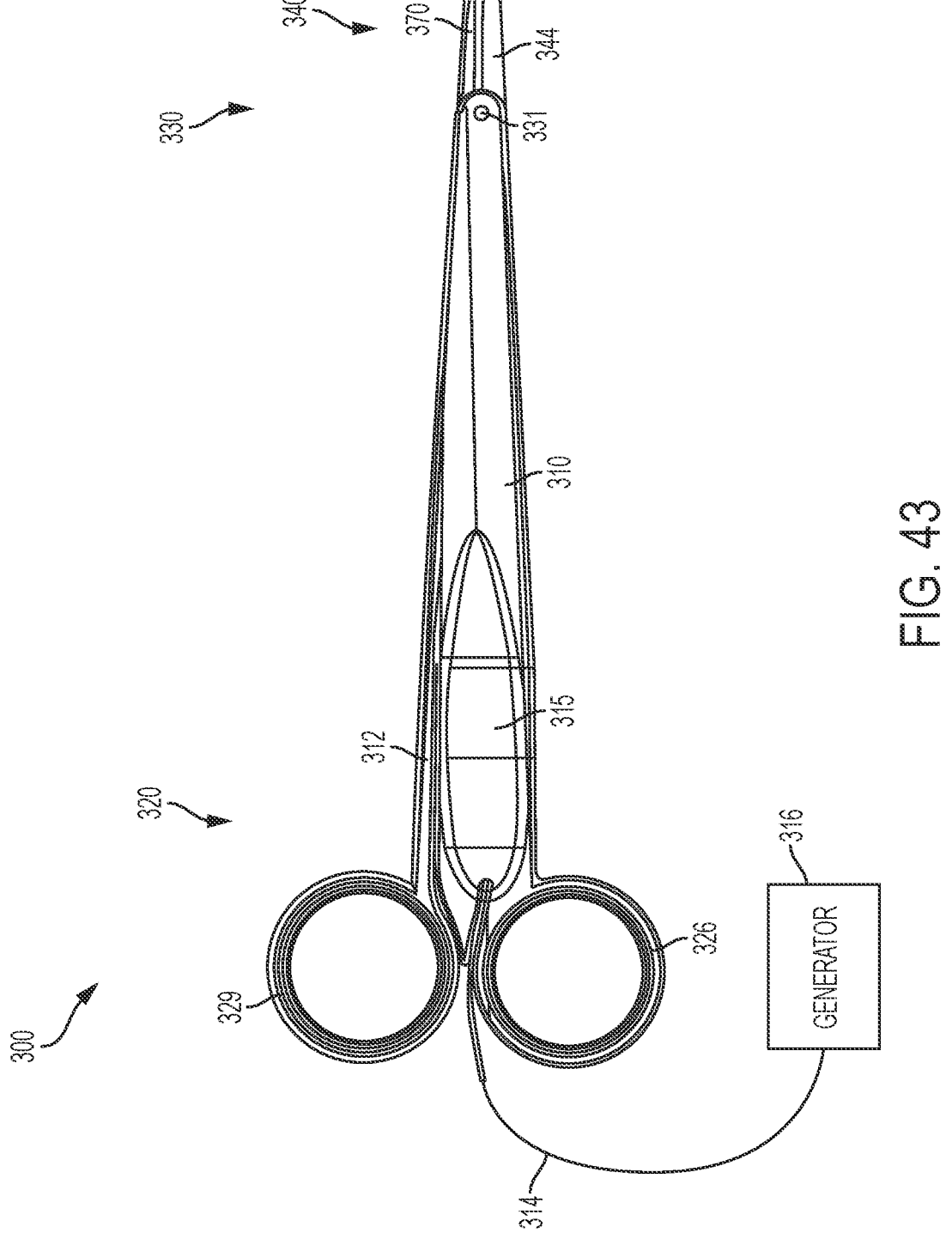
FIG. 43 is a side view of an ultrasonic surgical instrument having a scissor grip configuration.
Figure 44:
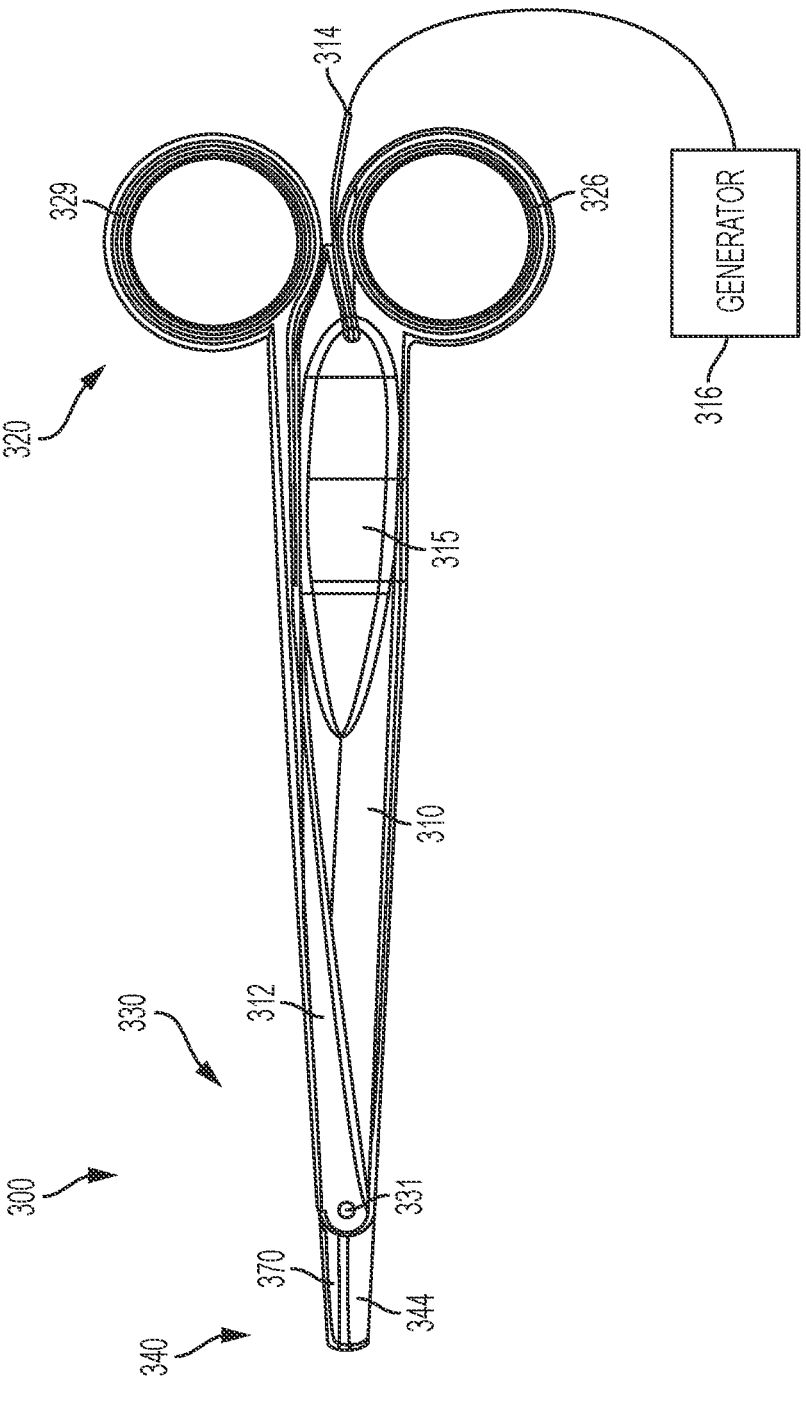
FIG. 44 is a side view of the ultrasonic surgical instrument shown in FIG. 43.
Figure 45:
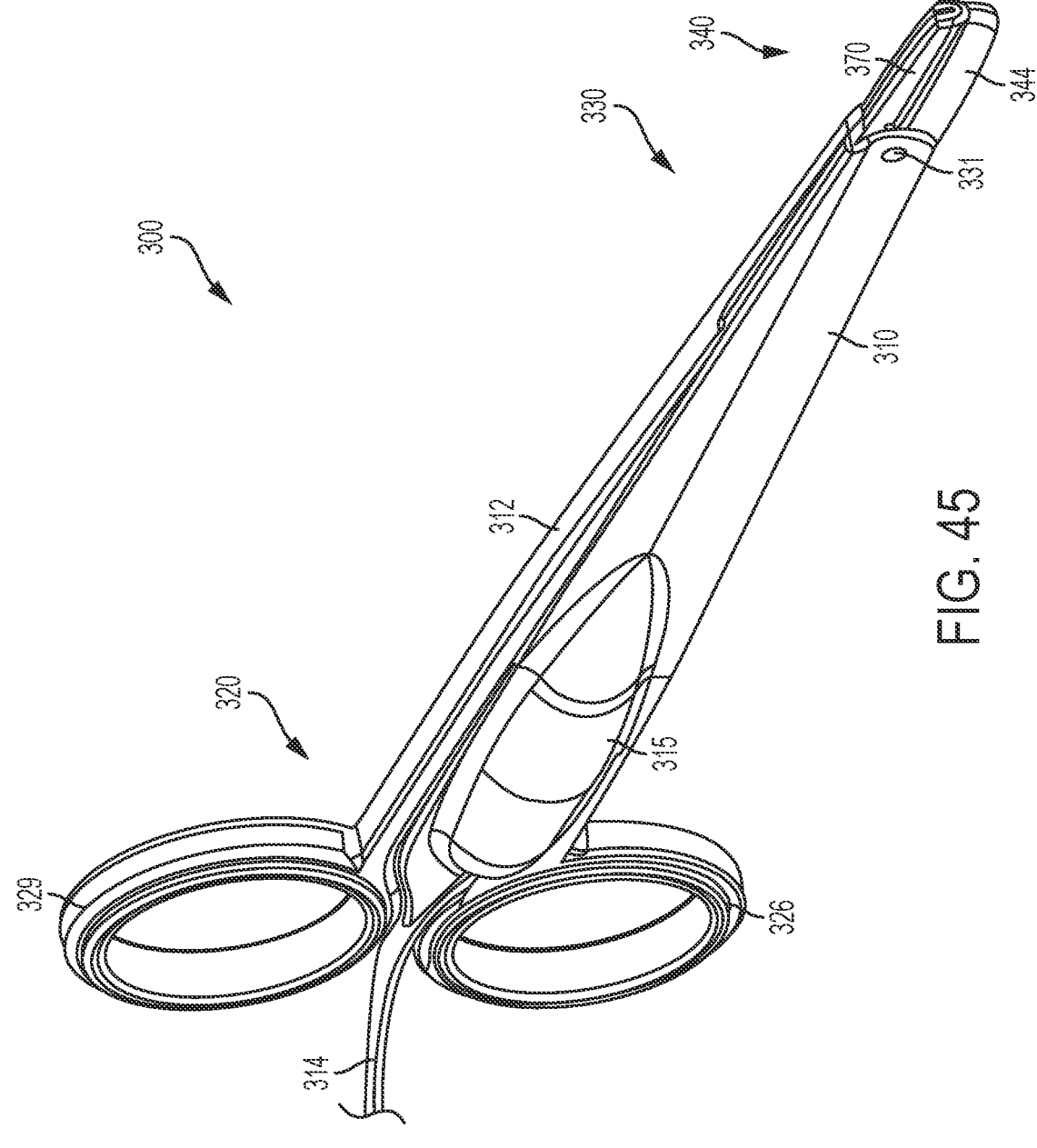
FIG. 45 is a front perspective view of the ultrasonic surgical instrument shown in FIGS. 43 and 44.
Figure 46:
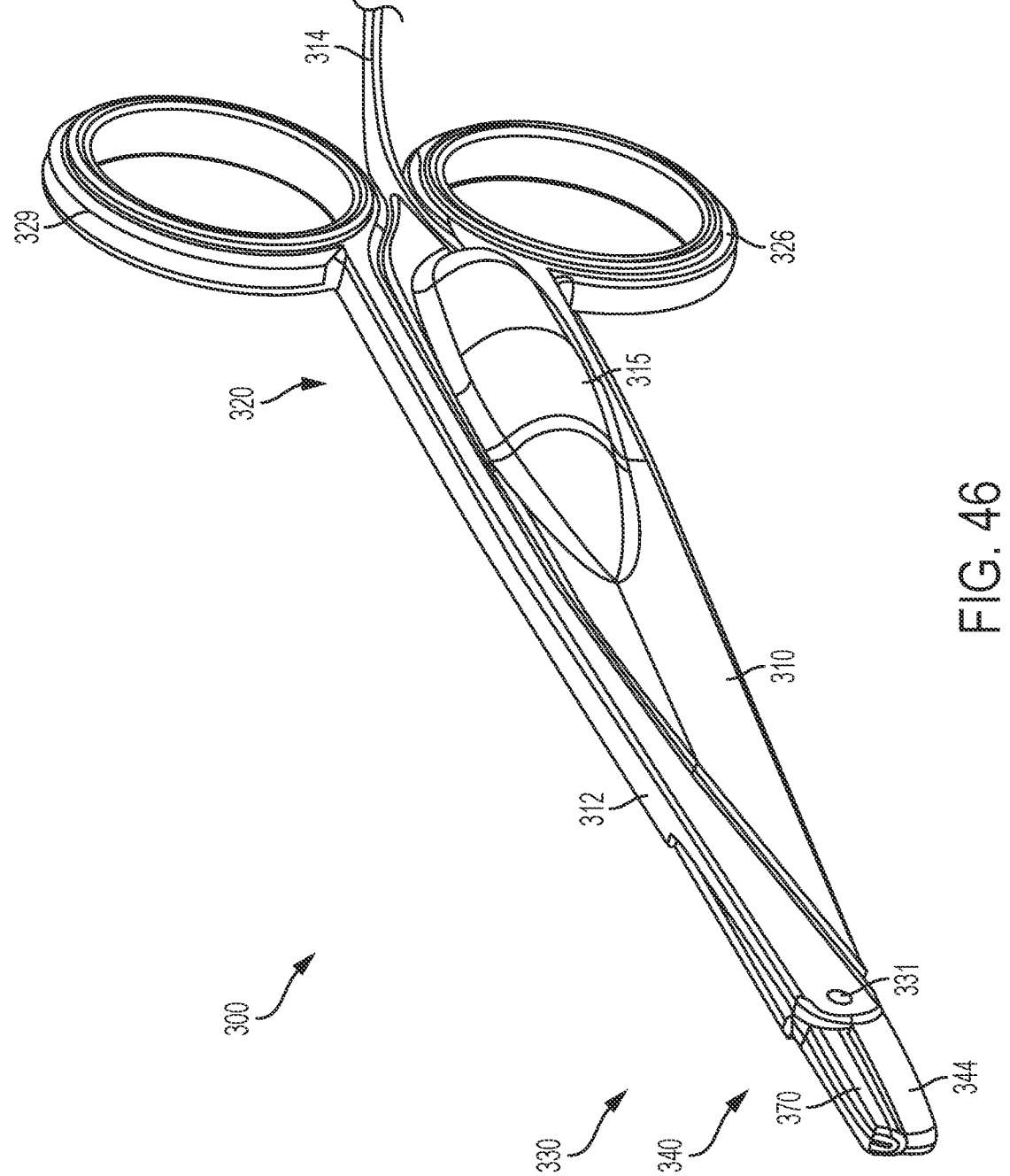
FIG. 46 is a front perspective view of the ultrasonic surgical instrument shown in FIGS. 43-45.

Referring to FIGS. 41 and 42, a sheath 214*d* comprises an open slot 222 extending longitudinally along the entire proximal-distal length of the sheath 214*d*. The sheath 214*d* also comprises reduced outside diameter portions 216 located on the proximal and distal ends of the sheath 214*d*. The ultrasonic transmission waveguide 220 and the isolation spacers 218*a* are inserted through the slot 222 and into the lumen 217*d* of the sheath 214*d*, as indicated by the arrow 219, without a need to insert either an ultrasonic transducer or the compound curvature component 275 and the ultrasonic surgical blade 270 through the lumen 217*d* of the sheath 214*d*. The circumference of the sheath 214*d* is then compressed until the longitudinal edges of the slot 222 meet and form a seam 233, thereby closing the slot 222. A distal end cap 260 and a proximal end cap 265 are then press fit onto the distal and proximal ends, respectively, of the sheath 214*d*, as indicated by arrows 221, wherein the reduced outside diameter portions 216 of the sheath 214*d* are inserted into the lumens 262 of the end caps 260 and 265.

The press fitting of the end caps 260 and 265 over the reduced outside diameter portions 216 of the sheath 214*d* close the slot 222, which seals the ultrasonic transmission waveguide 220 and the isolation spacers 218*a* within the lumen 217*d* of the sheath 214*d*. Optionally, the seam 233 may be laser welded, ultrasonic welded, bonded with an adhesive, or otherwise bonded. Alternatively, or additionally, a shrinkable tube (not shown) is positioned over the outer circumference of the sheath 214*d* and shrunk to further circumferentially seal the ultrasonic transmission waveguide 220 and the isolation spacers 218*a* within the lumen 217*d* of the sheath 214*d*.

The proximal end cap 265 may comprise external threads (not shown) located on the outer circumference surface of the end cap 265. A second sheath 280 has an inside diameter that is larger than the outside diameter of the sheath 214*d* and the proximal end cap 265. The second sheath 280 may comprise internal threads (not shown) located on the inner circumferential surface of the second sheath. The external threads on the proximal end cap 265 and the internal threads on the second sheath 280 mutually engage to attach the second sheath 280 to the sheath 214*d*. This allows multiple sheath segments to be joined together using an end cap as a coupler, where the diameter of the most distal sheath segment can be minimized relative to the more proximal sheath segment(s). In examples comprising a shrinkable tube (not shown), the shrunk tube may extend over both of the sheath segments 214*d* and 280, including the threaded joint between the second sheath 280 and the proximal end cap 265.

In connection with the examples described above, certain components of the acoustic systems (ultrasonic surgical blades, compound curvature components, ultrasonic transmission waveguides (including separate linear and curved regions), acoustic horns, and the like) are illustrated in the drawings as a single, contiguous piece of material (see, e.g., FIGS. 9-12, 19, 23, and 27-31, and 33-42). In such examples, the acoustic couplings between each component (or portions thereof) is provided by the contiguous material of the integrally formed components (and portions thereof). It is understood, however, that each component (or portion thereof) may be produced separately and acoustically coupled together in an operable manner, for example, using operable fastening mechanisms (e.g., threaded couplings) or metallurgical bonding techniques (e.g., welding).

Ultrasonic surgical blades and the associated acoustic components (e.g., ultrasonic transmission waveguides, acoustic horns, and the like) may be produced by forming and/or machining round bar or rod stock of a suitable metallic material such as titanium or titanium alloy, for example, to form an at least partially integral acoustic system. In some examples, it may be advantageous to produce ultrasonic surgical blades and integral acoustic components from a single piece of sheet metal stock that can be cut and formed instead of machined like bar or rod stock, and thus decrease manufacturing costs.

Referring to FIGS. 43-46, an ultrasonic surgical instrument 300 is shown having a scissor grip configuration. The ultrasonic surgical instrument 300 comprises a transducer/waveguide housing 310 and a clamp actuation member 312. The transducer/waveguide housing 310 and the clamp actuation member 312 are pivotably connected through a pivotable joint 331. The ultrasonic surgical instrument 300 comprises finger grip rings 326 and 329 integrally formed on the transducer/waveguide housing 310 and the clamp actuation member 312, respectively, at the proximal end 320 of the ultrasonic surgical instrument 300. The transducer/waveguide housing 310 comprises a transducer portion 315 within which an ultrasonic transducer 350 is housed (see FIGS. 51-54). The ultrasonic transducer 350 is coupled to a generator 316 via a cable 314 and may operate and comprise the features and characteristics described above.

Figure 47:
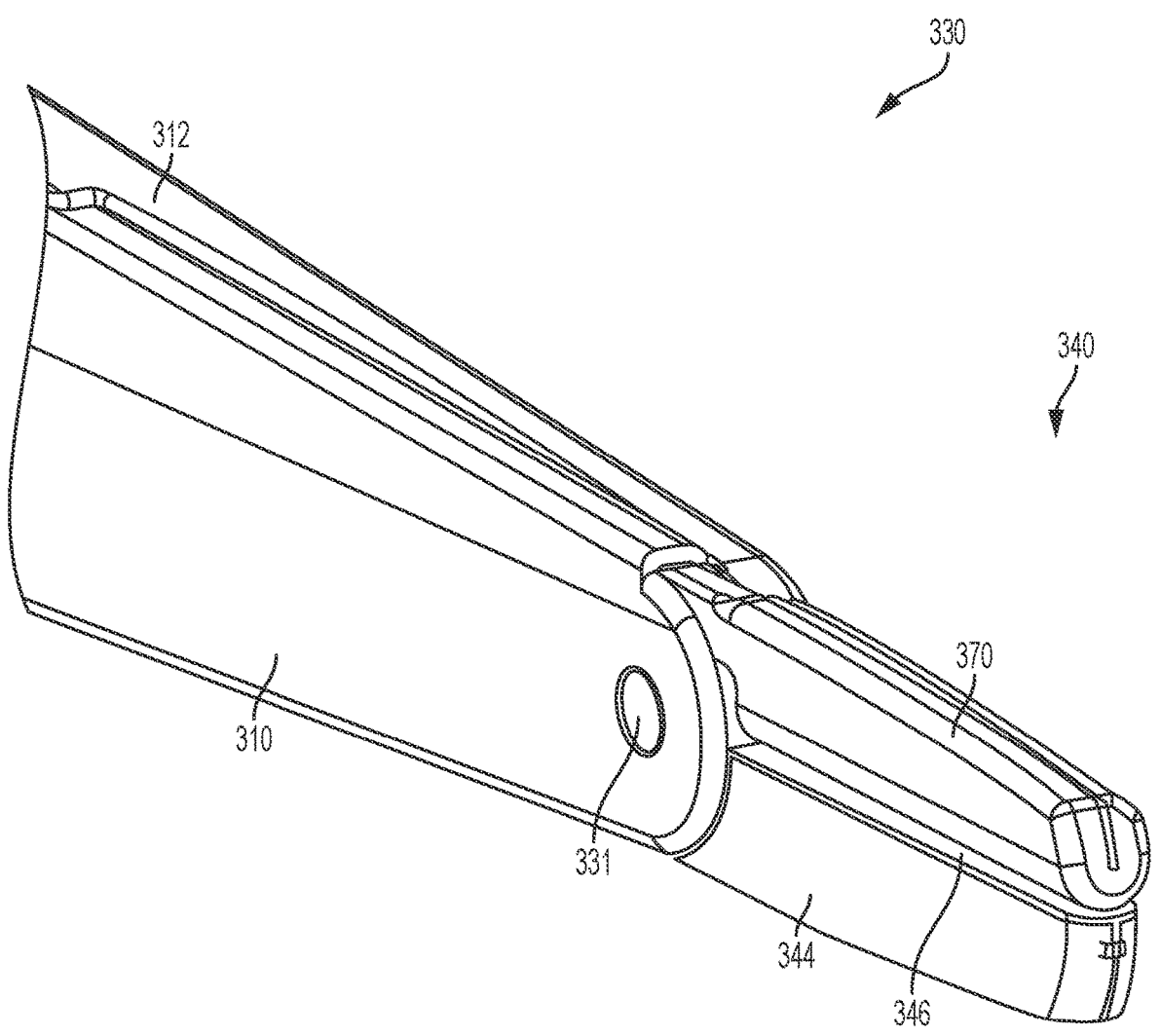
FIG. 47 is a front perspective view of the end-effector of the ultrasonic surgical instrument shown in FIGS. 43-46.
Figure 48:
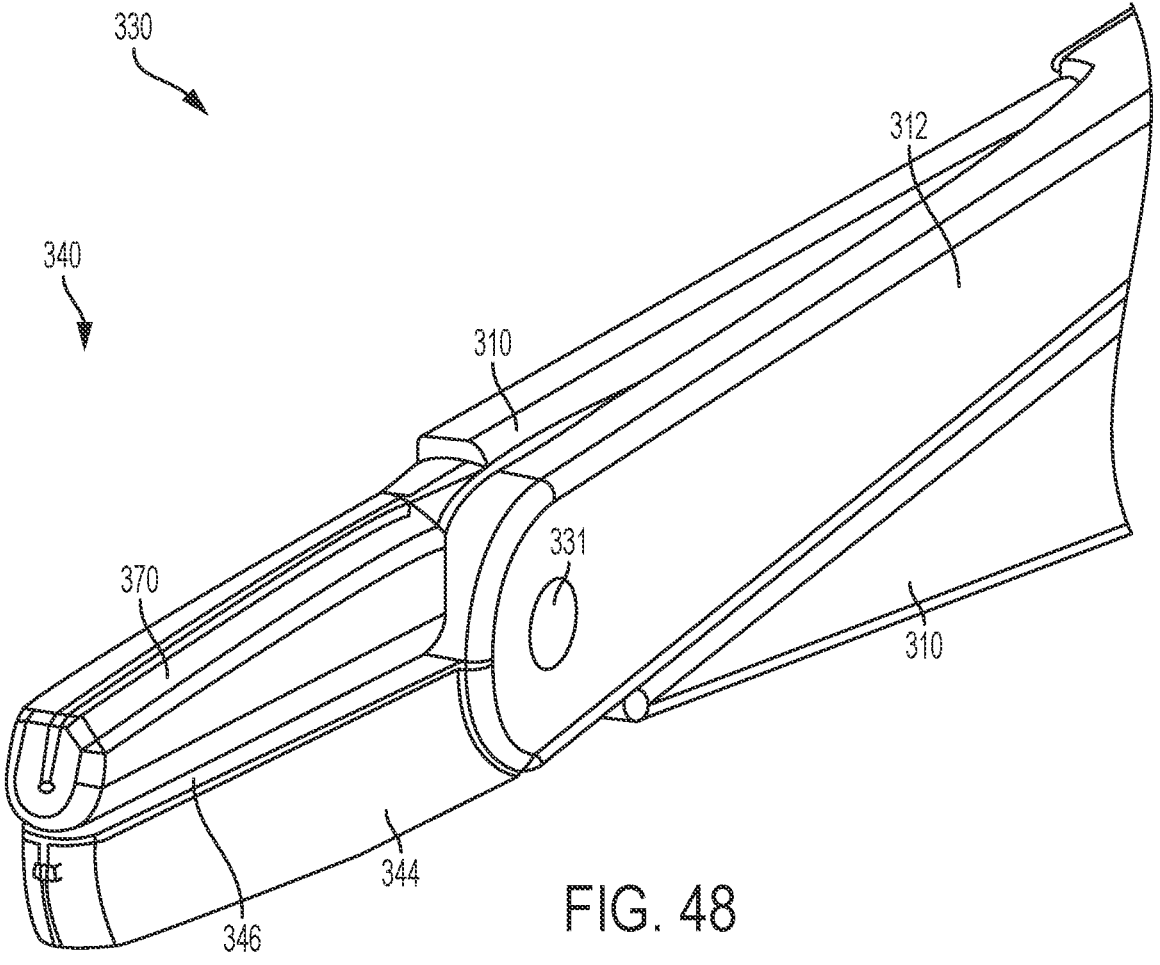
FIG. 48 is a front perspective view of the end-effector of the ultrasonic surgical instrument shown in FIGS. 43-46.

Referring to FIGS. 47 and 48, the transducer/waveguide housing 310 and the clamp actuation member 312 extend proximally from the pivotable joint 331. The ultrasonic surgical instrument 300 comprises an end-effector 340 extending distally from the pivotable joint 331 at the distal end 330 of the ultrasonic surgical instrument 300. The end-effector 340 comprises an ultrasonic surgical blade 370 and a clamp arm 344. The clamp arm 344 is integrally formed with the clamp actuation member 312 and extends distally from the pivotable joint 331. The clamp arm 344 comprises an optional clamp pad 346 which provides a tissue-engaging surface on the clamp arm 344.

Figure 49:
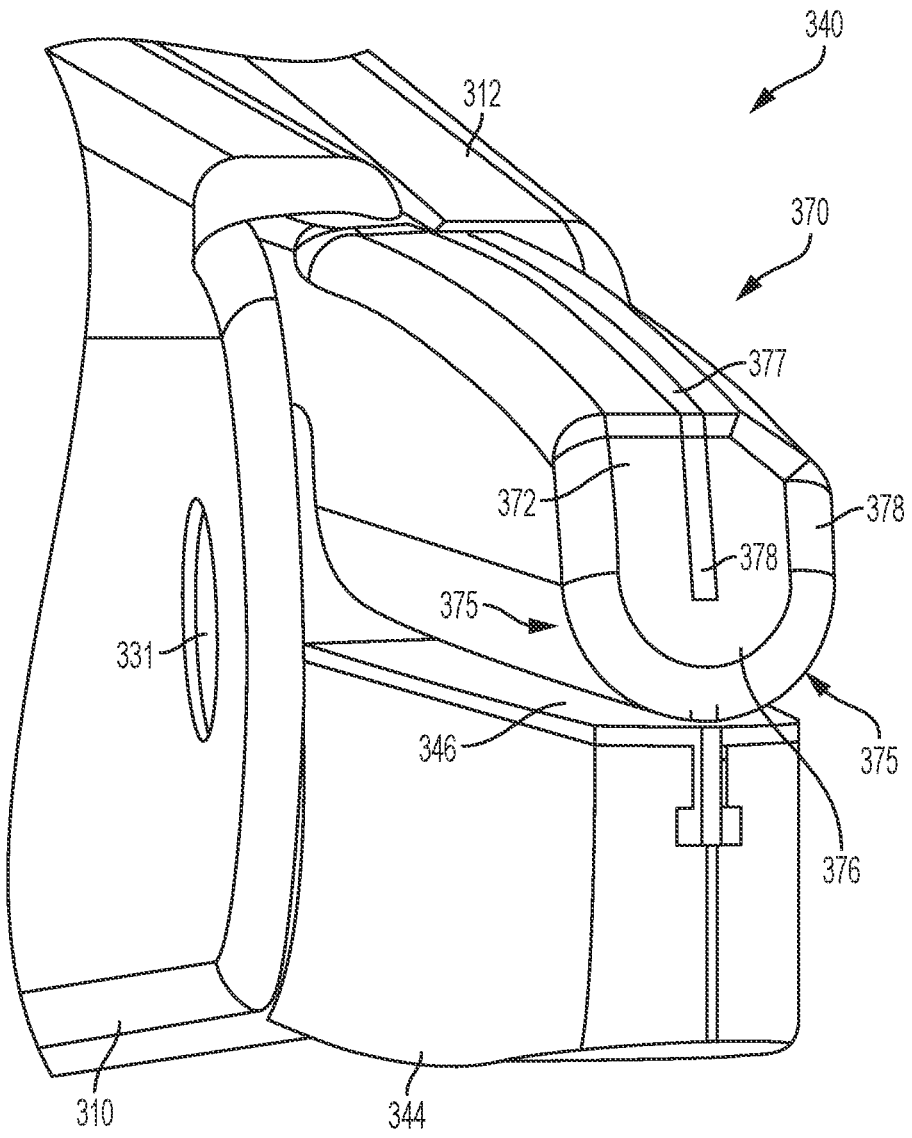
FIG. 49 is a front perspective view of the end-effector of the ultrasonic surgical instrument shown in FIGS. 43-46.
Figure 50:
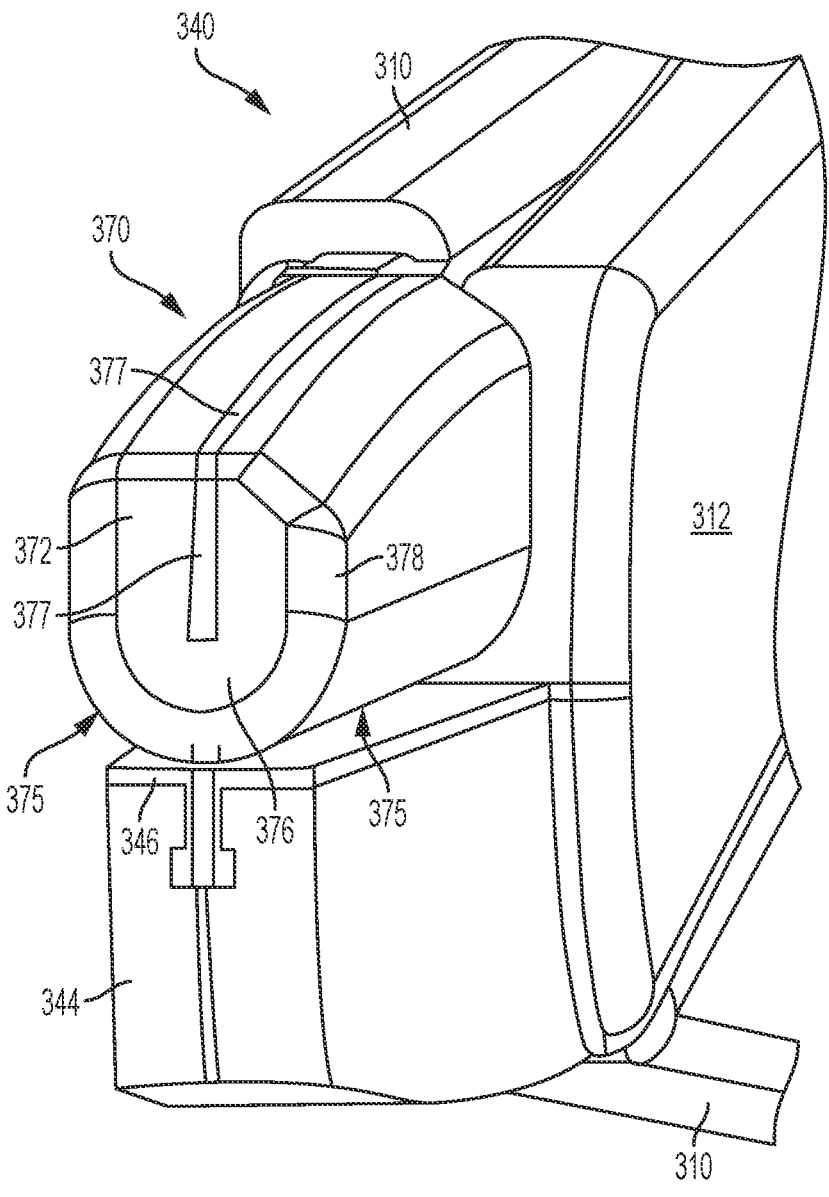
FIG. 50 is a front perspective view of the end-effector of the ultrasonic surgical instrument shown in FIGS. 43-46.
Figure 51:
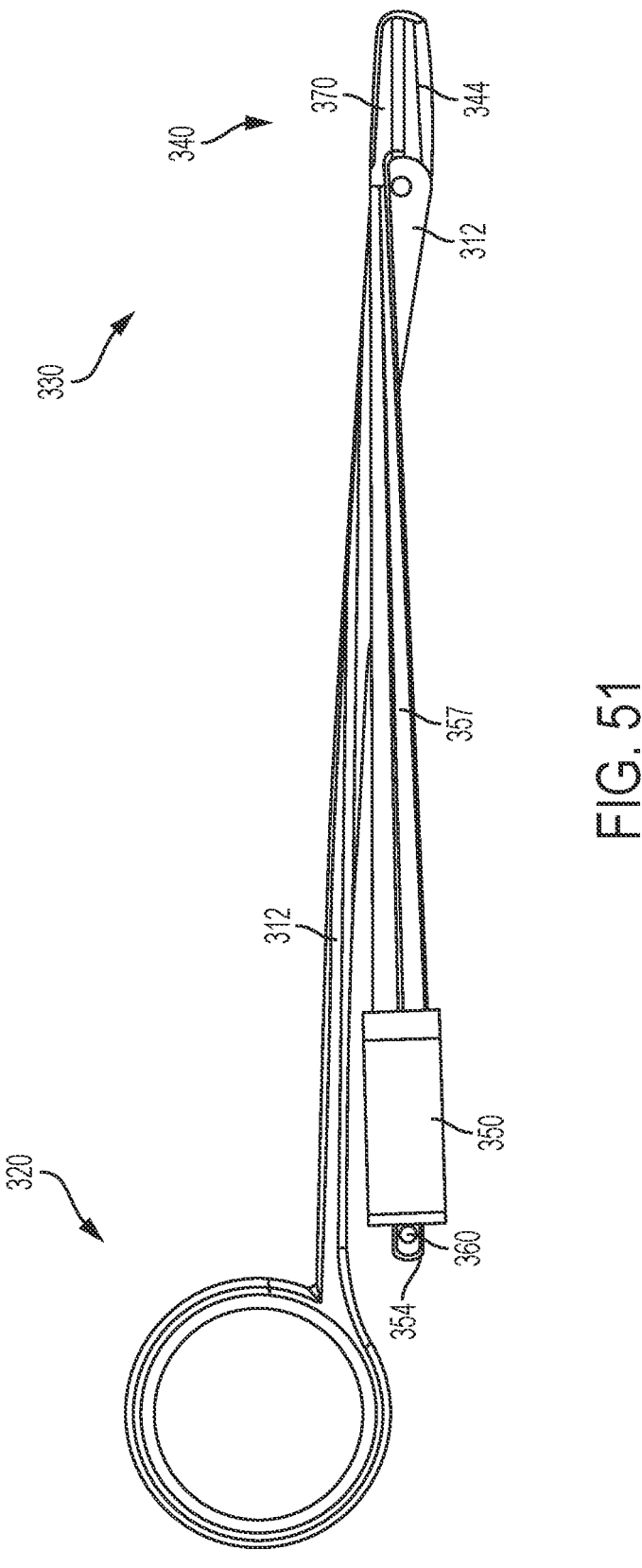
FIG. 51 is a side view schematic diagram of the ultrasonic surgical instrument shown in FIGS. 43-46 with a transducer/waveguide housing removed to show the ultrasonic transducer and the ultrasonic transmission waveguide.
Figure 52:
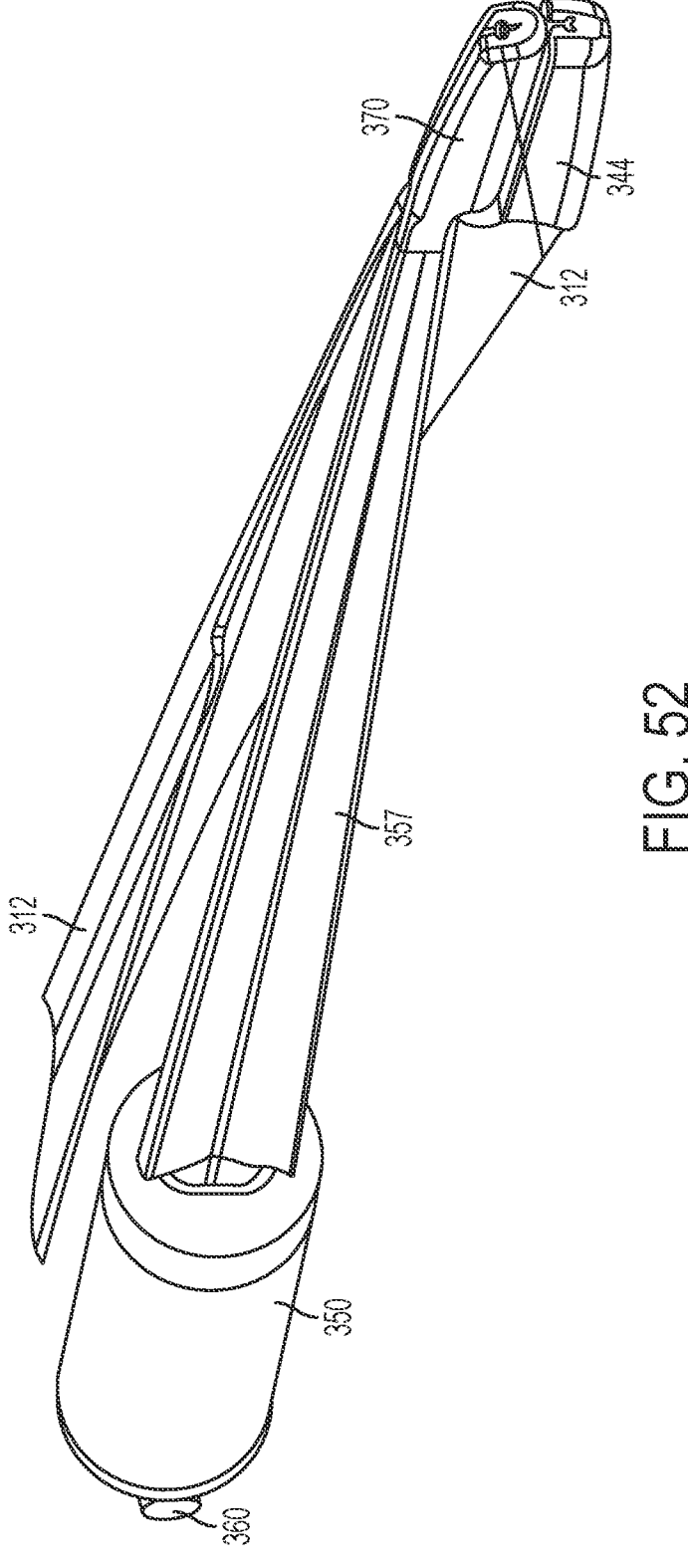
FIG. 52 is a perspective view schematic diagram of the ultrasonic surgical instrument as shown in FIG. 51.

Referring again to FIGS. 49 and 50, the ultrasonic surgical blade 370 comprises a body portion 372, a bent portion 376, and a folded portion 378. A gap 377 is located between the body portion 372 and the folded portion 378. In some examples, the gap 377 may contain an isolation spacer or other filler material (e.g., an elastomeric material such as silicone rubber) that maintains separation of the body portion 372 and the folded portion 378 and prevents contact during ultrasonic vibratory activation of the ultrasonic surgical blade 370. The ultrasonic surgical blade 370 comprises a tissue-engaging surface 375 which is located on the bent portion 376.

Figures 55, 56:
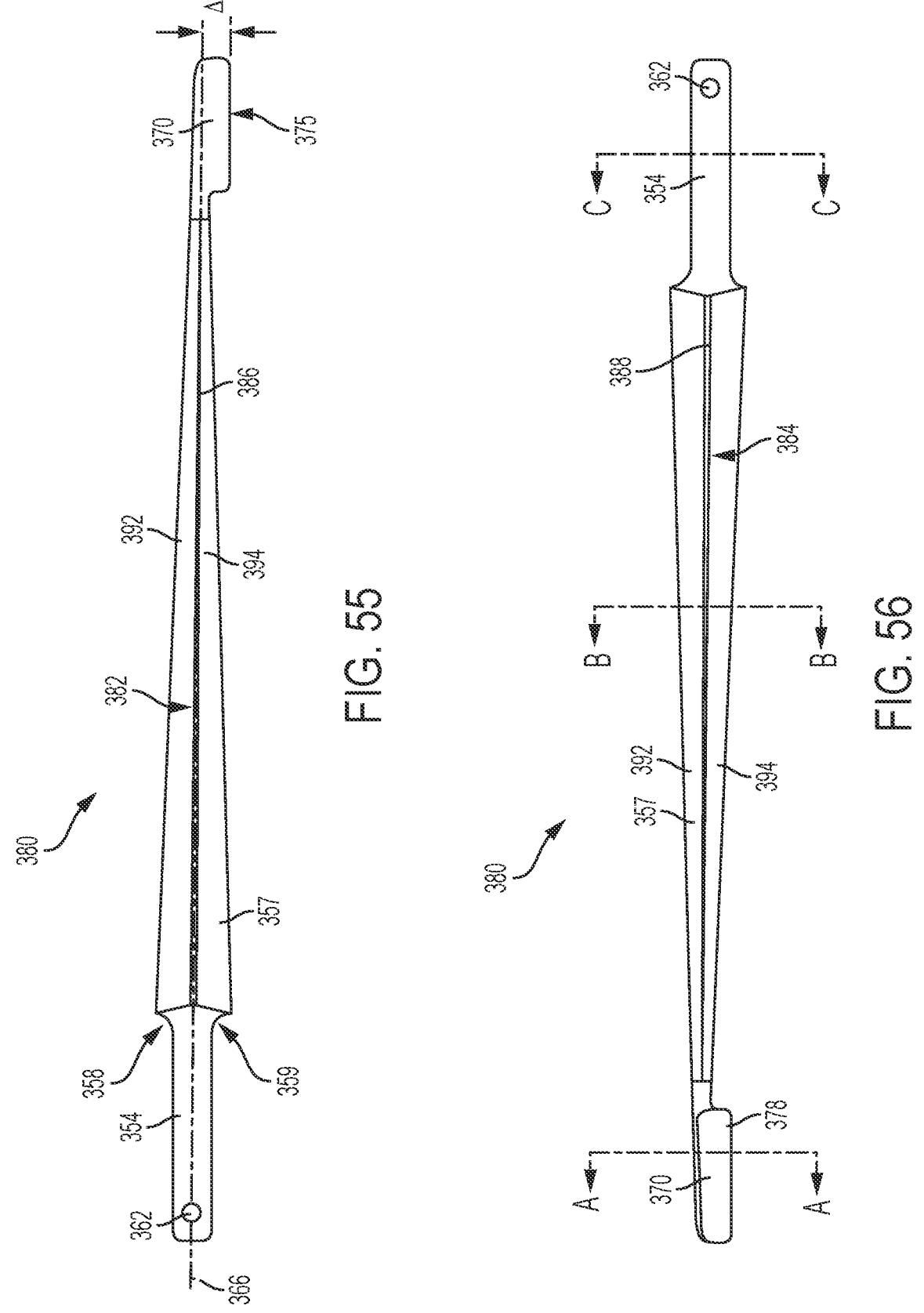
FIG. 55 is a side view schematic diagram of the blade of the ultrasonic surgical instrument shown in FIGS. 43-46.
FIG. 56 is a side view schematic diagram of the blade of the ultrasonic surgical instrument shown in FIGS. 43-46.

Referring to FIGS. 51, 52, 55, and 56, the ultrasonic surgical instrument 300 comprises an acoustic system 380 comprising the ultrasonic surgical blade 370, an ultrasonic transmission waveguide 357, and a transduction shaft 354. As shown in FIGS. 55 and 56, the acoustic system 380 is formed from a single, contiguous piece of material (e.g., a single piece of sheet metal stock that is cut and formed to produce the ultrasonic surgical blade 370, the ultrasonic transmission waveguide 357, and the transduction shaft 354). Thus, the ultrasonic surgical blade 370, the ultrasonic transmission waveguide 357, and the transduction shaft 354 are integrally formed from the single, contiguous piece of material (e.g., a single piece of sheet metal stock).

Figure 57A:
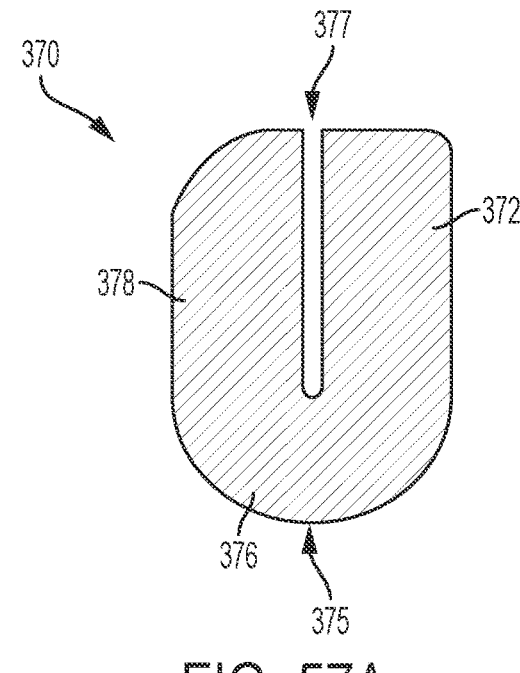
FIG. 57A is a cross-sectional schematic diagram of the ultrasonic surgical blade shown in FIGS. 55 and 56 as viewed along line A-A in FIG. 56.

Referring to FIGS. 56 and 57A, and as described above, the ultrasonic surgical blade 370 comprises a body portion 372, a bent portion 376, a folded portion 378, a gap 377 located between the body portion 372 and the folded portion 378 (optionally containing an isolation spacer or other filler material that maintains separation of the body portion 372 and the folded portion 378 and prevents contact during ultrasonic vibratory activation of the ultrasonic surgical blade 370), and a tissue-engaging surface 375 located on the bent portion 376. As shown in FIG. 57A, the ultrasonic surgical blade 370 comprises a U-shaped cross-section transverse to a central transducer/waveguide axis 366 (see FIG. 55).

Figure 57B:
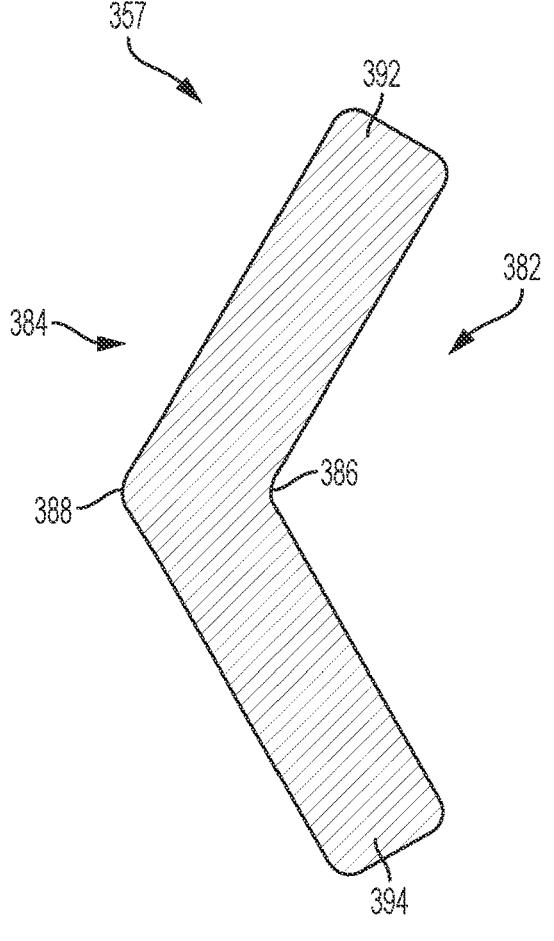
FIG. 57B is a cross-sectional schematic diagram of the ultrasonic surgical blade shown in FIGS. 55 and 56 as viewed along line B-B in FIG. 56.
Figure 57C:
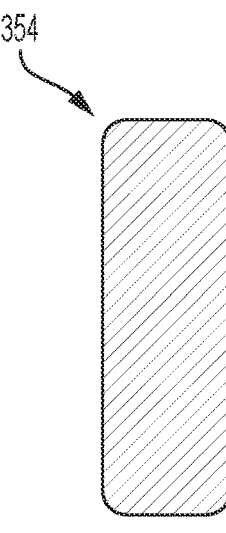
FIG. 57C is a cross-sectional schematic diagram of the ultrasonic surgical blade shown in FIGS. 55 and 56 as viewed along line C-C in FIG. 56.

Referring to FIGS. 55, 56, and 57B, the ultrasonic transmission waveguide 357 comprises a top portion 392 and a bottom portion 394. The top portion 392 and the bottom portion 394 are separated by an inward bend 386 and an outward bend 388, which coincide with the central transducer/waveguide axis 366. The inward bend 386 forms an inwardly bent side 382 of the ultrasonic transmission waveguide 357. The outward bend 388 forms an outwardly bent side 384 of the ultrasonic transmission waveguide 357. As shown in FIG. 57B, the ultrasonic transmission waveguide 357 comprises a V-shaped cross-section transverse to the central transducer/waveguide axis 366.

Referring to FIGS. 55 and 56, the transduction shaft 354 is acoustically coupled to the ultrasonic transmission waveguide 357 through a T-shaped region formed where the top portion 392 and the bottom portion 394 begin to transversely extend from the central (longitudinal) transducer/waveguide axis 366 (and also from the inward and outward bends 386 and 388). As show in FIG. 55, the T-shaped transition region is formed by the intersection of the transduction shaft 354 with the top and bottom proximal edges 358 and 359 of the top and bottom portions 392 and 394 of the ultrasonic transmission waveguide 357. The transduction shaft 354 also comprises a proximal bore 362 through the thickness of the transduction shaft 354.

Referring again to FIGS. 43-46, the transduction shaft 354 and the ultrasonic transmission waveguide 357 of the acoustic system 380 are located within the transducer/waveguide housing 310, and the ultrasonic surgical blade extends outside the transducer/waveguide housing 310, distally from the pivotable joint 331. Referring again to FIGS. 51 and 52, the transduction shaft 354 of the acoustic system 380 is located through an aperture that extends the length of the ultrasonic transducer 350. The ultrasonic transducer 350 is clamped between the top and bottom proximal edges 358 and 359 of the ultrasonic transmission waveguide 357 and a cam lock 360 extending through the proximal bore 362 in the transduction shaft 354.

Figure 53:
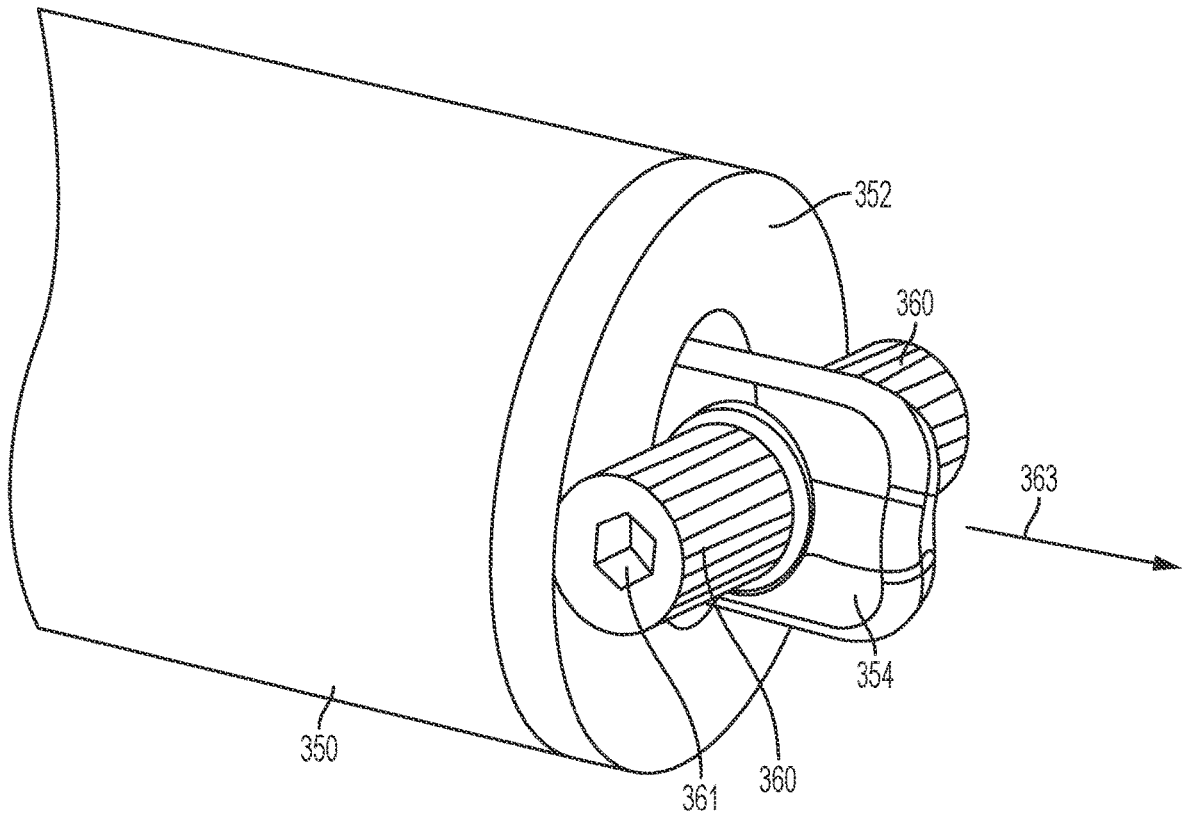
FIG. 53 is a rear perspective view schematic diagram showing a cam lock assembly for acoustically coupling an ultrasonic transmission waveguide to the ultrasonic transducer.
Figure 54:
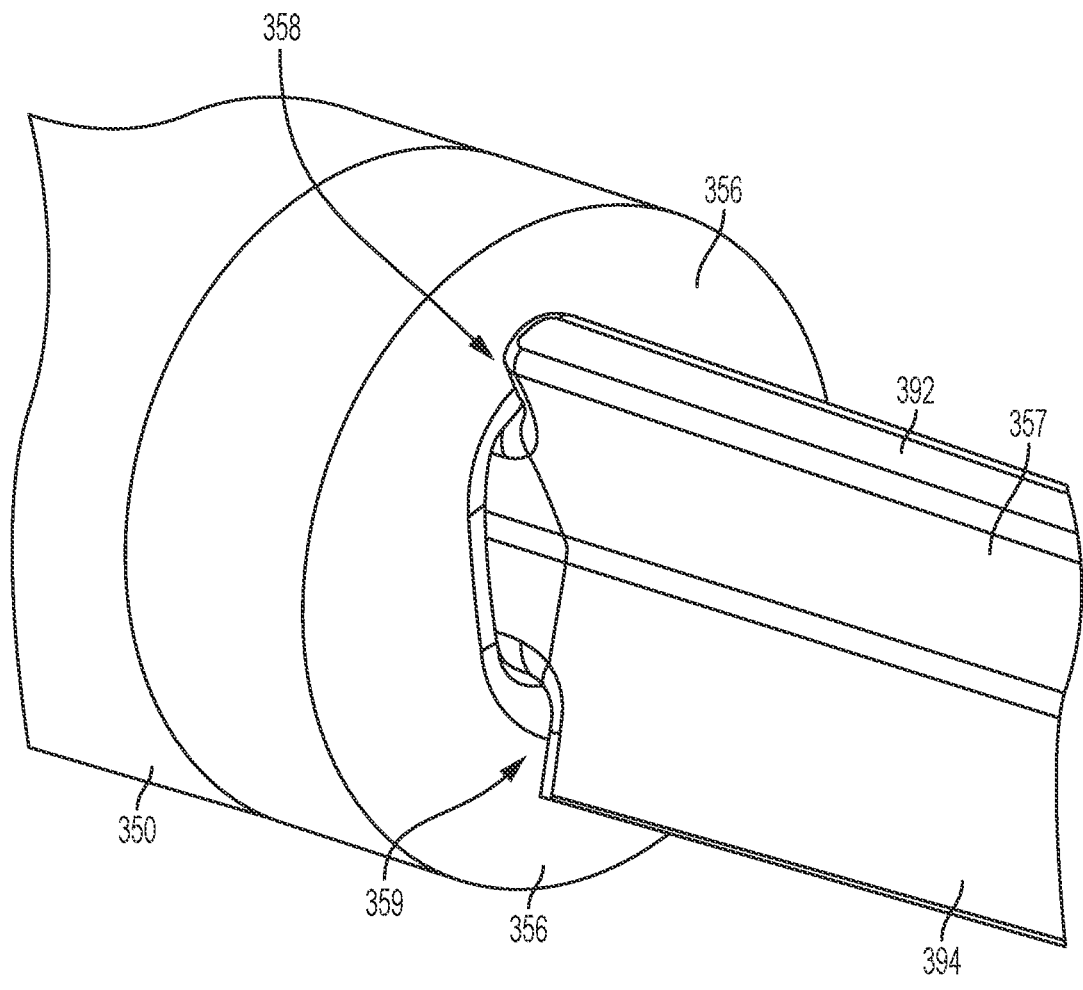
FIG. 54 is a front perspective view schematic diagram showing an ultrasonic transmission waveguide acoustically coupled to the ultrasonic transducer.

Referring to FIGS. 53 and 54, the top and bottom proximal edges 358 and 359 of the ultrasonic transmission waveguide 357 engage the distal end surface 356 of the ultrasonic transducer 350. The cam lock 360 engages the proximal end surface 352 of the ultrasonic transducer 350. The rotation of the cam lock 360 (for example, using a hex wrench in the hex-shaped blind bore 361) forces the transduction shaft 354 proximally, as indicated by arrow 363, which tensions the transduction shaft 354 and secures the top and bottom proximal edges 358 and 359 of the ultrasonic transmission waveguide 357 against the distal end surface 356 of the ultrasonic transducer 350, thereby acoustically coupling the ultrasonic transmission waveguide 357 to the ultrasonic transducer 350.

As shown in FIGS. 55 and 56, the width of the ultrasonic transmission waveguide 357 perpendicular to the central transducer/waveguide axis 366 decreases from a maximum at the top and bottom proximal edges 358 and 359 to a minimum at the distal transition region with the ultrasonic surgical blade 370. The ultrasonic transmission waveguide 357 thus has a tapered width that decreases from a maximum at the acoustic coupling with the ultrasonic transducer 350 to a minimum at the transition to the ultrasonic surgical blade 370 (see FIGS. 51 and 52). This longitudinal taper allows the ultrasonic transmission waveguide 357 to also function as an acoustic horn that focuses and amplifies the ultrasonic vibrations produced by the ultrasonic transducer 350 to the ultrasonic surgical blade 370. Referring to FIG. 55, the tissue-engaging surface 375 of the ultrasonic surgical blade 370 is transversely off-set from the central transducer/waveguide axis 366 by a linear distance A.

In various examples, a foot pedal or other switching device (not shown) operably connected to the generator 316 may be employed to control the application of electrical power from the generator 316 to the ultrasonic transducer 350. When power is applied to the ultrasonic transducer 350 by operation of a foot pedal or other switch arrangement, the acoustic system 380 may, for example, cause the ultrasonic surgical blade 370 to vibrate longitudinally along the central waveguide/shaft axis 366 (see FIGS. 55 and 56) at approximately 55.5 kHz, and the amount of longitudinal movement will vary proportionately with the amount of driving power (electrical current) applied, which may be adjustably selected by a surgeon or other operator of the ultrasonic surgical instrument 300.

The ultrasonic transducer 350 transmits ultrasonic vibrations to the acoustically coupled ultrasonic transmission waveguide 357 through the T-shaped region where the top and bottom proximal edges 358 and 359 of the top and bottom portions 392 and 394 of the ultrasonic transmission waveguide 357 are secured against the distal end surface 356 of the ultrasonic transducer 350. The ultrasonic vibrations are then transmitted and focused through the ultrasonic transmission waveguide 357 to the ultrasonic surgical blade 370. A surgeon or other operator can pivot the ultrasonic surgical blade 370 and the clamp arm 344 toward and away from each other by pivoting the transducer/waveguide housing 310 and the clamp actuation member 312 toward and away from each other using the finger grip rings 326 and 329.

The instruments, devices, assemblies, and systems described in this specification can be configured for disposal after a single use, or they can be configured for reuse one or more times. In either case, however, the instruments, devices, assemblies, and systems can be reconditioned for reuse after at least one use. Reconditioning can include any combination of the steps of disassembly of the instruments, devices, assemblies, and systems, followed by cleaning or replacement of particular pieces, and subsequent reassembly. For example, an instrument or device can be disassembled, and any number of the particular pieces or parts of the device can be selectively replaced or removed in any combination. Upon cleaning and/or replacement of particular parts, the instrument or device can be reassembled for subsequent use either at a reconditioning facility, or by a surgical team immediately prior to a surgical procedure. Those skilled in the art will appreciate that reconditioning of an instrument or device can utilize a variety of techniques for disassembly, cleaning/replacement, and reassembly. Use of such techniques, and the resulting reconditioned device, are all within the scope of the invention(s) described in this specification.

By way of example only, the instruments described in this specification may be processed before use in a surgical procedure. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill or otherwise inactivate bacteria, viruses, or other microorganisms or pathogenic material on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide treatment, plasma peroxide treatment, or steam treatment.

The ultrasonic surgical instruments described in this specification may be used for performing laparoscopic and minimally invasive surgical procedures. However, the reader will appreciate that the instruments can be used in numerous surgical procedures and applications including, for example, in connection with open or otherwise invasive surgical procedures. The reader will further appreciate that the instruments may be inserted into a patient's body in any way, such as through a natural orifice (e.g., ear, nose, mouth, or rectum), through an incision or puncture hole formed in tissue, and the like. The end-effector portions of the instruments can be inserted directly into a patient's body or can be inserted through an access device (e.g., a trocar) that has a working channel through which the end-effector and an elongated shaft of a surgical instrument can be advanced. Additionally, it is understood that the ultrasonic surgical instruments described in this specification may be implemented in medical surgical procedures on humans or in veterinary surgical procedures on animals.

ASPECTS OF THE INVENTION

Aspects of the invention include, but are not limited to, the following numbered clauses.

1. An ultrasonic surgical instrument comprising: an ultrasonic transducer having a central transducer axis; an acoustic horn acoustically coupled to the ultrasonic transducer; an ultrasonic transmission waveguide acoustically coupled to the acoustic horn, the ultrasonic transmission waveguide comprising a curved portion and a linear portion and; an ultrasonic surgical blade acoustically coupled to the ultrasonic transmission waveguide; wherein the linear portion of the ultrasonic transmission waveguide and the ultrasonic surgical blade are angularly off-set from the central transducer axis.

2. The ultrasonic surgical instrument of clause 1, wherein the linear portion of the ultrasonic transmission waveguide has a central waveguide axis, and wherein the central waveguide axis and the central transducer axis intersect and form an off-set angle ranging from 120-degrees to 150-degrees.

3. The ultrasonic surgical instrument of clause 1, further comprising: a handle assembly comprising a handle body and a clamp actuation member pivotably coupled to the handle body; a shaft assembly connected to the handle assembly; and an end-effector connected to the shaft assembly, the end-effector comprising the ultrasonic surgical blade and a clamp arm pivotably coupled to the shaft assembly, wherein: the ultrasonic transducer, the acoustic horn, and the curved portion of the ultrasonic transmission waveguide are located within the handle body; and the linear portion of the ultrasonic transmission waveguide is located within the shaft assembly.

4. The ultrasonic surgical instrument of clause 3, wherein the shaft assembly comprises a reciprocating upper shaft member and a lower shaft member integrally formed with the handle body, and wherein the linear portion of the ultrasonic transmission waveguide is located between the reciprocating upper shaft member and the lower shaft member.

5. The ultrasonic surgical instrument of clause 4, wherein: the clamp actuation member is pivotably coupled to the handle body and pivotably coupled to the reciprocating upper shaft member; the reciprocating upper shaft member is pivotably coupled to the clamp arm; and the clamp arm is pivotably coupled to the lower shaft member.

6. The ultrasonic surgical instrument of clause 5, wherein: pivotal motion of the clamp actuation member toward the handle body causes distal translational motion of the reciprocating upper shaft member, and the distal translational motion of the reciprocating upper shaft member causes pivotal motion of the clamp arm toward the ultrasonic surgical blade, thereby closing the end-effector; and pivotal motion of the clamp actuation member away from the handle body causes proximal translational motion of the reciprocating upper shaft member, and the proximal translational motion of the reciprocating upper shaft member causes pivotal motion of the clamp arm away from the ultrasonic surgical blade, thereby opening the end-effector.

7. The ultrasonic surgical instrument of any one of clauses 1-6, further comprising a compound curvature component acoustically coupling the ultrasonic surgical blade to the linear portion of the ultrasonic transmission waveguide, wherein the linear portion of the ultrasonic transmission waveguide has a central waveguide axis, and wherein the compound curvature region transversely off-sets the ultrasonic surgical blade from the central waveguide axis.

8. The ultrasonic surgical instrument of clause 7, wherein the ultrasonic surgical blade comprises a tissue-engaging surface that is parallel to the central waveguide axis, and wherein the tissue-engaging surface is transversely off-set past an outer surface of a shaft assembly containing the linear portion of the ultrasonic transmission waveguide.

9. An ultrasonic surgical instrument comprising: an ultrasonic transducer; an acoustic horn acoustically coupled to the ultrasonic transducer; an ultrasonic transmission waveguide acoustically coupled to the acoustic horn, the ultrasonic transmission waveguide having a central waveguide axis; and an ultrasonic surgical blade acoustically coupled to the ultrasonic transmission waveguide through a compound curvature component; wherein the compound curvature component transversely off-sets the ultrasonic surgical blade from the central waveguide axis.

10. The ultrasonic surgical instrument of clause 9, further comprising a shaft assembly comprising an outer sheath around at least a portion of the ultrasonic transmission waveguide, wherein the ultrasonic surgical blade is transversely off-set past an outer surface of the outer sheath.

11. The ultrasonic surgical instrument of clause 10, wherein the outer sheath comprises a closed and/or sealed slot extending longitudinally along at least a portion of the outer sheath length.

12. The ultrasonic surgical instrument of clause 11, wherein the closed and/or sealed slot comprises a sealing member positioned in the slot.

13. The ultrasonic surgical instrument of clause 11, wherein the closed and/or sealed slot comprises a shrunk tube positioned around the outer sheath circumference.

14. The ultrasonic surgical instrument of clause 11, wherein the closed and/or sealed slot comprises a bonded seam.

15. The ultrasonic surgical instrument of any one of clauses 9-14, wherein the ultrasonic transducer has a central transducer axis, the ultrasonic transmission waveguide comprises a curved portion and a linear portion, and the linear portion of the ultrasonic transmission waveguide and the ultrasonic surgical blade are angularly off-set from the central transducer axis.

16. The ultrasonic surgical instrument of clause 15, wherein the linear portion of the ultrasonic transmission waveguide defines the central waveguide axis, and wherein the central waveguide axis and the central transducer axis intersect and form an off-set angle ranging from 120-degrees to 150-degrees.

17. An ultrasonic surgical instrument comprising: an ultrasonic transducer; an ultrasonic transmission waveguide acoustically coupled to the ultrasonic transducer; and an ultrasonic surgical blade integrally formed with the ultrasonic transmission waveguide, wherein the ultrasonic transmission waveguide has a tapered width that decreases from a maximum at the acoustic coupling with the ultrasonic transducer to a minimum at a transition to the ultrasonic surgical blade.

18. The ultrasonic surgical instrument of clause 17, further comprising: a housing containing the ultrasonic transducer and the ultrasonic transmission waveguide; a clamp actuation member pivotably connected to the housing through a pivotable joint; and a clamp arm integrally formed with the clamp actuation member; wherein the housing and the clamp actuation member extend proximally from the pivotable joint; and wherein the clamp arm and the ultrasonic surgical blade extend distally from the pivotable joint.

19. The ultrasonic surgical instrument of clause 17 or clause 18, wherein the ultrasonic surgical blade comprises: a body portion acoustically coupled to the ultrasonic transmission waveguide; a bent portion forming a tissue-engaging surface; and a folded portion forming a gap between the body portion and the folded portion.

20. The ultrasonic surgical instrument of any one of clauses 17-19, wherein the ultrasonic transmission waveguide has a V-shaped cross-section.

21. The ultrasonic surgical instrument of any one of clauses 17-20, further comprising a transduction shaft integrally formed with the ultrasonic transmission waveguide, wherein the transduction shaft is located through an aperture extending through the length of the ultrasonic transducer, and wherein the ultrasonic transducer is clamped between proximal edges of the ultrasonic transmission waveguide and a cam lock extending through a proximal bore in the transduction shaft.

Various features and characteristics of the invention(s) are described in this specification and illustrated in the drawings to provide an understanding of the structure, function, operation, and/or manufacture of the disclosed instruments, devices, assemblies, systems, and methods. It is understood that the various features and characteristics of the invention(s) described in this specification and illustrated in the drawings can be combined in any suitable manner, regardless of whether such features and characteristics are expressly described or illustrated in combination in this specification. The Inventors and the Applicant expressly intend such combinations of features and characteristics to be included within the scope of the invention(s) described in this specification. As such, the claims can be amended to recite, in any combination, any features and characteristics expressly or inherently described in, or otherwise expressly or inherently supported by, this specification, including features and characteristics illustrated in the drawings. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims, and will comply with written description, sufficiency of description, and added matter requirements (e.g., 35 U.S.C. § 112(a) and Article 123(2) EPC).

The invention(s) described in this specification can comprise, consist of, or consist essentially of the various features and characteristics described in this specification. The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. Thus, an instrument, device, assembly, system, or method, and the like, that "comprises," "has," "includes," or "contains" one or more features and/or characteristics possesses those one or more features and/or characteristics, but is not limited to possessing only those one or more features and/or characteristics. Likewise, an element of an instrument, device, assembly, system, or method, and the like, that "comprises," "has," "includes," or "contains" one or more features and/or characteristics possesses those one or more features and/or characteristics, but is not limited to possessing only those one or more features and/or characteristics, and may possess additional features and/or characteristics.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described processes, compositions, and products. Further, the use of a singular noun includes the plural, and the use of a plural noun includes the singular, unless the context of the usage requires otherwise.

Any patent, publication, or other document identified in this specification is incorporated by reference into this specification in its entirety unless otherwise indicated, but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with written description, sufficiency of description, and added matter requirements (e.g., 35 U.S.C. § 112(a) and Article 123(2) EPC).

What is claimed is:

1. An ultrasonic surgical instrument comprising:
an ultrasonic transducer;
an ultrasonic transmission waveguide acoustically coupled to the ultrasonic transducer, wherein the ultrasonic transmission waveguide has a V-shaped cross-section;
an ultrasonic surgical blade integrally formed with the ultrasonic transmission waveguide, wherein the ultrasonic transmission waveguide has an uninterrupted tapered width that decreases from a maximum at an acoustic coupling with the ultrasonic transducer to a minimum at a transition to the ultrasonic surgical blade; and
a transduction shaft integrally formed with the ultrasonic transmission waveguide, wherein the transduction shaft is located through an aperture extending through the length of the ultrasonic transducer, and wherein the ultrasonic transducer is clamped between proximal edges of the ultrasonic transmission waveguide and a cam lock extending through a proximal bore in the transduction shaft.

2. The ultrasonic surgical instrument of claim 1, further comprising:
a housing containing the ultrasonic transducer and the ultrasonic transmission waveguide;
a clamp actuation member pivotably connected to the housing through a pivotable joint; and
a clamp arm integrally formed with the clamp actuation member;
wherein the housing and the clamp actuation member extend proximally from the pivotable joint; and
wherein the clamp arm and the ultrasonic surgical blade extend distally from the pivotable joint.

3. The ultrasonic surgical instrument of claim 1, wherein the ultrasonic surgical blade comprises:
a body portion acoustically coupled to the ultrasonic transmission waveguide;
a bent portion forming a tissue engaging surface; and
a folded portion forming a gap between the body portion and the folded portion.

4. The ultrasonic surgical instrument of claim 3, wherein the gap between the body portion and the folded portion of the ultrasonic surgical blade further comprises an isolation spacer, wherein the isolation spacer maintains separation between the body portion and the folded portion.

5. The ultrasonic surgical instrument of claim 1, wherein the ultrasonic transmission waveguide with the uninterrupted tapered width functions as an acoustic horn configured to amplify ultrasonic vibrations produced by the ultrasonic transducer.

6. The ultrasonic surgical instrument of claim 1, wherein the ultrasonic surgical blade is transversely offset from a central waveguide axis by a linear distance.

7. The ultrasonic surgical instrument of claim 1, wherein the ultrasonic surgical blade has a U-shaped cross-section.

8. The ultrasonic surgical instrument of claim 7, wherein the U-shaped cross-section of the ultrasonic surgical blade is transverse to a central waveguide axis at a tissue engaging surface of the ultrasonic surgical blade.

9. The ultrasonic surgical instrument of claim 1, wherein the V-shaped cross-section of the ultrasonic transmission waveguide is transverse to a central waveguide axis at an inward bend and an outward bend of the ultrasonic transmission waveguide.

* * * * *